(12) United States Patent
Lee et al.

(10) Patent No.: US 11,123,335 B2
(45) Date of Patent: Sep. 21, 2021

(54) METHOD FOR PREVENTING LUNG DISEASES IN SMOKERS AND NON-SMOKERS USING ANTIHYPERTENSIVE DRUG

(71) Applicant: SEOUL NATIONAL UNIVERSITY R & DB FOUNDATION, Seoul (KR)

(72) Inventors: Ho-Young Lee, Seoul (KR); Hye-Young Min, Seoul (KR); Hye-Jin Boo, Seoul (KR); Hyun-Ji Jang, Yeongju-si (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 168 days.

(21) Appl. No.: 15/784,538

(22) Filed: Oct. 16, 2017

(65) Prior Publication Data
US 2018/0125833 A1 May 10, 2018

Related U.S. Application Data

(63) Continuation-in-part of application No. PCT/KR2016/003957, filed on Apr. 15, 2016.

(30) Foreign Application Priority Data

Apr. 16, 2015 (KR) .................. 10-2015-0053921
Apr. 14, 2016 (KR) .................. 10-2016-0045773

(51) Int. Cl.
| | |
|---|---|
| *A61K 31/4422* | (2006.01) |
| *A61P 11/00* | (2006.01) |
| *A61P 35/00* | (2006.01) |
| *A61K 31/401* | (2006.01) |
| *A61K 31/4178* | (2006.01) |

(52) U.S. Cl.
CPC ........ *A61K 31/4422* (2013.01); *A61K 31/401* (2013.01); *A61K 31/4178* (2013.01); *A61P 11/00* (2018.01); *A61P 35/00* (2018.01)

(58) Field of Classification Search
CPC .............. A61K 31/401; A61K 31/4178; A61K 31/4422; A61P 11/00; A61P 35/00
See application file for complete search history.

(56) References Cited

U.S. PATENT DOCUMENTS

| | | | | |
|---|---|---|---|---|
| 7,371,772 B2 * | 5/2008 | Shiraishi | .............. | C07D 225/06 514/383 |
| 8,569,277 B2 * | 10/2013 | Yun | ...................... | A61K 31/192 514/182 |
| 8,883,145 B2 * | 11/2014 | Stagg | .............. | A61K 39/39558 424/130.1 |
| 9,498,437 B2 * | 11/2016 | Chaudry | .............. | A61K 9/0078 |
| 2004/0265238 A1 * | 12/2004 | Chaudry | .............. | A61K 9/0078 424/45 |
| 2005/0203169 A1 | 9/2005 | Moskowitz | | |
| 2006/0264384 A1 * | 11/2006 | Johansen | .............. | A61K 31/366 514/27 |

FOREIGN PATENT DOCUMENTS

| | | |
|---|---|---|
| WO | 2012/071573 A2 | 5/2012 |
| WO | 2014/018563 A2 | 1/2014 |

OTHER PUBLICATIONS

Millward et al., "Oral verapamil with chemotherapy for advanced non-small cell lung cancer: a randomised study", 1993, British Journal of Cancer, 67(5), pp. 1031-1035. (Year: 1997).*
Sajkov et al., "A Comparison of Two Long-Acting Vasoselective Calcium Antagonists in Pulmonary Hypertension Secondary to COPD", 1997, Chest, 111(6), pp. 1622-1630. (Year: 1997).*
Twiss et al., "Efficacy of calcium channel blockers as maintenance therapy for asthma", 2002, British Journal of Pharmacology, 53(3), pp. 243-249. (Year: 2002).*
Yoshida et al., "Antiproliferative effect of Ca2+ channel blockers on human epidermoid carcinoma A431 cells", 2003, European Journal of Pharmacology, 472(1-2), pp. 23-31. (Year: 2003).*
Chandy et al., "Current perspectives on treatment of hypertensive patients with chronic obstructive pulmonary disease", 2013, Integrated Blood Pressure Control, 6, pp. 101-109. (Year: 2013).*
Zangiabadi et al., "Pulmonary Hypertension and Right Heart Dysfunction in Chronic Lung Disease", 2014, BioMed Research International, Article ID 739674, pp. 1-13. (Year: 2014).*
Kale et al., "Targeting ion channels for cancer therapy byrepurposing the approved drugs", 2015, Biochimica et Biophysics Acta, 1848 (10, Part B), pp. 2747-2755. Available online Apr. 3, 2015. (Year: 2015).*
Boo et al., "The tobacco-specific carcinogen-operated calcium channel promotes lung tumorigenesis via IGF2 exocytosis in lung epithelial cells", 2016, Nature Communications, 7(12961), pp. 1-16 (Year: 2016).*
Bergelt et al., "Stressful life events and cancer risk", 2006, British Journal of Cancer, 95(11), pp. 1579-1581. (Year: 2006).*

(Continued)

*Primary Examiner* — My-Chau T. Tran
(74) *Attorney, Agent, or Firm* — Vorys, Sater, Seymour and Pease LLP; Mih Suhn Koh

(57) ABSTRACT

The present invention relates to a method for inhibiting lung diseases in smokers and non-smokers by blocking growth factor signaling using an antihypertensive drug, and more particularly, to a pharmaceutical composition for preventing lung cancer or emphysema, which contains an antihypertensive drug as an active ingredient. The present invention suggests a novel use of an antihypertensive drug which is being used in clinics, to prevent lung diseases, and therefore, may be readily applied to early lung cancer or a lung cancer high-risk group, and particularly may exclude safety concerns accompanying clinical application of novel drugs, thereby increasing clinical applicability. In addition, enormous costs and time needed from development to clinical use of new drugs may be dramatically reduced.

4 Claims, 44 Drawing Sheets

Specification includes a Sequence Listing.

(56) References Cited

OTHER PUBLICATIONS

Dziadziuszko et al., "The Insulin-Like Growth Factor Pathway in Lung Cancer", 2008, Journal of Thoracic Oncology, 3(8), pp. 815-818. (Year: 2008).*

Fidler et al., "Targeting the insulin-like growth factor receptor pathway in lung cancer: problems and pitfalls", 2012, Therapeutic Advances in Medical Oncology, 4(2), pp. 51-60. (Year: 2012).*

Attoub et al., "Captopril as a Potential Inhibitor of Lung Tumor Growth and Metastasis", Ann. N.Y. Acad. Sci., vol. 1138, pp. 65-72, (2008).

Chiu et al., "L-type calcium channel blockers reverse docetaxel and vincristine-induced multidrug resistance independent of ABCB1 expression in human lung cancer cell lines", Toxicology Letters, vol. 192, pp. 408-418, (2010).

Godugu et al., "Inhalation delivery of Telmisartan enhances intratumoral distribution of nanoparticles in lung cancer models", Journal of Controlled Release, vol. 172, pp. 86-95, (2013).

Laag et al., "NNK activates ERK1/2 and CREB/ATF-1 via $\beta$-1-AR and EGFR signaling in human lung adenocarcinoma and small airway epithelial cells", Int. J. Cancer, vol. 119, pp. 1547-1552, (2006).

Li et al., "Telmisartan Exerts Anti-Tumor Effects by Activating Peroxisome Proliferator-Activated Receptor-$\gamma$ in Human Lung Adenocarcinoma A549 Cells", Molecules, vol. 19, pp. 2862-2876, (2014).

Schuller, "Effects of tobacco constituents and psychological stress on the beta-adrenergic regulation of non-small cell lung cancer and pancreatic cancer: implications for intervention", Cancer Biomark., vol. 13, No. 3, pp. 133-144, (2013).

Yasumaru et al., "Inhibition of Angiotensin II Activity Enhanced the Antitumor Effect of Cyclooxygenase-2 Inhibitors via Insulin-Like Growth Factor I Receptor Pathway", Cancer Research, vol. 63, pp. 6726-6734, (2003).

* cited by examiner

METHOD FOR PREVENTING LUNG DISEASES IN SMOKERS AND NON-SMOKERS USING ANTIHYPERTENSIVE DRUG

SEQUENCE LISTING

The Sequence Listing submitted in text format (.txt) filed on Jan. 18, 2018, named "SequenceListing.txt", created on Jan. 17, 2018, 1.18 KB), is incorporated herein by reference.

TECHNICAL FIELD

The present invention relates to a method for preventing lung diseases by blocking growth factor signaling using an antihypertensive drug to inhibit the occurrence of lung cancer or emphysema in smokers and non-smokers, and more particularly, to a pharmaceutical composition for preventing lung diseases, which contains an antihypertensive drug as an active ingredient.

BACKGROUND ART

Lung cancer ranks as the No. 1 cause of cancer-related death worldwide. Despite the development of early diagnosis and treatment techniques, it has been known that the 5-year survival rate of lung cancer is approximately 20%, which is much lower than those of other types of cancer, and the 5-year survival rate of metastatic lung cancer is only 5%. Therefore, in addition to the development of an effective anticancer drug treating lung cancer, it is necessary to develop a chemical agent for preventing lung cancer which suppresses the occurrence of lung cancer or blocks the progression of lung cancer using a non-toxic material.

It has been known that 85 to 90% of cases of lung cancer results from smoking, and other causes such as stress, air pollution, inflammation, etc. result in lung cancer in non-smokers.

Until now, curcumin, resveratrol, diallyl disulfide, retinoids, aspirin, celecoxib, epigallocatechin gallate (EGCG), isothiocyanate, selenium, β-carotene, and N-acetyl-$_L$-cysteine have been known as effective materials in preventing cancer. However, most of these remain at the pre-clinical stage, and even some materials subjected to clinical trials did not exhibit significant effects, thus they have not been applied in clinical use as a cancer-preventing agent.

Meanwhile, today, as antihypertensive drugs, calcium channel blockers, beta-adrenergic receptor blockers, angiotensin-converting enzyme inhibitors, and angiotensin receptor antagonists have been known. In addition, it has been disclosed that a 6-pyrazolylamido-3-substituted azabicyclo[3.1.0]hexane derivative compound effective as a calcium channel regulator is used in treating a disease because of the suppressive effect on calcium channels (Korean Unexamined Patent Application Publication No. 10-2014-0134904).

However, the anticancer activity of a material blocking a antihypertensive-inducing mechanism such as a receptor blocker and changes in colon cancer or kidney cancer incidence in patients taking antihypertensive drugs using epidemiological investigation have been presented, but there is no case showing a substantial study result as a preventive drug thereof, and particularly, no report relating to a preventive effect of lung cancer has been known.

DISCLOSURE

Technical Problem

To solve the above-mentioned conventional technical problems, the present invention is directed to providing a method for preventing lung cancer or emphysema in smokers or non-smokers using a calcium channel blocker, an angiotensin-converting enzyme inhibitor and an angiotensin receptor antagonist, which are currently used as antihypertensive drugs, by blocking the activation of insulin-like growth factor signaling through the secretion of insulin-like growth factor 2 to inhibit the transformation of lung epithelial cells, the generation and growth of lung cancer cells, the occurrence of emphysema, and lung cancer formation.

However, technical problems to be solved in the present invention are not limited to the above-described problems, and other problems which are not described herein will be fully understood by those of ordinary skill in the art from the following description.

Technical Solution

To achieve the object, in one aspect, the present invention provides a method for preventing lung diseases, which includes administering a composition including any one selected from the group consisting of the antihypertensive drugs such as a calcium channel blocker, an angiotensin-converting enzyme inhibitor and an angiotensin receptor antagonist as an active ingredient to a subject.

In one exemplary embodiment of the present invention, the lung diseases may include lung cancer and emphysema.

In another exemplary embodiment of the present invention, the lung cancer or emphysema may be induced by smoking or stress.

In still another exemplary embodiment of the present invention, the calcium channel blocker may be selected from the group consisting of amlodipine, barnidipine, benidipine, cilnidipine, efonidipine, felodipine, isradipine, lacidipine, lercanidipine, manidipine, nicardipine, nifedipine, nilvadipine, nimodipine, nisoldipine, nitrendipine, verapamil and diltiazem.

In yet another exemplary embodiment of the present invention, the angiotensin-converting enzyme inhibitor may be selected from the group consisting of alacepril, benazepril, captopril, cilazapril, delapril, enalapril, fosinopril, imidapril, lisinopril, moexipril, perindopril, quinapril, ramipril, temocapril and zofenopril.

In yet another exemplary embodiment of the present invention, the angiotensin receptor antagonist may be selected from the group consisting of candesartan, eprosartan, fimasartan, irbesartan, losartan, olmesartan, valsartan and telmisartan.

In yet another exemplary embodiment of the present invention, the composition may inhibit the generation or secretion of insulin-like growth factor 2.

In yet another exemplary embodiment of the present invention, the composition may inhibit the activation of insulin-like growth factor receptor signaling.

In another aspect, the present invention provides a pharmaceutical composition for preventing lung diseases, which includes any one selected from the group consisting of the antihypertensive drugs such as a calcium channel blocker, an angiotensin-converting enzyme inhibitor and an angiotensin receptor antagonist as an active ingredient.

Advantageous Effects

The present invention can provide a method for preventing lung diseases by blocking growth factor signaling mediating a lung carcinogenic mechanism using an antihypertensive drug which is being currently used in clinics so as to prevent carcinogenesis in normal lung tissue or an early tumor, cancer development, and the occurrence of emphysema, resulting in the suppression of the onset or development of lung cancer or emphysema, based on lung carcinogenic mechanisms in smokers and non-smokers.

In addition, the present invention is a method capable of being readily applied to early lung cancer or a lung cancer-high risk group, suggesting a new use of an antihypertensive drug which is being clinically used to prevent lung cancer, and can particularly increase clinical applicability by excluding safety concerns associated with clinical application of new drugs, and dramatically reduce enormous costs and time required from the development of a new drug to clinical application.

In addition, the present invention is based on the research of mechanisms associated with regulation of signaling mediating lung carcinogenesis in smokers and non-smokers, and thus can be applied to different drugs capable of regulating mechanisms mediating lung carcinogenesis such as insulin-like growth factor receptor-mediated signaling, for example, other $Ca^{2+}$ and G protein-coupled receptor antagonists.

MODES OF THE INVENTION

Figure 1:
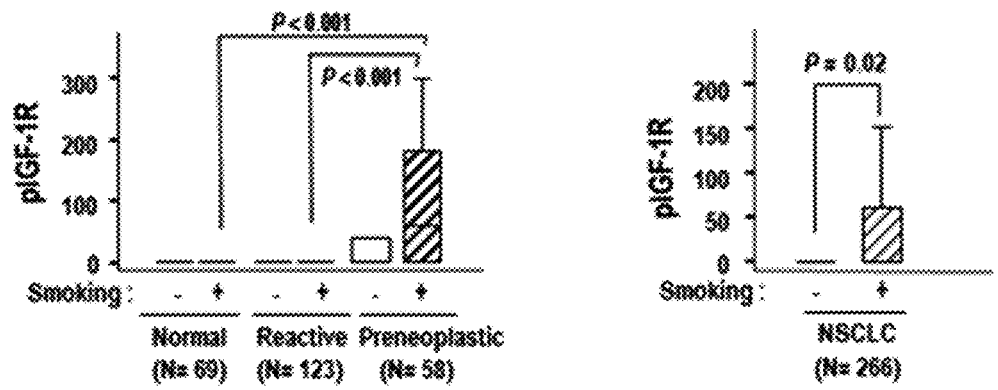
FIG. 1 shows that phosphorylated IGF-1R levels are high in preneoplasic lung tissues from people with a history of smoking, and activation of the IGF-1R signaling has a significant positive correlation with expression of ligands, IGF1 and IGF2.
Figure 1:
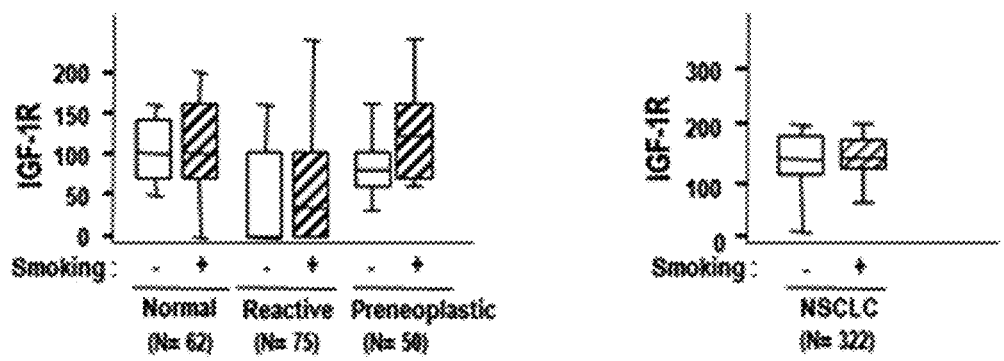
Figure 1:
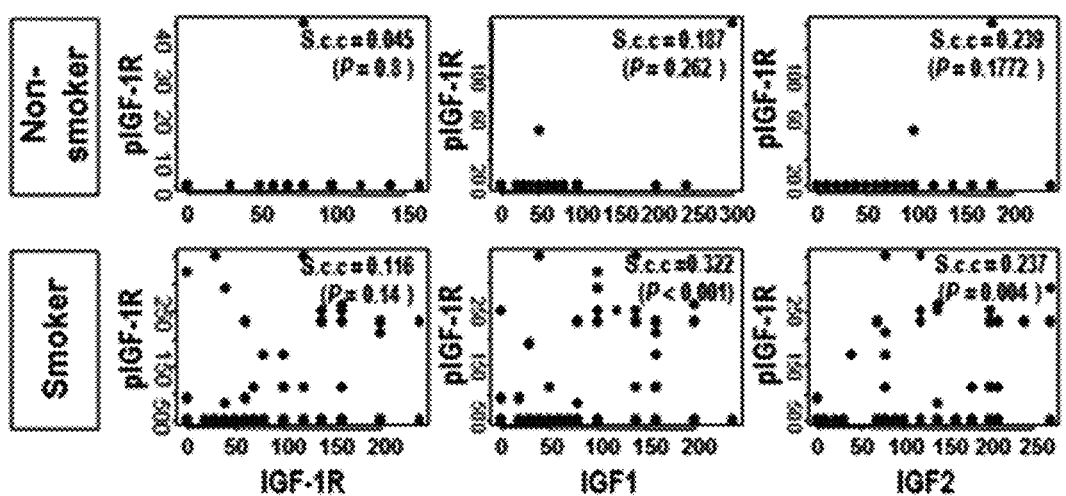

The present invention relates to a novel use of an antihypertensive drug in preventing lung cancer, and more particularly, to a novel use of an antihypertensive drug as a new indicant to prevent lung cancer by confirming activation of growth factor-mediated signaling in carcinogenic transformation of normal lung tissue, which is induced by a tobacco-derived carcinogen or stress, which is a non-smoker lung carcinogen, and identifying an inhibitory effect on transformation of lung epithelial cells, generation and growth of lung cancer cells, and lung carcinogenesis by blocking growth factor signaling activation using antihypertensive drugs which are being clinically used, such as a calcium channel blocker, an angiotensin-converting enzyme inhibitor and/or an angiotensin receptor antagonist.

Hereinafter, the present invention will be described in detail.

According to an exemplary embodiment of the present invention, insulin-like growth factor receptor (type 1 insulin-like growth factor receptor; IGF-1R) signaling, which is one type of growth factor-mediated signaling, is activated by a neurotransmitter, norepinephrine (NE), increased by 4-(methylnitrosamino)-1-(3-pyridyl)-1-butanone(NNK) which is a tobacco-specific carcinogen, and stress which is considered as a non-smoker lung cancer carcinogen.

According to another exemplary embodiment of the present invention, it is confirmed that tumorigenesis caused by a carcinogen is promoted in stress-induced experimental animals.

According to still another exemplary embodiment of the present invention, it is confirmed that the activation of IGF-1R signaling is inhibited by inhibiting NNK or NE-induced generation/secretion of insulin-like growth factor 2 (IGF2) or generation of angiotensinogen (AGT), which is an angiotensin precursor, by an antihypertensive drug, such as a calcium channel blocker, an angiotensin-converting enzyme inhibitor and/or an angiotensin receptor antagonist.

According to yet another exemplary embodiment of the present invention, lung carcinogenesis or emphysema in experimental animal models in which transformation of lung epithelial cells, generation and growth of lung cancer cells, lung carcinogenesis are induced by NNK or NE is inhibited by an antihypertensive drug, such as a calcium channel blocker, an angiotensin-converting enzyme inhibitor and/or an angiotensin receptor antagonist, and therefore, a method for preventing lung diseases using an antihypertensive drug is provided.

The antihypertensive drug, such as a calcium channel blocker, an angiotensin-converting enzyme inhibitor and/or an angiotensin receptor antagonist of the present invention blocks insulin-like growth factor receptor signaling, which is one type of growth factor-mediated signaling, and downstream signaling thereof, resulting in inhibiting transformation of lung epithelial cells, generation and growth of lung cancer cells, the occurrence of emphysema, and the occurrence of lung cancer.

The present invention provides a pharmaceutical composition for preventing lung diseases, which includes one or more selected from the group consisting of antihypertensive drugs such as calcium channel blockers, angiotensin-converting enzyme inhibitors and angiotensin receptor antagonists as an active ingredient.

The term "prevention" used herein refers to all actions of inhibiting the development of lung diseases or delaying the onset of lung diseases by administration with the pharmaceutical composition according to the present invention.

The term "lung diseases" used herein, which are subjected to prevention refers to diseases induced by the activation of IGF-1R signaling, and preferably, lung cancer and emphysema.

The term "lung cancer" used herein refers to a malignant tumor occurring in the lungs, which may be induced by smoking or stress.

The term "emphysema" used herein refers to a disease that causes chronic coughing or phlegm, difficulty in breathing, and reduction in lung capacity due to alveolus dysfunction induced by damage in lung tissues due to smoking and the like.

The term "calcium channel blocker" used herein refers to an agent for blocking the influx of extracellular $Ca^{2+}$ into the cells via the voltage-dependent calcium channel. Examples of the calcium channel blocker used herein may include, but are not limited to, dihydropyridine-based drugs such as amlodipine, barnidipine, cilnidipine, efonidipine, felodipine, isradipine, lacidipine, lercanidipine, manidipine, nicardipine, nifedipine, nilvadipine, nimodipine, nisoldipine, and nitrendipine; non-dihydropyridine-based drugs such as verapamil and diltiazem; and salts thereof. Specific chemical structures of the blockers are shown in Table 1 below.

TABLE 1

Dihydropyridine-based

Barnidipine

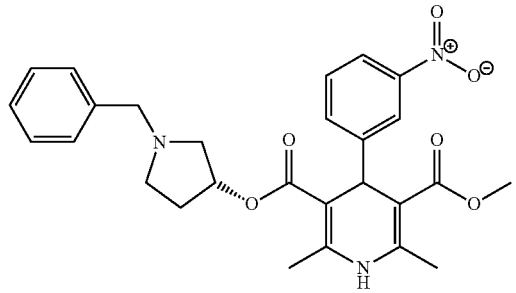

Benidipine

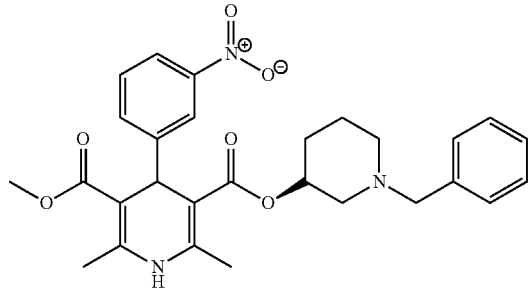

Cilnidipine

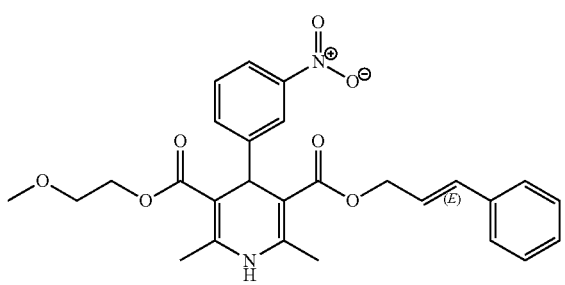

Efonidipine

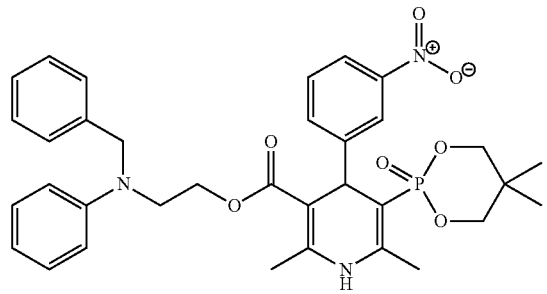

TABLE 1-continued
Felodipine
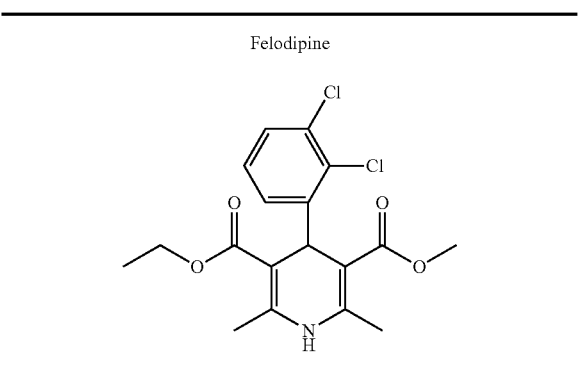
TABLE 1-continued
Manidipine
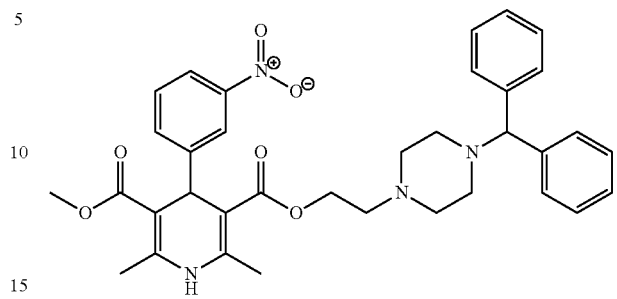
Isradipine
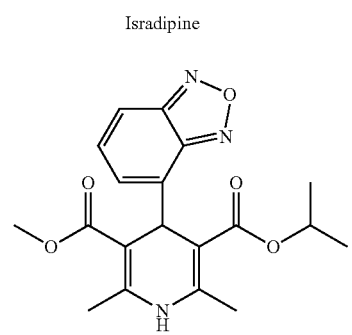 [SMILES: COC(=O)C1=C(C)NC(C)=C(C(=O)OC(C)C)C1c1cccc2nonc12]
Nicardipine
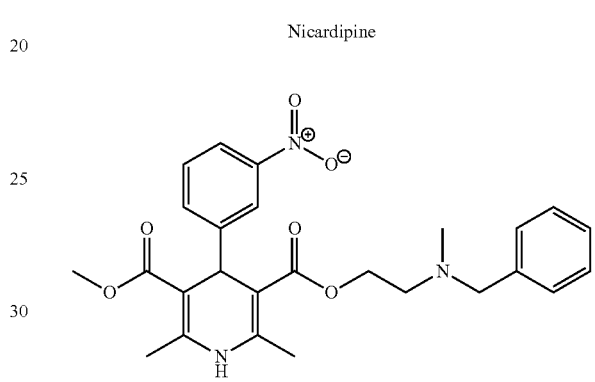
Lacidipine
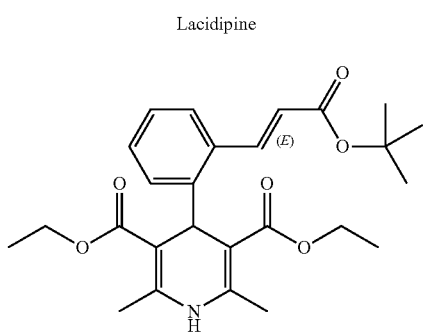 [SMILES: CCOC(=O)C1=C(C)NC(C)=C(C(=O)OCC)C1c1ccccc1/C=C/C(=O)OC(C)(C)C]
Nifedipine
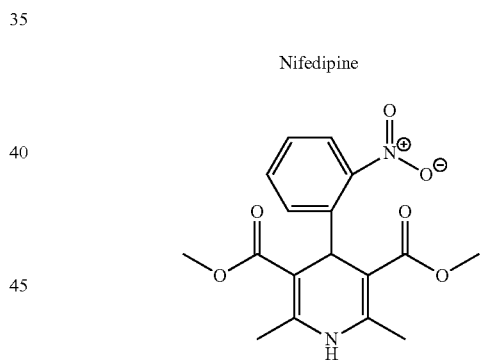
Lercanidipine
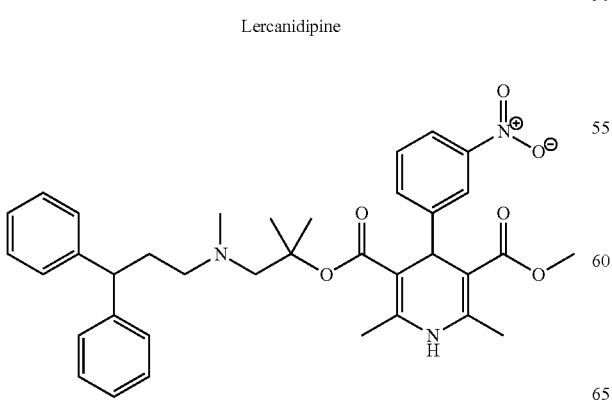
Nilvadipine
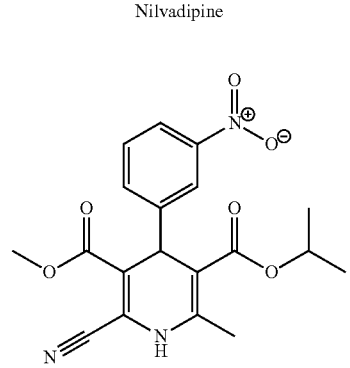 [SMILES: COC(=O)C1=C(C#N)NC(C)=C(C(=O)OC(C)C)C1c1cccc([N+](=O)[O-])c1]

TABLE 1-continued

Nimodipine

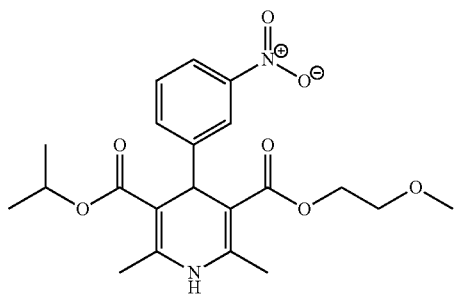

Nisoldipine

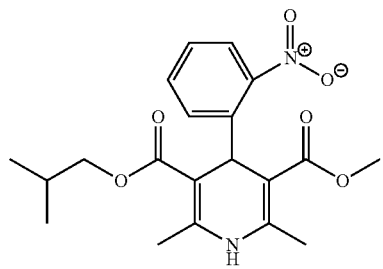

Nitrendipine

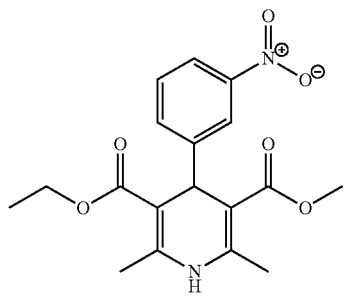

TABLE 1-continued

Non-dihydropyridine-based

Verapamil

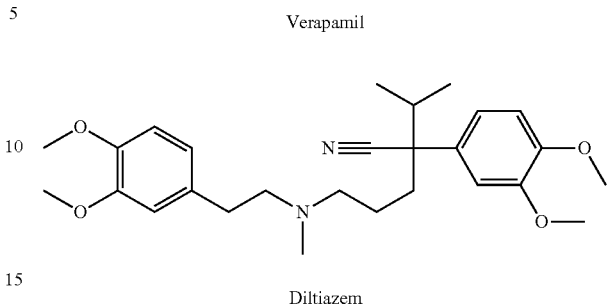

Diltiazem

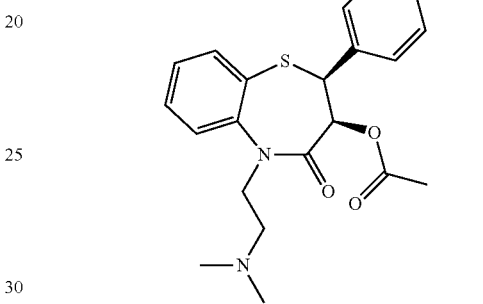

The term "angiotensin-converting enzyme inhibitor" used herein refers to an agent for inhibiting the action of angiotensin converting enzyme (ACE) converting angiotensin into angiontensin II, which serves to contract blood vessels, by cleaving a dipeptide (His-Leu) from a decapeptide (angiotensin I). Examples of the angiotensin-converting enzyme inhibitors used herein may include, but are not limited to, alacepril, benazepril, captopril, cilazapril, delapril, enalapril, fosinopril, imidapril, lisinopril, moexipril, perindopril, quinapril, ramipril, temocapril, zofenopril, and salts thereof, and the specific chemical structures of the inhibitors are shown in Table 2 below.

TABLE 2

Alacepril

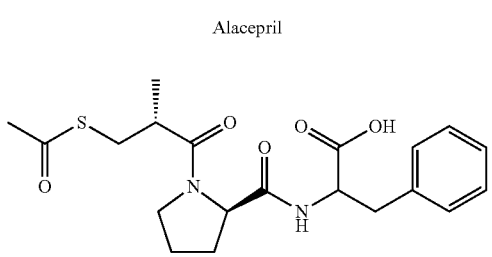 [SMILES: CC(=O)SC[C@H](C)C(=O)N1CCC[C@@H]1C(=O)NC(Cc1ccccc1)C(=O)O]

Benazepril

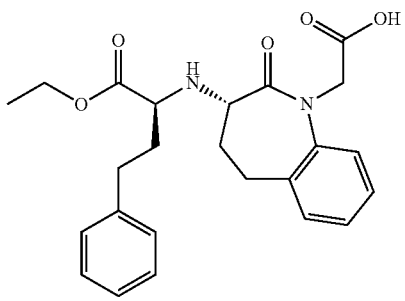

TABLE 2-continued
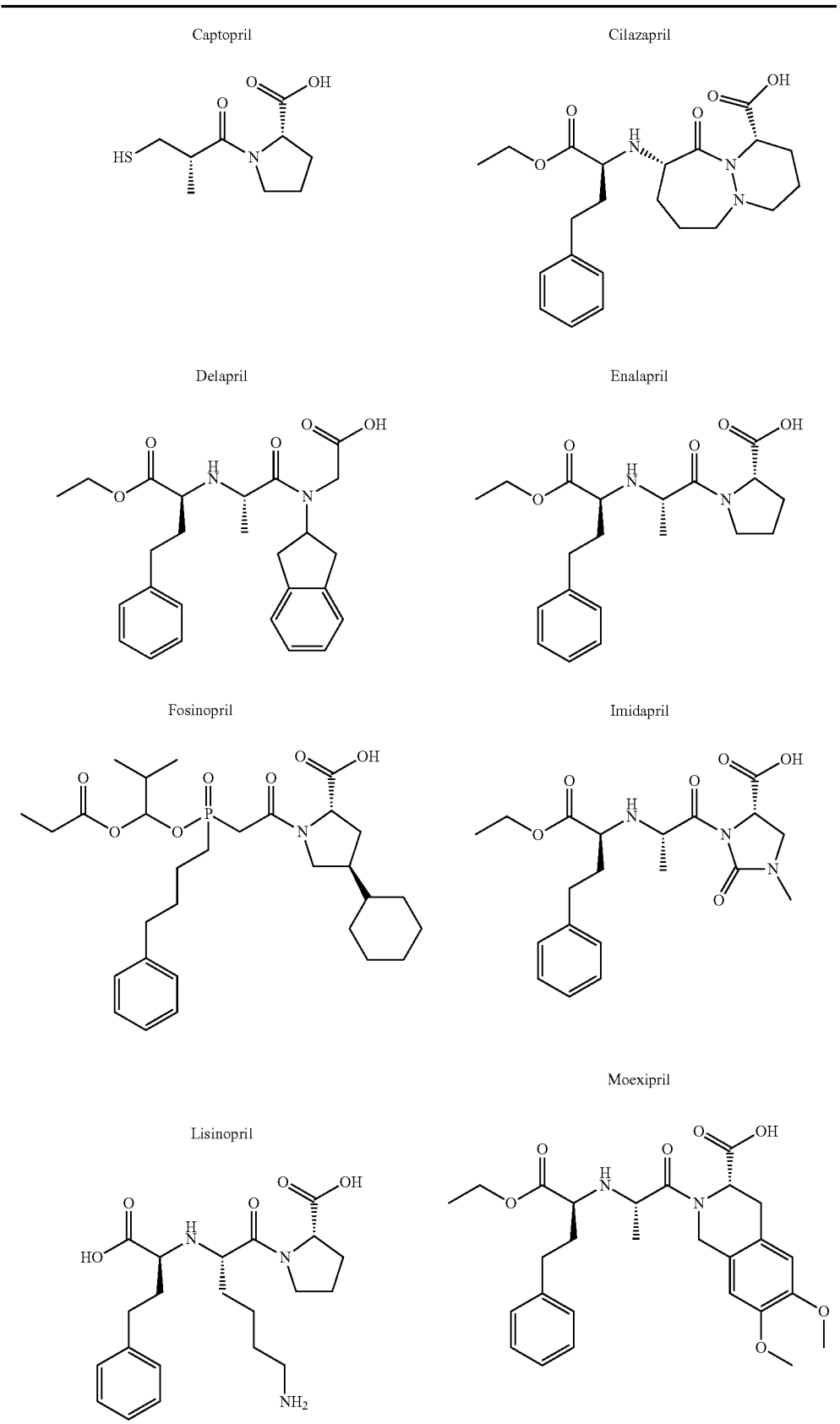

TABLE 2-continued

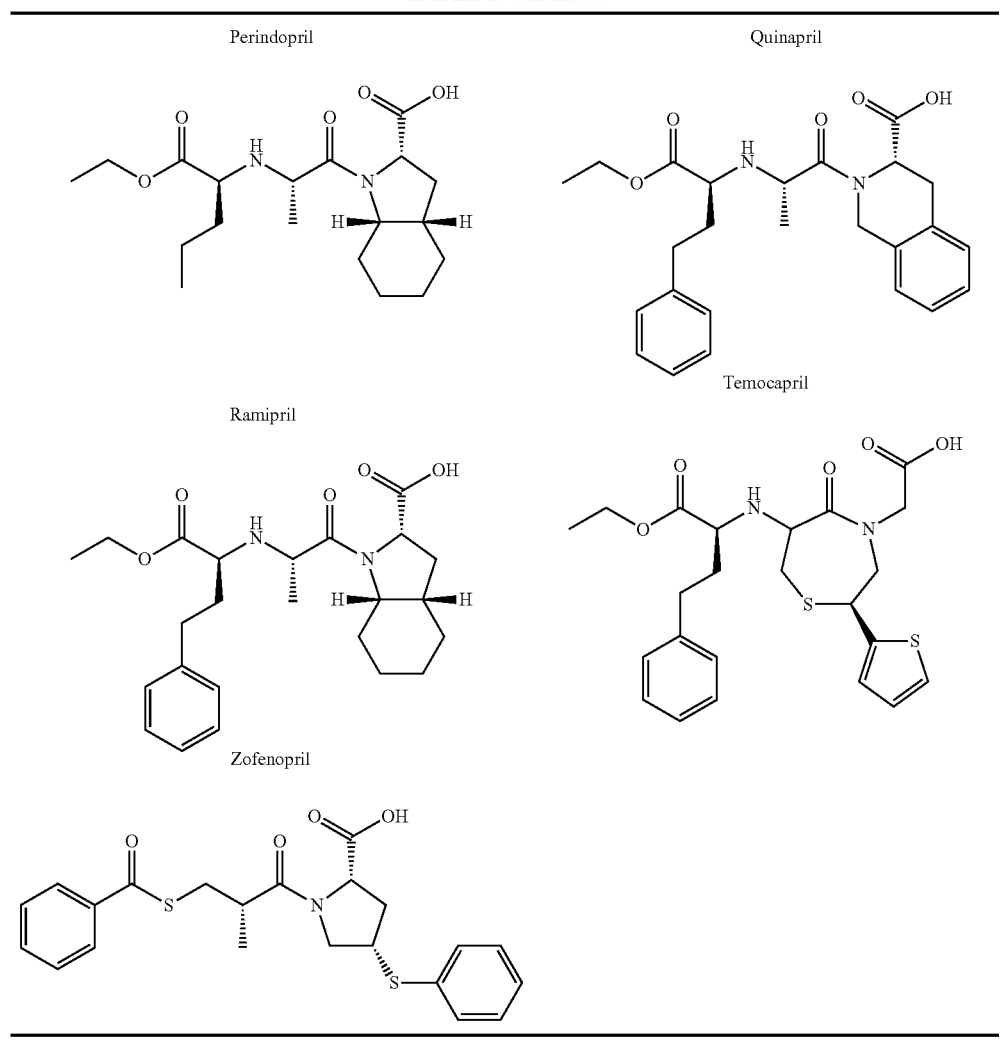

The term "angiotensin receptor antagonist" used herein refers to an agent for lowering blood pressure by preventing binding of angiotensin II to its receptor which is located on the wall of the blood vessel. Examples of the angiotensin receptor antagonists used herein may include, but are not limited to, candesartan, eprosartan, fimasartan, irbesartan, losartan, olmesartan, valsartan, telmisartan, and salts thereof, and the specific chemical structures of the antagonists are shown in Table 3.

TABLE 3

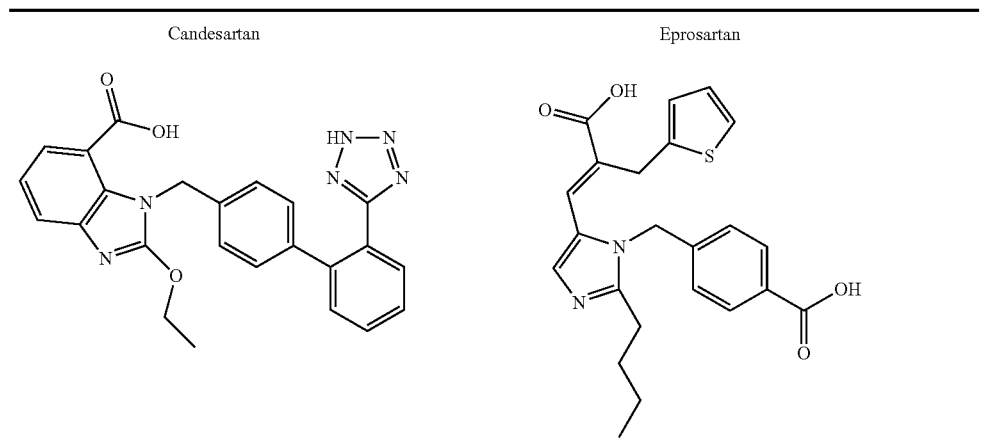

TABLE 3-continued

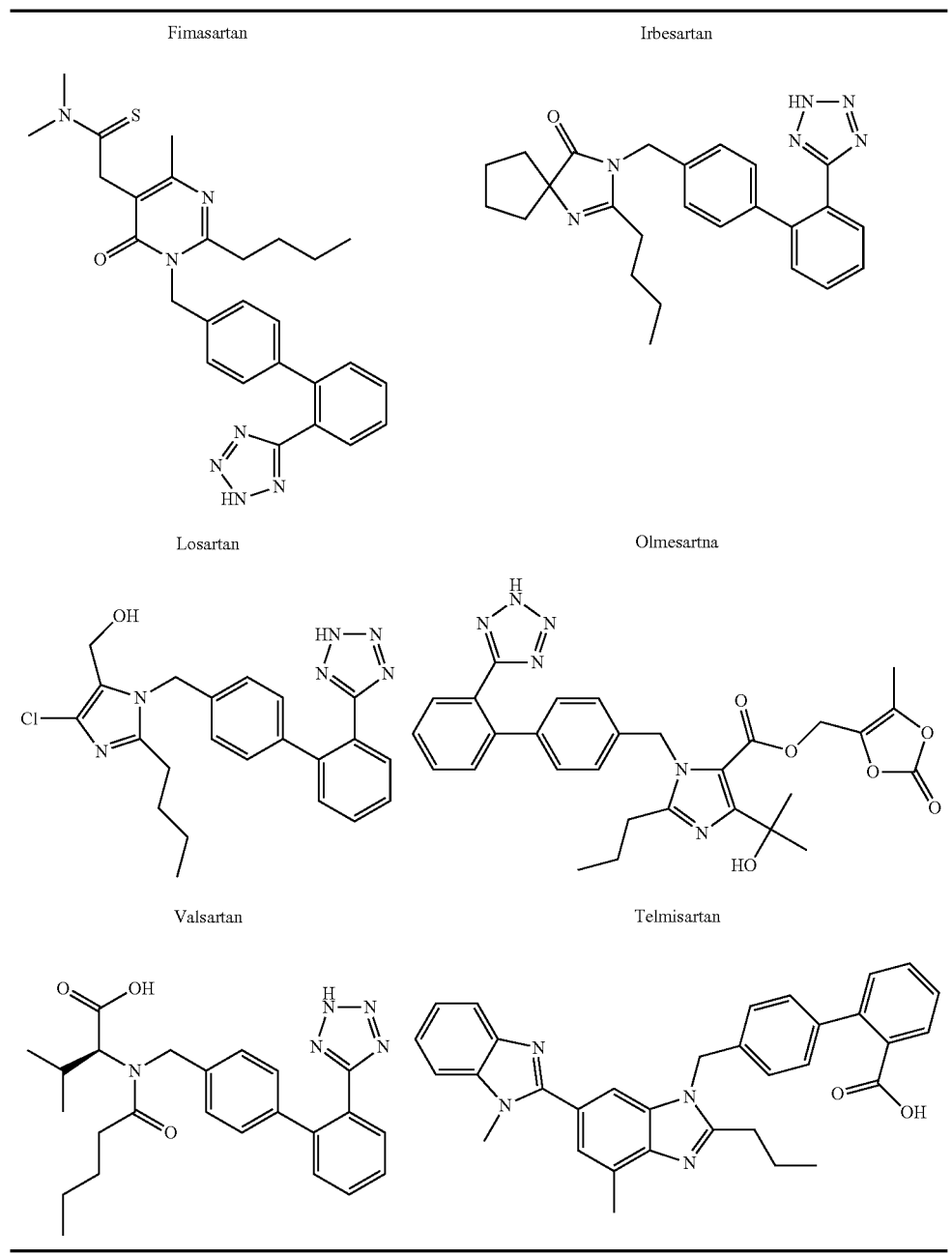

The present inventors confirmed activation of insulin-like growth factor-mediated signaling in lung carcinogenesis, and also confirmed inhibitory effects of a calcium channel blocker, an angiotensin-converting enzyme inhibitor and an angiotensin receptor antagonist, which are known as antihypertensive drugs, on transformation of lung epithelial cells resulting from the blockade of the growth factor signaling activation, and lung carcinogenesis.

Therefore, the calcium channel blocker, angiotensin-converting enzyme inhibitor and angiotensin receptor antagonist may inhibit the occurrence of lung cancer or emphysema, and may be used as an active ingredient of a composition for preventing lung diseases.

The composition of the present invention may further include one or more types of known active ingredients, which are effective in preventing lung cancer or emphysema, in addition to the calcium channel blocker, the angiotensin-converting enzyme inhibitor and the angiotensin receptor antagonist.

The composition of the present invention may further include a suitable carrier, excipient and diluent, which are conventionally used in preparation of a pharmaceutical composition. In addition, the composition may be used in dosage forms including an oral form such as powder, a granule, a tablet, a capsule, a suspension, an emulsion, a syrup, or an aerosol, a drug for external use, a suppository, or a sterilized injectable solution according to a conventional method suitable for each form.

Carrier, excipients and diluents which can be included in the composition may be lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinyl pyrrolidone, water, methylhydroxybenzoate, propylhydroxybenzoate, talc, magnesium stearate and mineral oil. The composition may be formulated with a diluent or an excipient such as a filler, a thickening agent, a binder, a wetting agent, a disintegrant, a surfactant, which are conventionally used.

A solid formulation for oral administration may be a tablet, pill, powder, granule or capsule, and such a solid formulation may be prepared by mixing at least one of excipients, for example, starch, calcium carbonate, sucrose, lactose and gelatin, with the active ingredient. Also, in addition to the simple excipient, lubricants such as magnesium stearate and talc may also be used. As a liquid formulation for oral administration, a suspension, a liquid for internal use, an emulsion, or a syrup may be used, and a generally-used simple diluent such as water or liquid paraffin, as well as various types of excipients, for example, a wetting agent, a sweetener, a fragrance and a preservative may be included. A formulation for parenteral administration includes a sterilized aqueous solution, a non-aqueous solvent, a suspension, an emulsion, a lyophilizing agent and a suppository. As the non-aqueous solvent or suspension, propylene glycol, polyethylene glycol, a vegetable oil such as olive oil, or an injectable ester such as ethyl oleate may be used. As a suppository base, Witepsol, Tween 61, cacao butter, laurin fat, or glycerogelatin may be used.

The term "administration" used herein refers to providing a predetermined composition to an individual by a suitable method.

A preferable dosage of the pharmaceutical composition of the present invention may be determined according to a condition and body weight of an individual, severity of a disease, a drug form, an administration route, and duration, by one of ordinary skill in the art. For preferable effects, the calcium channel blocker, angiotensin-converting enzyme inhibitor or angiotensin receptor antagonist of the present invention may be administered at 0.1 to 100 mg/kg, and preferably, 1 to 30 mg/kg once a day or several times a day.

The pharmaceutical composition of the present invention may be administered into an individual via various routes. All methods of administration may be expected, and the pharmaceutical composition of the present invention may be administered, for example, orally, or by rectal, intravenous, intramuscular, subcutaneous, epidural or intracerebroventricular injection. The pharmaceutical composition of the present invention is determined according to the type of active ingredient, in addition to various related parameters such as a disease to be treated, an administration route, a patient's age, sex and body weight, and the severity of a disease.

In addition, the pharmaceutical composition of the present invention may be used for prevention and treatment of lung cancer or emphysema independently or in combination with surgery, hormone treatment, drug treatment and methods using biological response modifiers.

As another aspect, the present invention provides a method for preventing lung cancer or emphysema, which includes: administering any one selected from the group consisting of antihypertensive drugs such as a calcium channel blocker, an angiotensin-converting enzyme inhibitor and an angiotensin receptor antagonist, to a subject. The subject includes a human, or non-human mammals, and the non-human mammals include, but are not limited to, a mouse, a rat, a dog, a cat, a horse, a cow, a sheep, a goat, a pig, and a rabbit.

Hereinafter, to help in understanding the present invention, exemplary embodiments will be disclosed. However, the following examples are merely provided to more easily understand the present invention, and the scope of the present invention is not limited to the examples.

EXAMPLES

Example 1. Preparation and Methods 1-1. Cell Culture

In the present invention, based on the finding that p53 mutations are frequently observed in lung carcinogenesis, normal human bronchial epithelial cells (NHBE), small airway epithelial cells (SAEC), immortalized human bronchial epithelial cell lines in which p53 was subjected to knockdown by siRNA transfection (HBE/p53i or HBEC/p53i), two immortalized human bronchial epithelial cell lines (BEAS-2B and HB56B), and lung cancer cells were used. In addition, cell lines established following exposure of BEAS-2B to a beeswax or beeswax containing a cigarette smoke condensate for 6 months, which are 1799, 1198 and 1170, were used, and considering that, due to the structural similarity between IGF-1R and IR, an antibody capable of detecting currently commercially available phosphorylated IGF-1R can also detect phosphorylated IR, for verification whether an NNK-induced increase in IGF-1R phosphorylation is specific for IGF-1R, a control group and IGF-1R or IR-overexpressing fibroblasts (R−, R+, IR+ cells) were used. The lung epithelial cells (NHBE, SAEC, HBE(C)/p53i, HB56B, BEAS-2B and 1799 cells) were cultured in keratinocyte SFM (KSFM) supplemented with EGF and pituitary extracts, and the 1198 and 1170 cells were cultured in 3% FBS-containing KSFM. The R−, R+, and IR+ cells were cultured in 10% FBS-containing DMEM, and the lung cancer cells were cultured in 10% FBS-containing RPMI 1640. The cells were subcultured one or twice a week at 37° C. with 5% $CO_2$.

1-2. Carcinogens

To evaluate smoking-induced carcinogenesis, a major carcinogenic nitrosamine in tobacco, such as 4-(methylnitrosamino)-1-(3-pyridyl)-1-butanone (NNK), was used, and to determine the association with stress considered as a non-smoker lung cancer carcinogen, norepinephrine (NE), which is a neurotransmitter increased during stress, was used. NNK was dissolved in DMSO, and NE was dissolved in PBS before use. A vehicle was processed to have a final concentration of 0.1% or less, to minimize an influence on the experiments by the vehicle. In in vivo experiments, NNK was dissolved in PBS and then orally or intraperitoneally administered.

1-3. Confirmation of Effect on Cell Growth

Cells (2-3×$10^3$ cells) were seeded into 96-well plates, treated with a test drug diluted with a medium, and then incubated for 3 days. After incubation, the cells were treated with an MTT solution to have a final concentration of 200-500 μg/ml and incubated for 2 to 4 hours. After discarding the medium, produced formazan was dissolved in DMSO, and then the absorbance at 570 nm was measured. Alternatively, cells were seeded into 12- or 24-well plates, collected after a predetermined time after treatment with a test drug, and then counted using a hemocytometer.

1-4. Anchorage-Dependent Colony Formation Assay 100 to 300 cells were seeded into 6- or 12-well plates and then treated with NNK or NNK and a test drug for 2 to 3 weeks. After 2 to 3 weeks, Colony formation was observed and the colonies were counted after stained staining with crystal violet.

1-5. Anchorage-Independent Colony Formation Assay

Before the experiment, low-melting agar (final concentration of agar: 1%) was diluted with a medium, and then 1 ml of the resulting solution was added and solidified in each 24-well plate, resulting in bottom agar. 2,000 to 5,000 cells were mixed with the low melting agar (final concentration of agar: 0.35-0.4%), 500 µl of the resulting mixture was added onto each bottom agar. After solidification of the agar, the cells were treated with NNK or a test drug, which was diluted with a medium. After 2 to 4 weeks after treatment, colonies were stained with an MTT solution, observed, and then counted.

1-6. Foci Formation Assay

Lung epithelial cells at 90 to 95% confluency were treated with a carcinogen diluted with a growth factor-free medium, or a carcinogen and a test drug. After 2 to 3 weeks, foci formation was observed.

1-7. Transfection

Lung epithelial cells and lung cancer cells were seeded into multi-well plates, and then transfected with siRNA (20~100 pmol) for 24 to 48 hours using Lipofectamine RNAiMAX. Alternatively, the seeded cells were transfected with IGF2 expression vectors (200 ng) for 24 hours using Lipofectamine 2000. The cells were harvested directly, or in a predetermined time after NNK treatment for Western blot analysis.

1-8. Establishment of Angiotensin Receptor or IGF2 Expression-Suppressed Cell Lines After shRNA vectors capable of suppressing angiotensin receptors or IGF2 expression were purchased from Sigma-Aldrich, HEK293T cells were transfected with the shRNA vectors together with viral packaging vectors, thereby producing lentiviral particles. Human lung epithelial cell lines were transfected with the lentiviral particles, treated with puromycin for 2 to 3 weeks for selection, resulting in establishment of a stable cell line. The established cell line (stable cell line) was subjected to Western blot analysis to determine whether the angiotensin receptor or IGF2 expression was suppressed.

1-9. Immunoprecipitation

Proteins isolated from cells were incubated with an antibody and protein A/G agarose to isolate a protein binding to the corresponding antibody. The presence of other proteins capable of interacting with a specific protein was determined by Western blot analysis.

1-10. Western Blot Analysis

Cells were washed twice with ice-cold PBS, and then lysed with a modified RIPA buffer [50 mM Tris-HCl (pH 7.4), 150 mM NaCl, 1 mM EDTA, 0.25% sodium deoxycholate, 1% Triton X-100, a protease inhibitor cocktail, 100 mM NaF, 1 mM $Na_3VO_4$]. Lysates were centrifuged at 13,000 rpm for 15 to 20 minutes to harvest supernatants, and then the collected proteins were quantified using the BCA method. Equivalent amounts of the proteins were subjected to electrophoresis using 8-15% SDS-PAGE, and then transferred to a PVDF membrane. The membrane was washed with TBST (0.01% Tween-20-containing Tris-buffered saline), and blocked in a blocking buffer (diluted in TBST to contain 5% skim milk) at room temperature for 1 hour. The membrane was incubated with primary antibodies diluted in 3% BSA-containing TBST at 4° C. for 12 hours, and washed with TBST for over 1 hour. The membrane was incubated with secondary antibodies diluted in TBST containing 3% skim milk at room temperature for 1 to 2 hours, and washed with TBST for over 1 hour. The membrane was reacted in an ECL solution, and band visualization was carried out by exposure to an X-ray film.

1-11. RT-PCR

RNA was isolated from lung epithelial cells by the following method. By adding TRIzol Reagent, the cells were homogenized, treated with chloroform and then centrifuged at 13,000 rpm for 20 minutes. After collection of supernatants, equivalent amounts of isopropanol were added, and then the resulting mixture was centrifuged at 13,000 rpm for 20 minutes to precipitate RNA. The precipitated RNA was washed with 75% ethanol, dried and then dissolved in nuclease-free water. The absorbance at 260 nm was measured, and then the RNA was quantified. RNA having a ratio of A260/A280 nm of 1.8 to 2.0 was used in the experiments. All of the experiments were carried out under RNase-free conditions.

cDNA was synthesized using the PrimeScript™ 1st strand cDNA Synthesis Kit by reacting 2 µg of total RNA with Oligo dT primer (50 µM), a dNTP mixture, and RNase-free $dH_2O$ at 65° C. for 5 minutes, reacting a Template RNA primer mixture with 5× PrimeScript Buffer, an RNase inhibitor, PrimeScript RTase, and RNase-free $dH_2O$ at 42° C. for 1 hour, and performing heating at 95° C. for 5 minutes to stop the reaction.

After a reaction solution was adjusted to a final volume of 20 µl by adding 2 µl cDNA, 4 µM primer sets, 10 µl EconoTaq® polymerase, and distilled water, polymerase chain reaction (PCR) was carried out using a PCR instrument. The PCR conditions were as follows: 25 to 33 cycles of 95° C./10 sec, 55~58° C./30 sec, and 72° C./1 min. PCR products were separated by 2% agarose gel electrophoresis, stained with ethidium bromide (EtBr) and visualized using a UV transilluminator to identify a specific band.

1-12. Confirmation of $Ca^{2+}$ Production in Cells

Lung epithelial cells were placed on coverslips, treated with an antihypertensive drug or a $Ca^{2+}$ chelator, treated with $Ca^{2+}$ indicator Fluo-4 AM at 37° C. for 15 minutes, and then treated with NE for 5 minutes. The cells were washed with PBS three times. The slides were mounted with a mounting medium, and images were captured using a Nuance multispectral imaging system (PerkinElmer).

For real-time monitoring of a $Ca^{2+}$ change in cells by NNK, the cells were seeded into 96-well cell carrier microplates (PerkinElmer), treated with an antihypertensive drug, treated with Fluo-4 AM at 37° C. for 15 minutes, and then treated with NNK. Fluorescence changes were monitored using an Operetta high content screening system, and result analysis was performed using Harmony software (PerkinElmer).

1-13. Immunofluorescence Staining

Cells were plated onto coverslips, pretreated with a drug and then treated with NNK or NE. OCT blocks were sliced to have a thickness of 4 µm and then placed onto silane-coated slides. Cells or tissue was washed with PBS, and fixed with 4% paraformaldehyde at room temperature for 30 minutes. Afterward, the cells were permeabilized with 0.1% Triton X-100, and blocked in a blocking solution. After treatment with primary antibodies at 4° C. for over 12 hours, the cells were washed with PBS several times, and then treated with fluorescence-binding secondary antibodies. Subsequently, after washing with PBS several times, the slides were mounted with a DAPI-containing mounting solution, and images were captured using a confocal microscope.

1-14. Real-Time Observation of Cells

Real-time observation of cells was performed using an Operetta high content screening system (PerkinElmer).

1-15. ELISA

ELISA for IGF1, IGF2 and NE were performed using commercially available ELISA kits (R&D Systems, DSL or Abnova) according to the manufacturer's instruction.

1-16. Stress-Induced Lung Carcinogenesis Models

After inducing stress in mice, promotion of a carcinogenic action mediated by urethane, which is a carcinogen, was observed. Stress induction was carried out by locking mice in a restrainer, dropping mice into water, shaking, or switching dark/light cycles for 4 months so as not to become acclimated to the environment. One month after the stress induction, some of the mice were treated with urethane as a carcinogen, and a direct increase in carcinogenesis and urethane-induced promotion of carcinogenesis by stress were evaluated.

To identify the carcinogenesis promotion by a stress hormone NE, NE (50.1 mM) or vehicle PBS was injected into micro-osmotic pumps (Alzet), and then the pumps were implanted into the backs of mice. Six weeks later, the existing pumps were removed, NE or PBS-injected new pumps were implanted into the mice, and then the mice were continuously exposed (daily exposure at a dose of 1 μmol per 100 g mouse) to NE for a total of 12 weeks. To stimulate tumorigenesis, three days after the pump implantation, urethane was administered at a dose of 1 g/kg.

For non-invasive observation of tumors before autopsy, MMPSense 680 probes were injected, and images were obtained using IVIS Spectrum microCT (PerkinElmer). After autopsy of the mice, lungs were extracted, and produced tumors were counted and embedded in paraffin to form paraffin blocks. Four or more tissue sections were prepared at regular intervals and stained by H&E staining, and then numbers and sizes of the tumors were measured to calculate volumes of the tumors. The tumor volume was calculated according to (minor axis)$^2$×major axis×0.5.

1-17. Lung Carcinogenesis Models and Evaluation of Inhibitory Effect of Antihypertensive Drug NNK (3 μmol) was orally administered to A/J mice twice a week, and a test drug was orally administered thereto 6 times a week for a total of 20 weeks. Afterward, the mice were sacrificed, lungs were extracted from the mice, and the produced tumors were counted. Lung paraffin blocks were prepared, four or more tissue sections were prepared at regular intervals, and then stained by H&E staining as described below. Numbers and sizes of the tumors were measured to calculate volumes of the tumors.

1-18. H&E Staining

Paraffin blocks were sliced to have a thickness of 4 μm, placed onto silane-coated slides, and then dried. The dried slide glasses were deparaffinized overnight in a 65° C. dry oven. Afterward, the slide glasses were dipped in xylene for 5 minutes twice. After deparaffinization, the slide glasses were sequentially hydrated with 100%, 95%, 70%, and 50% ethanol, stained with a Harris hematoxylin solution for 1.5 minutes, dipped in a 1% HCl alcohol solution and ammonia, and then counterstained with an eosin solution for 30 seconds. Afterward, the resulting tissue sections were sequentially dehydrated using 95% and 100% ethanol, transparentized with xylene, and then mounted. Images were captured using a microscope.

1-19. Immunohistochemistry

Paraffin blocks were sliced to have a thickness of 4 μm, placed onto silane-coated slides, and then dried. The dried slide glasses were deparaffinized overnight in a 65° C. dry oven. Afterward, the slide glasses were dipped in xylene for 5 minutes twice. After deparaffinization, the slide glasses were sequentially hydrated with 100%, 95%, 70%, and 50% ethanol, and treated with a hydrogen peroxide solution. The slide glasses were washed with PBS, treated with 0.4% Triton X-100, and blocked in a commercially available blocking solution (Dako). The slide glasses were treated with primary antibodies at 4° C. for over 12 hours, treated with PBS several times, and treated with biotin-binding secondary antibodies. The slide glasses were washed with PBS several times, treated with an ABC solution (Vector Laboratories), treated with a diaminobenzidine (DAB) solution, and mounted with a mounting solution, and then images were captured.

1-20. Retrieval and Analysis of Bronchoalveolar Lavage Fluid (BALF)

Mice were exposed to stress for 4 weeks, and three days after the stress exposure, lungs were extracted from antihypertensive drug-administered mice. The inside of the lungs was washed with PBS three times, and the bronchoalveolar lavage fluid (BALF) was retrieved. The BALF was concentrated with Amicon Ultra (EMD Millipore), and IGF2 was detected by Western blot analysis. Separately, a gel was stained with Coomassie brilliant blue to check whether the same concentrates were analyzed, and IGF2 blots were quantified and plotted using Image J.

1-21. Construction of SPC-IGF2 Transgene Expression Vectors

A transformation vector SPC-kbpA for preparing transgenic mice was kindly provided from Dr. DeMayo (Baylor Medical School). Human IGF2 cDNA with a length of 600 bp was subcloned at an EcoRI site of the PC-kbpA vector, thereby constructing an SPC-IGF2 plasmid. Therefore, the SPC-IGF2 plasmid was constructed such that IGF2 gene expression is regulated by a surfactant protein C (SPC) promoter.

1-22. Preparation of Transgenic Mice

SPC-IGF2 plasmids were treated with restriction enzymes NdeI and NotI to cleave a SPC/IGF2 transgene. After a 6-kb insert was isolated through gel electrophoresis, the transgene was microinjected into hybrid C3H/C57B6 fertilized mouse eggs.

Mice containing the human IGF2 transgene were identified by PCR analysis. Genomic DNA was isolated from a part of the mouse tail, and amplified using primers for 700 bp of the SPC promoter/IGF2 coupled region through PCR. The primer sequences used herein were the forward primer 5'-AGACACCAATGGGAATCC-3', and the reverse primer 5'-TGCTCACTTCCGATTGCTG-3'. The PCR was performed as a total of 35 cycles of initial denaturation at 95° C. for 5 minutes, at 95° C. for 45 seconds, at 58° C. for 45 seconds, and at 72° C. for 45 seconds, and final extension at 72° C. for 7 minutes. The resulting PCR product was isolated by electrophoresis using a 2% agarose gel containing a RedSafe dye, and visualized using a UV transilluminator to check the presence of IGF2.

1-23. Construction of SPC-IGF-1R Transgene Expression Vectors

A transformation vector for preparing transgenic mice, SPC-kbpA, was kindly provided from Dr. DeMayo (Baylor Medical School). IGF-1R cDNA was subcloned in a PC-kbpA, thereby constructing a SPC-IGF-1R plasmid. Therefore, the SPC-IGF-1R plasmid was constructed such that IGF-1R gene expression is regulated by a surfactant protein C (SPC) promoter.

1-24. Preparation of Transgenic Mice

SPC-IGF-1R plasmid constructs were microinjected into hybrid C3H/C57B6 fertilized mouse eggs. Mice containing the human IGF-1R transgene were identified by PCR analysis. Genomic DNA was isolated from a part of a mouse tail, and amplified using primers for the SPC promoter/IGF-1R coupled region through PCR. The primer sequences used herein were the forward primer 5'-CTGGCTGGCGTG-GAAATATTC-3', and the reverse primer 5'-CCACTCG-GAACAGCAGCAAG-3'. The PCR was performed as a total of 35 cycles of initial denaturation at 95° C. for 5 minutes, at 95° C. for 45 seconds, at 58° C. for 45 seconds, and at 72° C. for 45 seconds, and final extension at 72° C. for 7 minutes. The resulting PCR product was isolated by electrophoresis using a 2% agarose gel containing a RedSafe dye, and visualized using a UV transilluminator to check the presence of IGF1R. The mice were backcrossed 8 or more generations to a FVB/N background.

1-25. Investigation of Emphysema Preventing Effect of Antihypertensive Drug Using Emphysema-Induced Mouse Models Tobacco's main ingredients, NNK and benzo[a]pyrene (NNK/B[a]P), which induce emphysema, were dissolved in cottonseed oil, and each ingredient was orally administered to an 8 week-old FVB mouse at 3 µmol for one week. A calcium channel blocker, amlodipine, (0.8 mg/kg; dissolved in a DDW 45%: PEG-400 45%: DMSO 10% solution) was orally administered to the mouse together with NNK/B[a]P. The NNK/B[a]P was administered twice a week, and the amlodipine was administered 6 times a week for a total of 5 months.

1-26. In Situ Zymography

As a method for detecting the activation degree of a protease, a matrix metalloproteinase (MMP), known as the main factor causing COPD in lung tissue, a proper amount of a reaction buffer containing fluorescein isothiocyanate (FITC)-coupled DQ gelatin was added to a slide, and reacted at 37° C. in a dark room for 12 hours. The activated MMP decomposed the DQ gelatin, resulting in fluorescence from FITC which had been inhibited, and thus the fluorescence intensity of FITC was directly proportional to MMP activity.

1-27. TUNEL Staining

As a method for identifying DNA fragmentation, which is one of the typical events shown in induction of cell apoptosis, the hydroxyl group at the 3' end exposed by DNA fragmentation using terminal deoxynucleotidyl transferase (TdT) was labeled with TMR red-dUTP, and then images were captured using a fluorescence microscope to identify apoptosis-induced cells. Labeling was performed using a commercially available kit manufactured by Roche.

1-28. Measurement of Lung Function

A catheter was injected into the airway of a mouse anesthetized with ketamine/rompun, a muscle relaxant was injected into the mouse, and then the mouse was connected to a FlexiVent system (Scireq, Montreal, Ontario, Canada) to measure a lung function. A volume of the lung was normalized by a deep inflation method in which the mouse was first ventilated to have a single breathing capacity of 10 ml/kg and a frequency of 150 times/min, with a pressure of maximum 30 cm $H_2O$ for 6 minutes before the measurement of the lung function of each subject. To measure lung compliance, a Snapshot-150 method in which a volume corresponding to a single breathing capacity was applied with an oscillation of 2.5 Hz for 1.25 seconds was performed. Then, tissue compliance was measured using a Quick Prime-3 method for obtaining an impedance of the total respiration system by a random number of movements of vibration frequency for 3 seconds. Finally, to plot a pressure-volume curve, a PVs-P method was performed. Each method was repeated three times at 30 second intervals.

Example 2: Confirmation of Specific Activation of the Insulin-Like Growth Factor Receptor (IGF-1R) Signaling in Lung Epithelial Cells and Mouse Lung Tissues Treated with a Tobacco-Derived Carcinogen First, it was investigated whether phosphorylated IGF-1R levels was increased in preneoplastic lung tissues from patients with a history of smoking. As a result, as shown in FIG. 1, in the preneoplastic lung tissue from patients with a history of smoking, it was confirmed that phosphorylated IGF-1R levels were increased. In addition, by investigating the correlation between the activation of such IGF-1R signaling and a ligand, as shown in FIG. 1, it was confirmed that the activation of the IGF-1R signaling has a significant positive correlation with the expression of ligands, IGF1 and IGF2.

Figure 2:
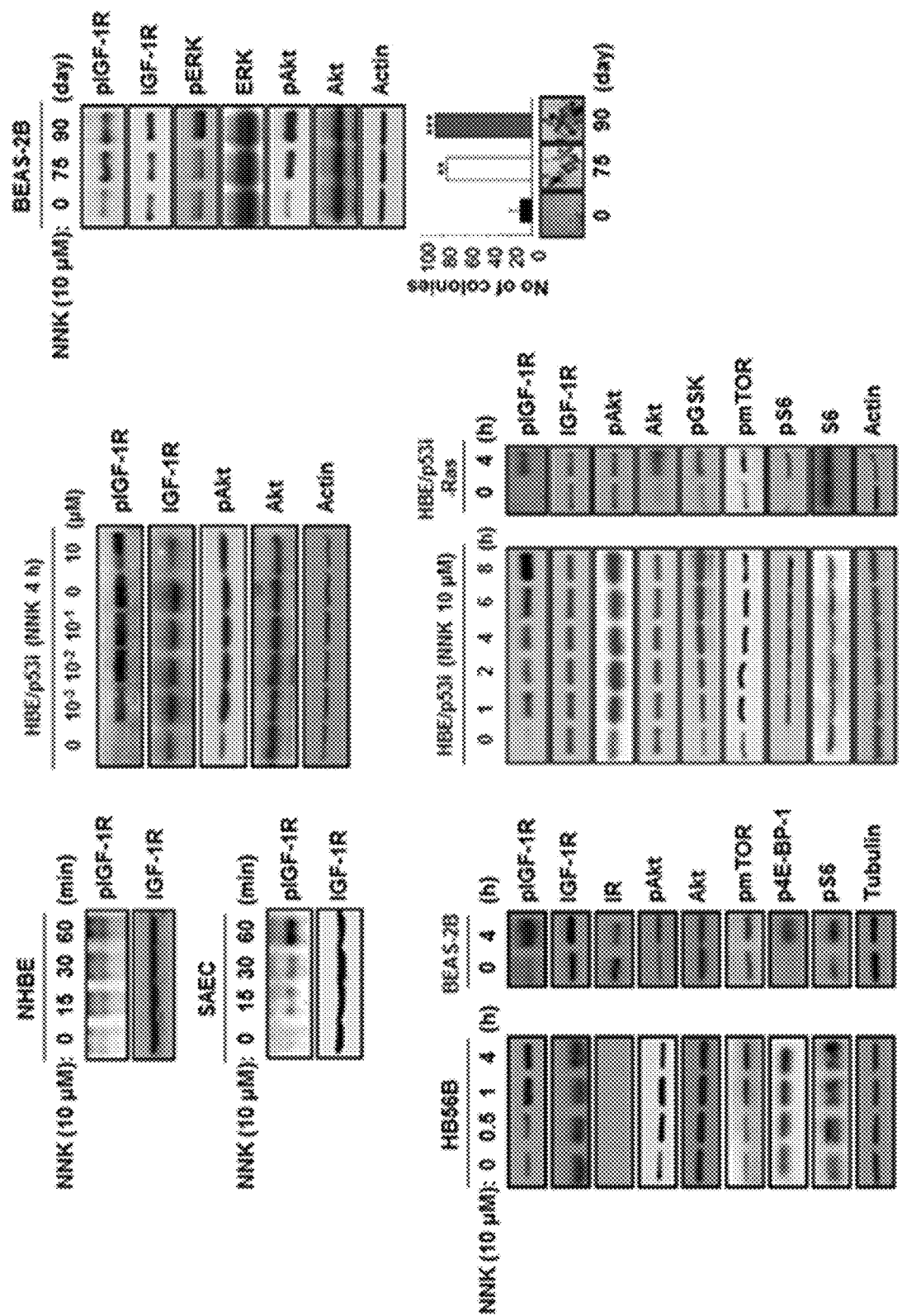
FIG. 2 shows that activation of IGF-1R, and activation of Akt, mTOR or ERK in the downstream signaling thereof are increased in lung epithelial cells according to the increase in time and concentration for tobacco-derived carcinogen NNK treatment.

In addition, various lung epithelial cells (NHBE, SAEC, HBE/p53i, HB56B, and BEAS-2B) was each treated with the tobacco-derived carcinogen, NNK, at different concentrations and for different times, and whether activation of IGF-1R and downstream signaling thereof was changed was investigated by the above-described method in Example 1-10. As a result, as shown in FIG. 2, it was confirmed that, as NNK treatment time or concentrations are increased, the activation of IGF-1R and its downstream signaling mediators such as Akt, mTOR, and ERK is increased in various lung epithelial cells.

Figure 3:
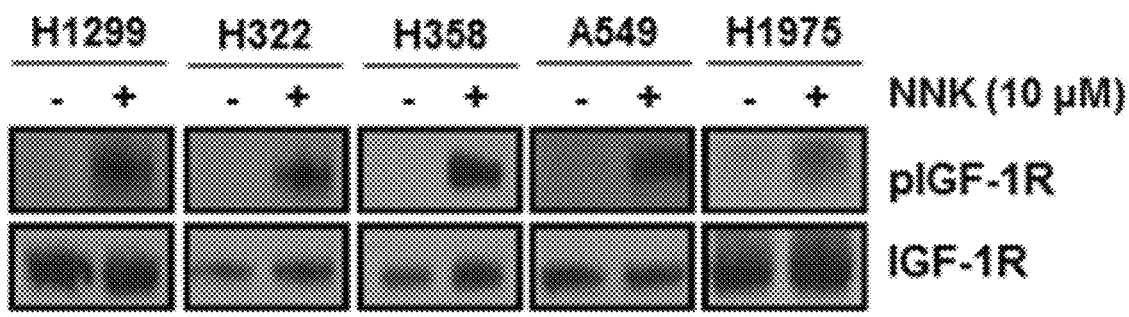
FIG. 3 shows that IGF-1R is activated by NNK in various lung cancer cells with different genotypes.

Moreover, as the result of identifying the change in IGF-1R activation using the method described in Example 1-10, after various lung cancer cells with different genotypes were treated with NNK (10 µM), as shown in FIG. 3, it was confirmed that IGF-1R was activated by NNK.

Figure 4:
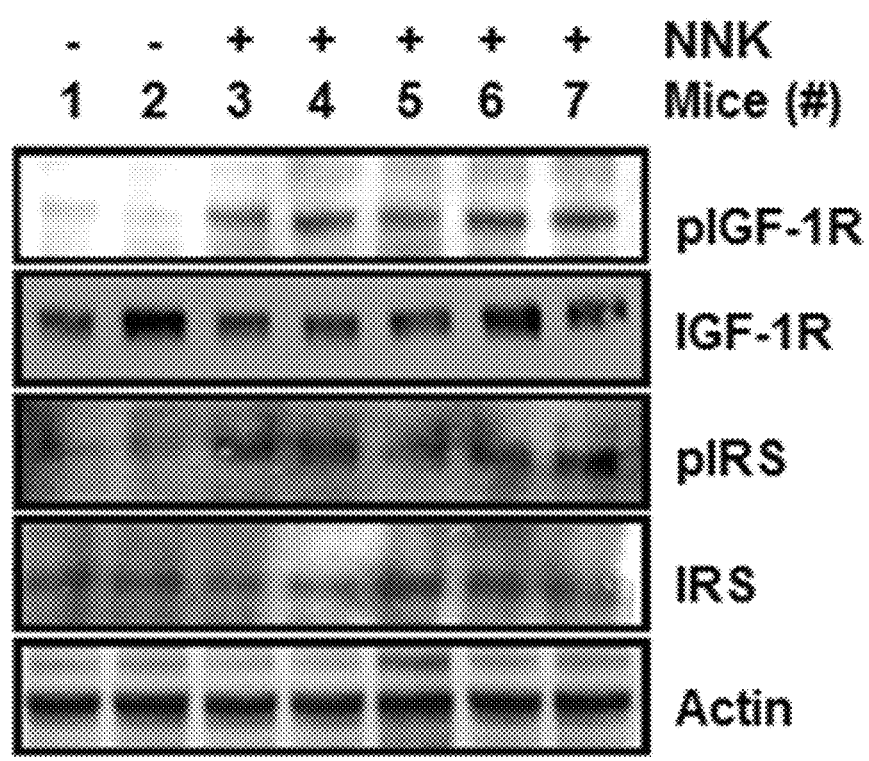
FIG. 4 shows that activation of IGF-1R and IRS, which is downstream signaling thereof, is increased in lung tissues from NNK-treated A/J mice.

In addition, as the result of identifying the change in IGF-1R activation by the method described in Example 1-10 after A/J mice were treated with NNK (3 µmol) and sacrificed to extract lung tissue, as shown in FIG. 4, it was confirmed that the activation of IGF-1R and its downstream signaling IRS was increased.

Figure 5:
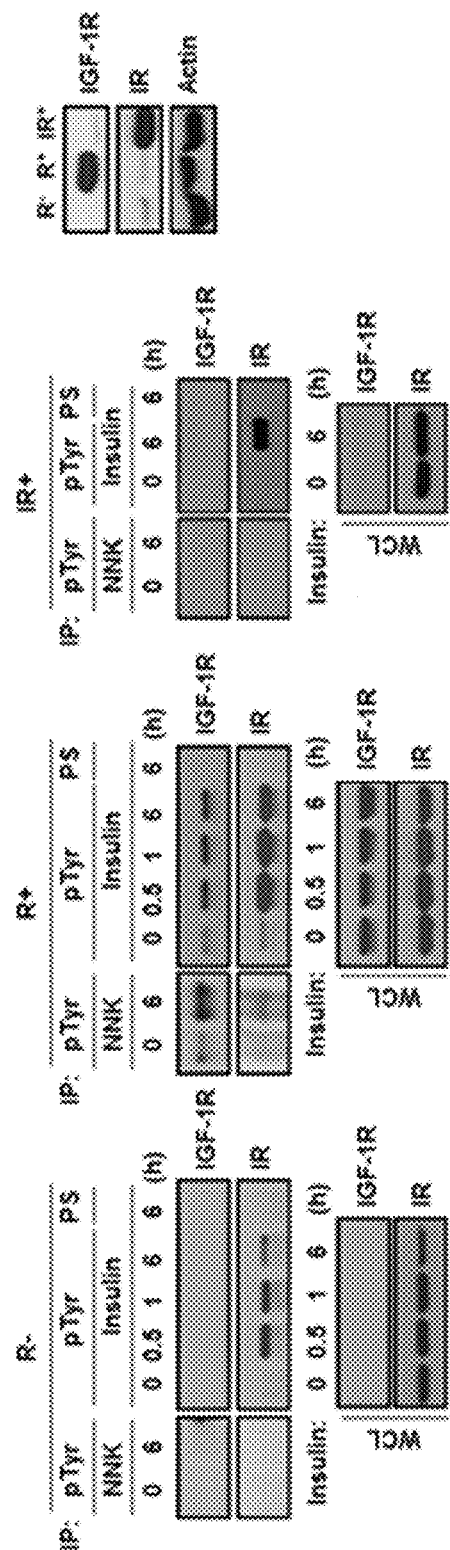
FIG. 5 shows that an increase in NNK-induced IGF-1R phosphorylation is selectively exhibited in IGF-1R, not in IR, which has structural similarity to IGF-1R.
Figure 6:
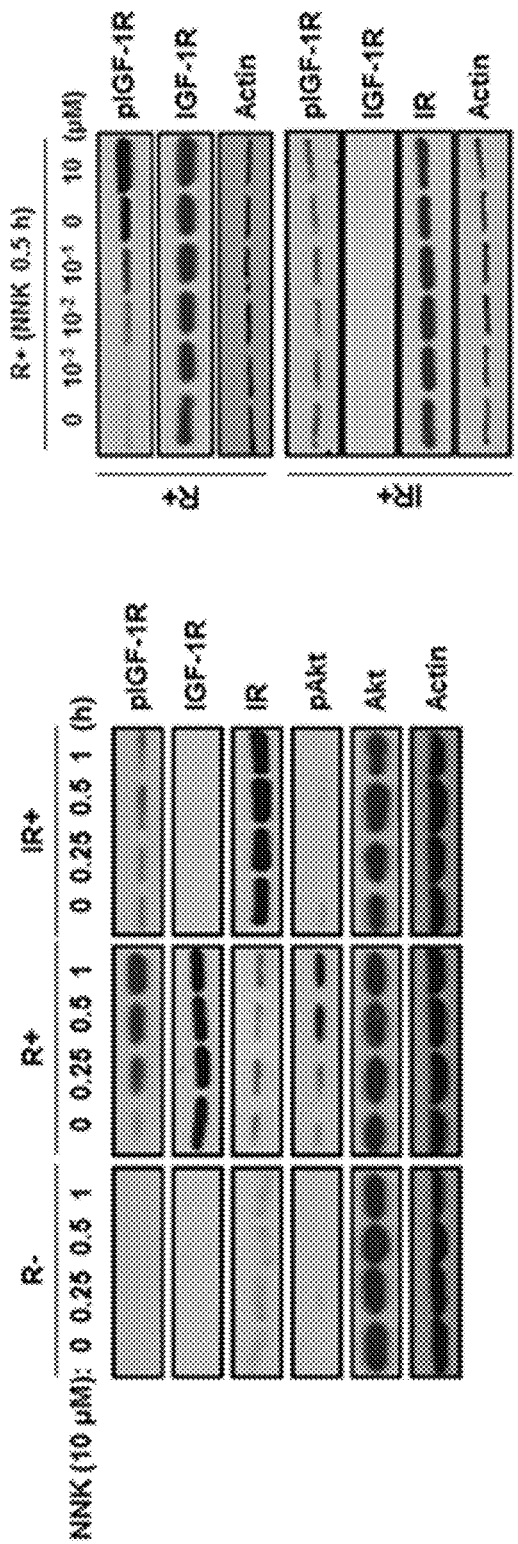
FIG. 6 shows that the increases in time- and concentration-dependent IGF-1R phosphorylation by NNK treatment are clearly identified in IGF-1R-overexpressing fibroblasts, which are R+ cells, indicating IGF-1R selective phosphorylation induced by NNK like the result of FIG. 5.

Moreover, to identify whether an NNK-induced increase in IGF-1R phosphorylation is specific for IGF-1R, IGF-1R or IR-overexpressing fibroblasts (R−, R+, IR+ cells) were time-dependently treated with NNK (10 µM), and protein bands were visualized by the method described in Example 1-9. As a result, as shown in FIGS. 5 and 6, the increase in IGF-1R phosphorylation was noticeably shown in IGF-1R-overexpressing fibroblasts R+ cells, indicating that the NNK-induced increase in IGF-1R phosphorylation was specifically shown for IGF-1R, not for IR which has structural similarity.

Figure 7:
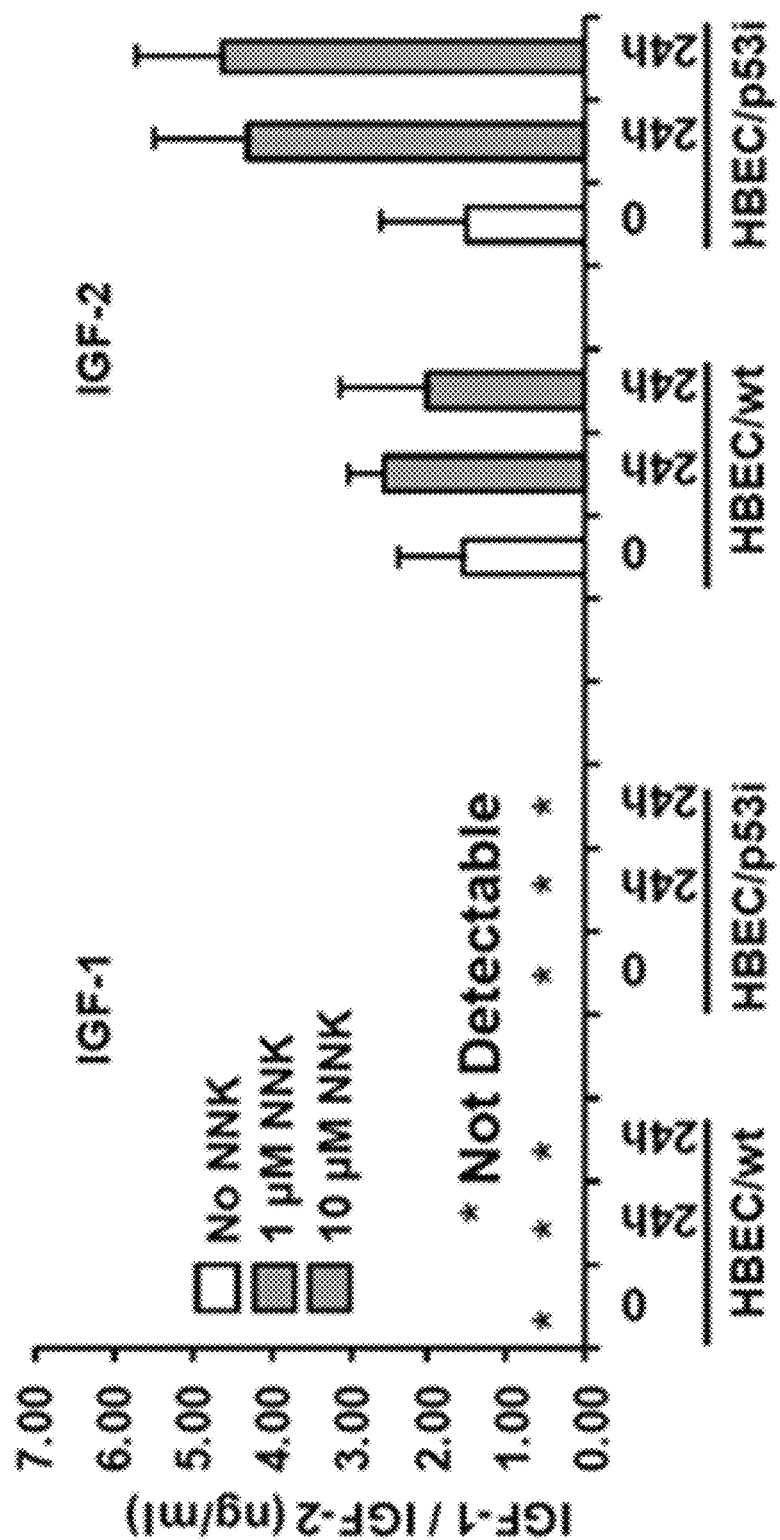
FIG. 7 shows that IGF2 production is increased by NNK treatment.

Examples 3: Confirmation of Correlation Between Tobacco Carcinogen NNK-Induced IGF-1R Signaling Activation Via Increase in IGF2 Generation/Secretion in Lung Epithelial Cells and Induction of Transformation of Lung Epithelial Cells First, lung epithelial cells were treated with NNK (1 or 10 µM), and the generation of IGF1 and IGF2 was compared by the method described in 1-11. As a result, as shown in FIG. 7, it was confirmed that IGF2 generation was increased by NNK treatment.

Figure 8:
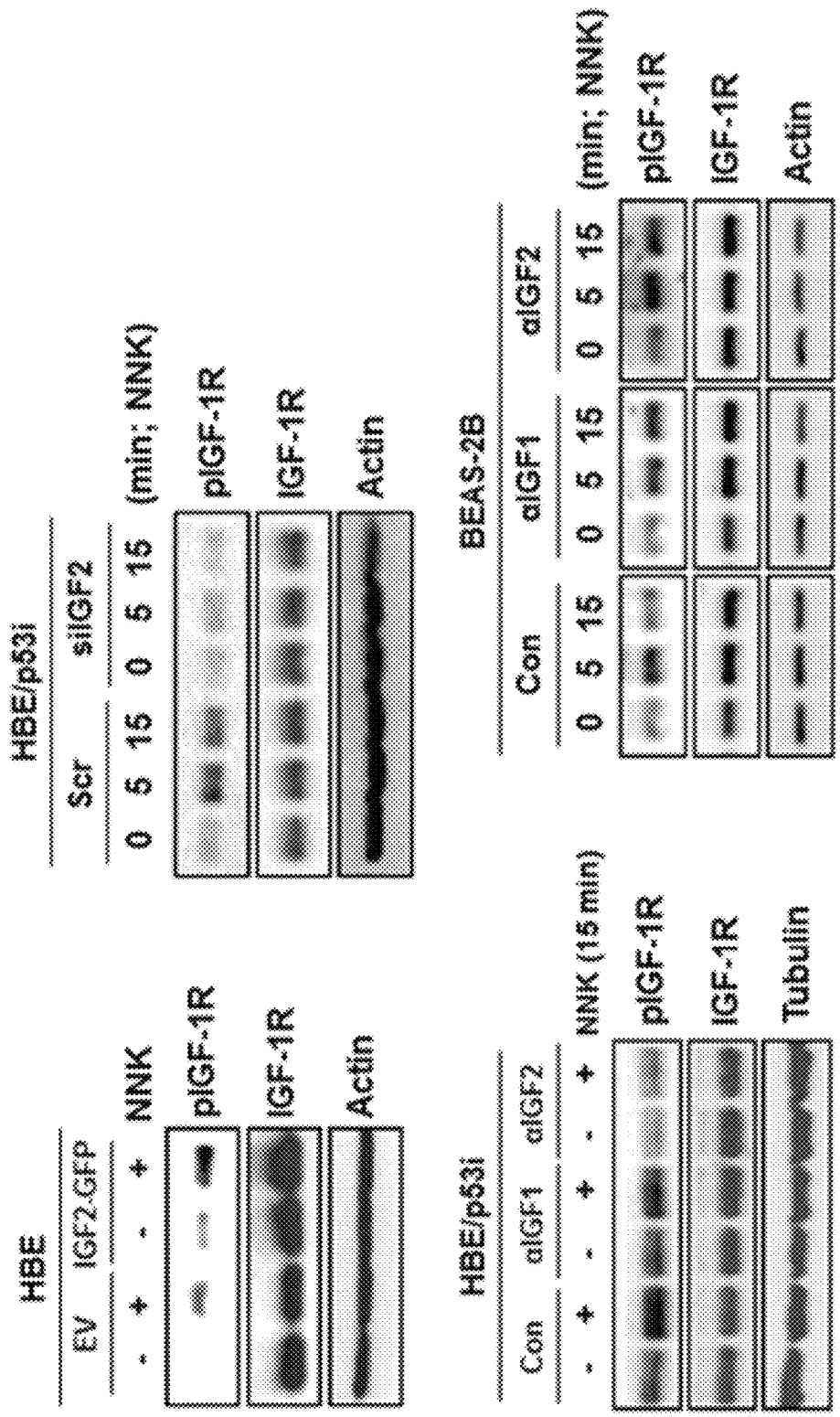
FIG. 8 shows that, based on the result of FIG. 7, when IGF2 expression vectors are introduced, the increase in NNK-induced IGF-1R phosphorylation is accelerated, however, when IGF2 expression is suppressed or secreted IGF2 is eliminated using siRNA or a neutralizing antibody (αIGF2), the increased IGF-1R phosphorylation induced by NNK is attenuated, indicating that the increase in NNK-induced IGF-1R phosphorylation results from promotion of IGF2 production or secretion.

Subsequently, based on the result, with transfection with an IGF2 expression vector, or with siRNA or a neutralizing antibody according to the method described in Example 1-7, the increase in IGF-1R phosphorylation was identified. As a result, as shown in FIG. 8, it was confirmed that, when transfection was carried out with the IGF2 expression vector, the NNK-induced increase in IGF-1R phosphorylation was enhanced, but when IGF2 expression was inhibited or secreted IGF2 was eliminated using the siRNA or neutralizing antibody, the NNK-induced increase in IGF-1R phosphorylation was attenuated. From the result, it can be noted that the NNK-induced increase in IGF-1R phosphorylation results from promotion of IGF2 generation or secretion.

Figure 9:
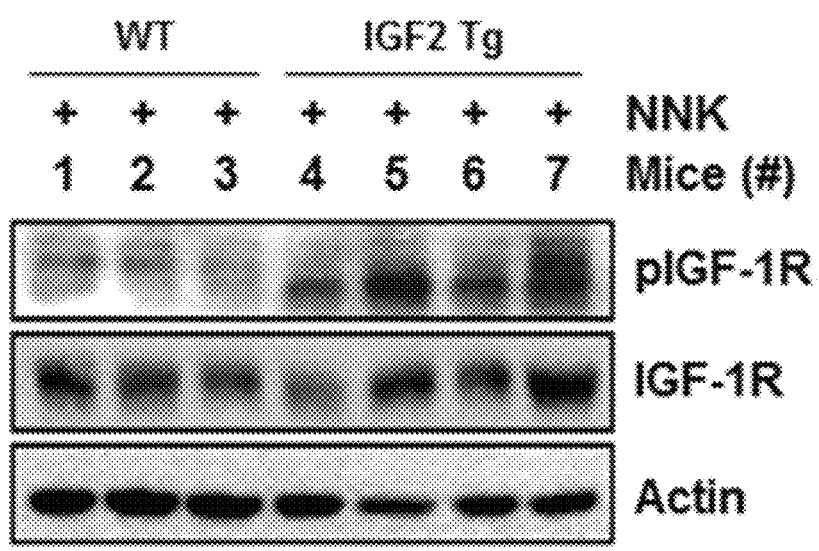
FIG. 9 shows that, compared with wild type mice, IGF-1R phosphorylation is increased in lung tissues from IGF2 transgenic mice carrying lung-specific overexpression of IGF2, obtained after NNK treatment.

Afterward, IGF2 transgenic mice were prepared according to the method described in Example 1-22, and then the IGF2 transgenic mice and wild type mice were each treated with NNK (3 µmol), and lung tissue was extracted therefrom to investigate the increase/decrease in IGF-1R phosphorylation according to the method described in Example 1-10. As a result, as shown in FIG. 9, it was confirmed that, compared to the wild type mice, the IGF-1R phosphorylation was increased by NNK treatment in the IGF2 transgenic mice.

Figure 10:
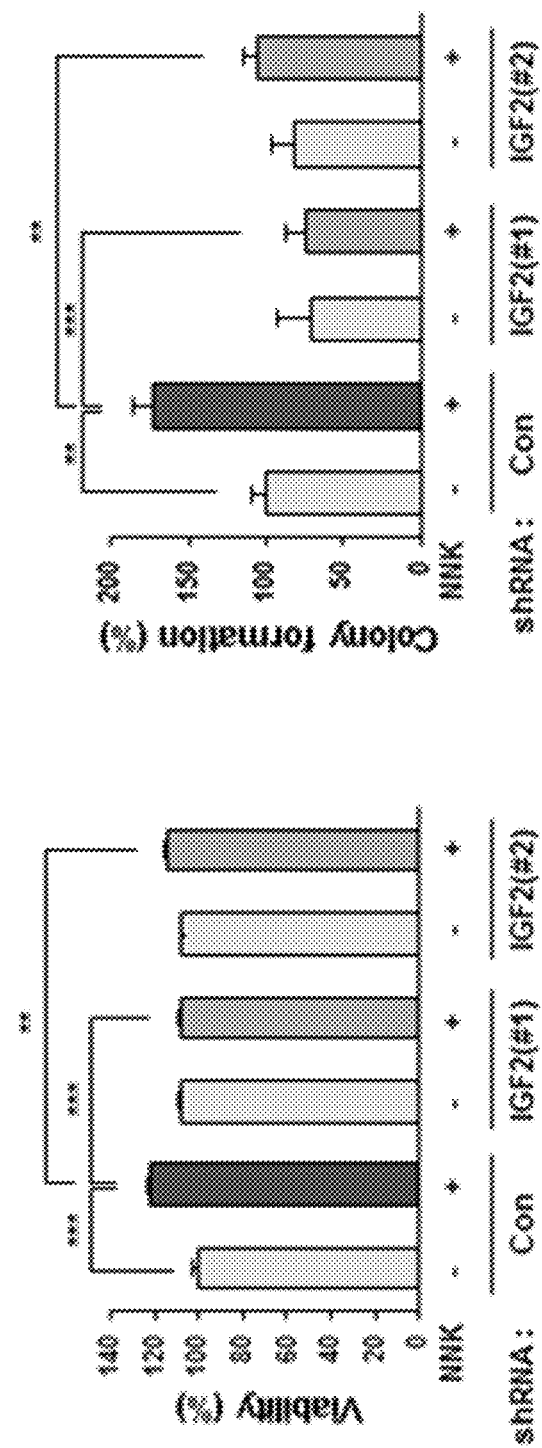
FIG. 10 shows that the increases in NNK-induced viability and colony formation of lung epithelial cells are suppressed by decreased IGF2 expression caused by shRNA transfection, indicating that IGF2 and IGF-1R activation mediated thereby are associated with NNK-induced transformation of lung epithelial cells.

After then, using an IGF2 expression-suppressed cell line established by the method described in Example 1-8, it was investigated whether viability and colony formation of lung epithelial cells were increased or decreased according to the treatment with or without NNK. As a result, as shown in FIG. 10, it was confirmed that the NNK-induced increase in viability and colony formation of lung epithelial cells was inhibited by decreased IGF2 expression. From the result, it was noted that the NNK-induced transformation of lung epithelial cells was associated with IGF2 and IGF-1R activation thereby.

Figure 11:
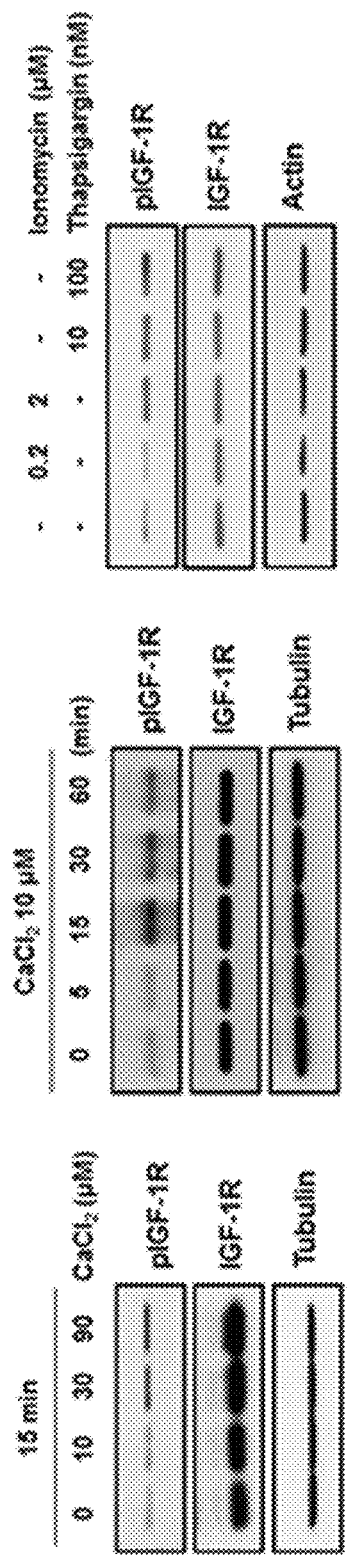
FIG. 11 shows that, when intracellular $Ca^{2+}$ levels are increased by promoting the release of intracellular and extracellular $Ca^{2+}$ into the cytoplasm by the increase in $Ca^{2+}$ concentration or treatment time or the treatment with ionomycin or thapsigargin, IGF-1R phosphorylation is enhanced.

Example 4: Confirmation of Inhibitory Effect of Antihypertensive Drug, Such as Calcium Channel Blockers, on NNK-Mediated Activation of IGF-1R Signaling and Cell Transformation 4-1. Confirmation of Inhibitory Effect of Calcium Channel Blocker on NNK-Mediated Activation of IGF-1R Signaling and Cell Transformation First, after cells (HBE/p53i) were treated with various concentrations of $Ca^{2+}$, or treated with ionomycin or thapsigargin to release intracellular and extracellular $Ca^{2+}$ into the cytoplasm, the increase/decrease in IGF-1R phosphorylation was investigated by the method described in Example 1-10. As a result, as shown in FIG. 11, it was confirmed that, when intracellular $Ca^{2+}$ concentrations were increased, the IGF-1R phosphorylation was increased.

Figure 12:
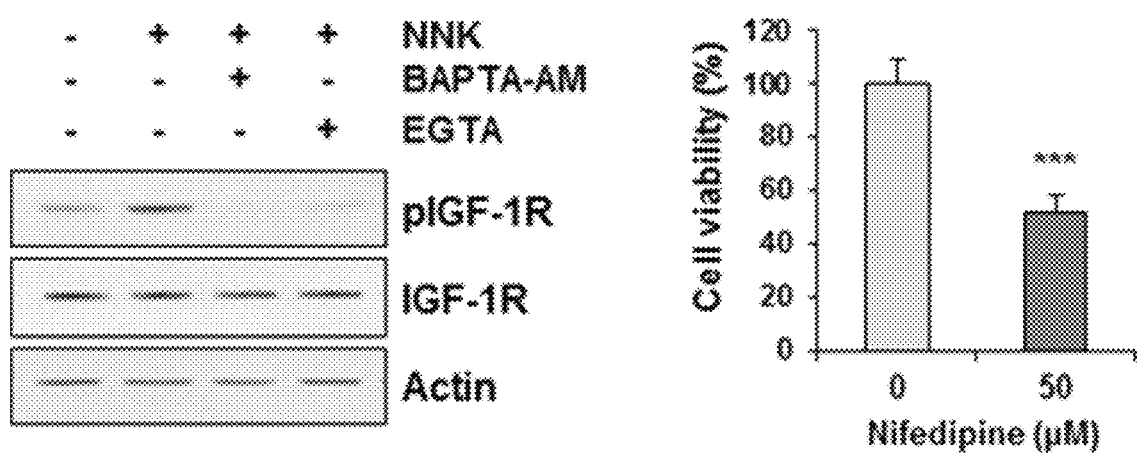
FIG. 12 shows that IGF-1R phosphorylation is suppressed by eliminating $Ca^{2+}$ intracellularly or extracellularly using a $Ca^{2+}$ chelator (EGTA or BAPTA-AM).

Subsequently, the increase/decrease in IGF-1R phosphorylation was investigated by the method described in Example 1-10 after treatment with a $Ca^{2+}$ chelator, such as ethylene glycol tetraacetic acid (EGTA) or 1,2-bis(2-aminophenoxy)ethane-N,N,N',N'-tetraacetic acid tetrakis(acetoxymethyl ester) (BAPTA-AM). As a result, as shown in FIG. 12, it was confirmed that, when the intracellular and extracellular $Ca^{2+}$ were eliminated using the $Ca^{2+}$ chelators, the IGF-1R phosphorylation was inhibited.

Figure 13:
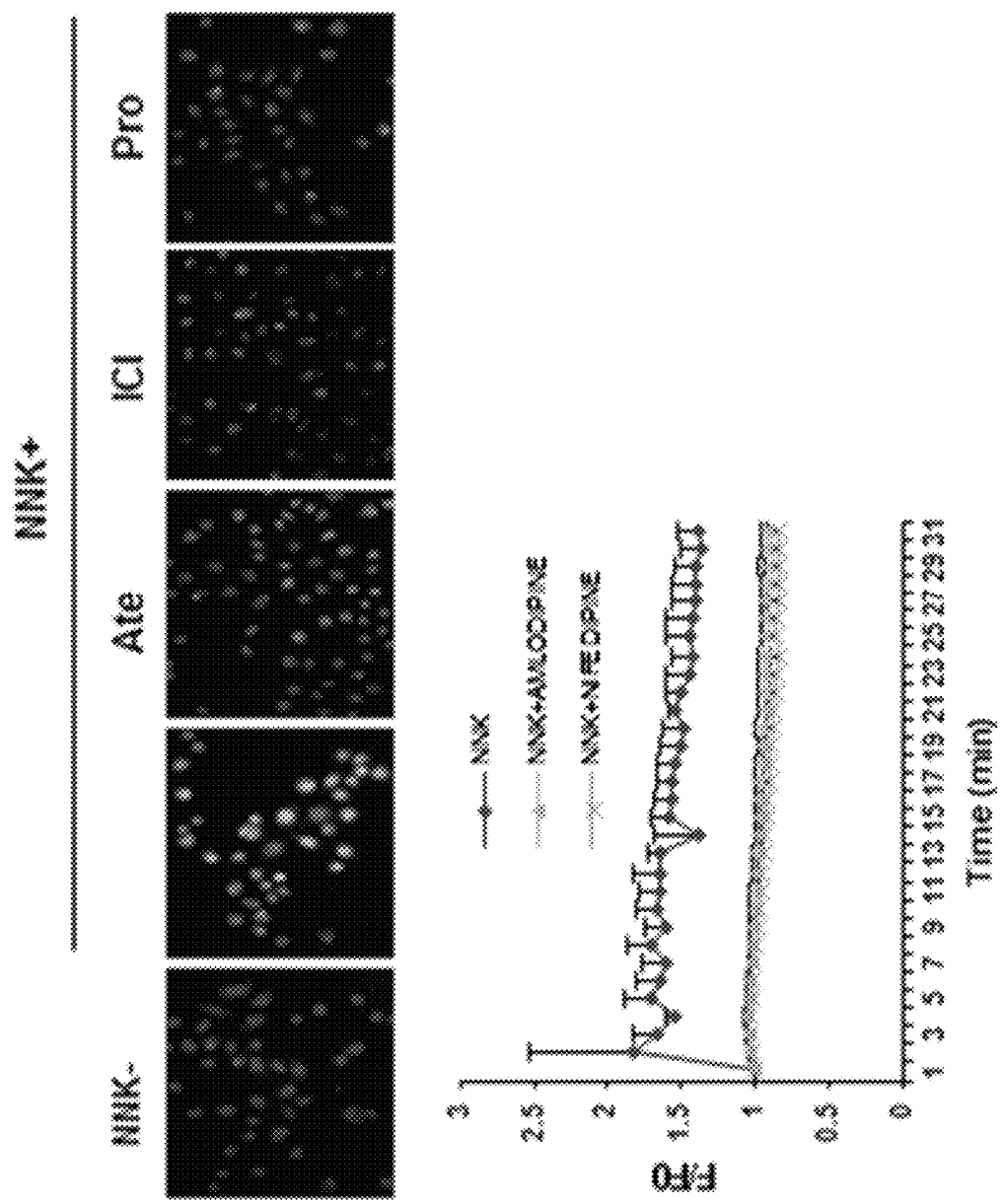
FIG. 13 shows that NNK-induced increases in intracellular $Ca^{2+}$ levels are suppressed by a calcium channel blocker serving as an antihypertensive drug.

In addition, cells were treated with NNK and/or a calcium channel blocker, and the change in intracellular $Ca^{2+}$ generation was investigated according to the method described in Example 1-12. As a result, as shown in FIG. 13, it was confirmed that the intracellular $Ca^{2+}$ was increased by NNK, which is inhibited by an antihypertensive drug, such as a calcium channel blocker.

Figure 14:
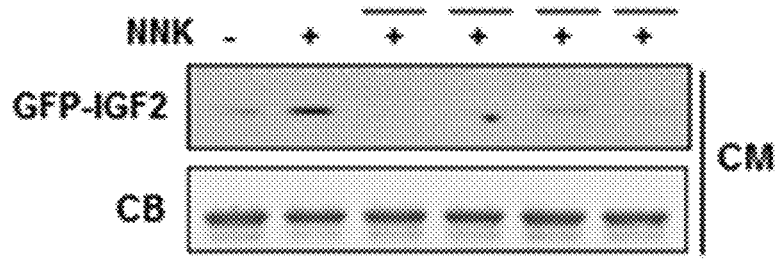
FIG. 14 shows that NNK-induced IGF2 secretion is suppressed by a $Ca^{2+}$ chelator (EGTA or BAPTA-AM), or a calcium channel blocker.
Figure 14:

Afterward, cells (GFP-IGF2-overexpressing BEAS-2B) were treated with NNK and/or a calcium channel blocker, and the change in IGF2 secretion was investigated according to the method described in Example 1-10. As a result, as shown in FIG. 14, it was confirmed that the IGF2 secretion was increased by NNK, which is inhibited by the $Ca^{2+}$ chelator, such as EGTA or BAPTA-AM, or calcium channel blockers.

Figure 15:
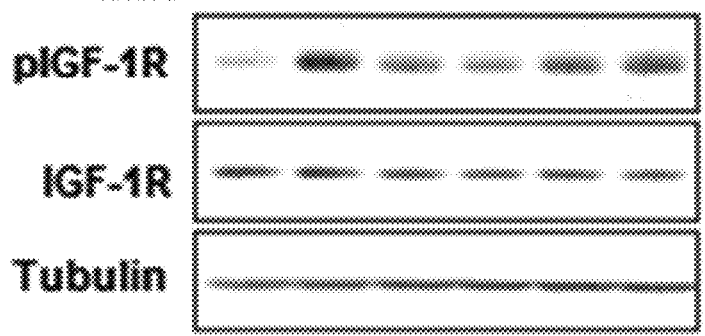
FIG. 15 shows that NNK-induced IGF-1R activation is suppressed by a calcium channel blocker.

Then, cells (HBE/p53i) were concentration-dependently treated with NNK and/or various calcium channel blockers, and the change in IGF-1R activation was investigated according to the method described in Example 1-10. As a result, as shown in FIG. 15, it was confirmed that the NNK-induced IGF-1R activation was inhibited by a calcium channel blocker.

Figure 16:
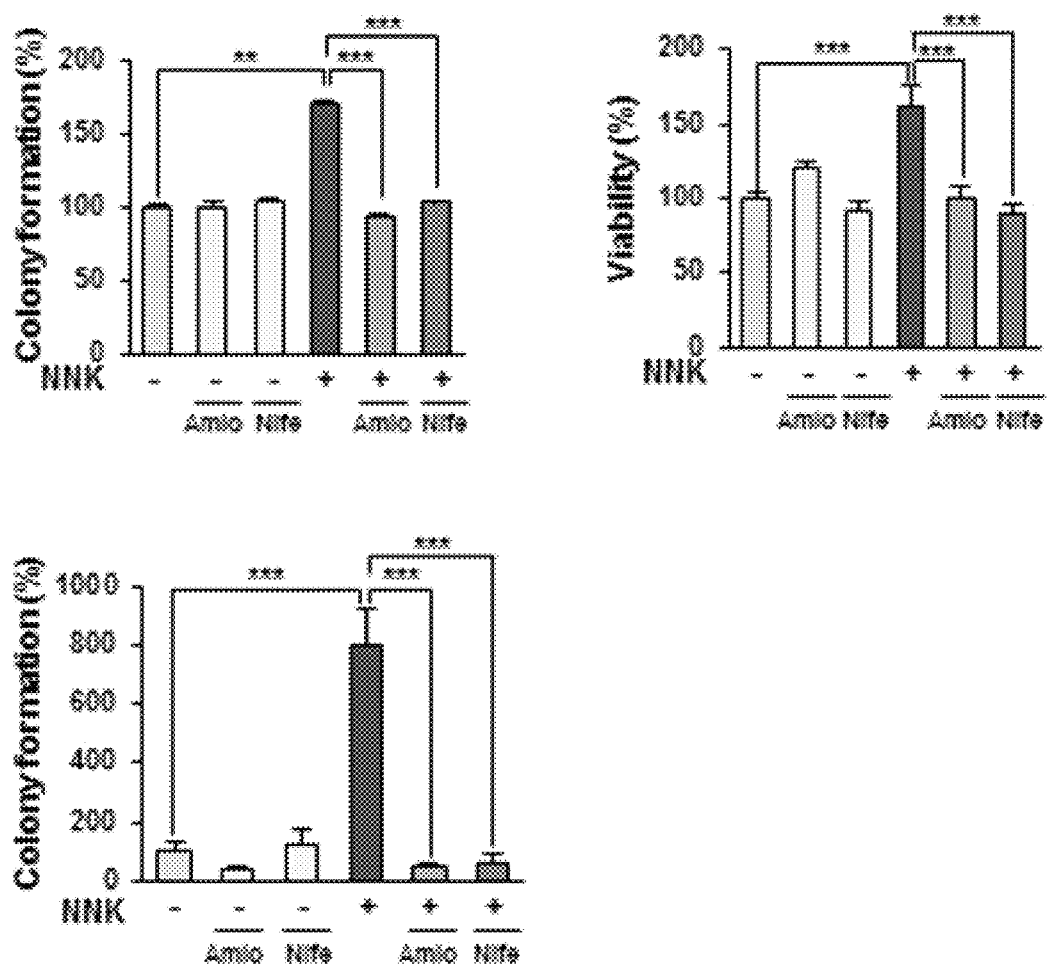
FIG. 16 shows that the NNK-induced increases in viability and colony formation of lung epithelial cells are suppressed by a calcium channel blocker, thereby blocking NNK-induced transformation of lung epithelial cells.

Example 5: Confirmation of Inhibitory Effect of an Antihypertensive Drug Such as a Calcium Channel Blocker on NNK-Induced Tumorigenesis First, it was investigated whether NNK-induced increases in viability, colony formation, and foci formation in lung epithelial cells were changed by calcium channel blocker according to the methods described in Examples 1-4, 1-5 and 1-6. As a result, as shown in FIG. 16, the NNK-induced increases in viability, colony formation and foci formation in lung epithelial cells was inhibited by calcium channel blockers, and from the above result, it was noted that a calcium channel blocker blocked the NNK-induced transformation of lung epithelial cells.

Figure 17:
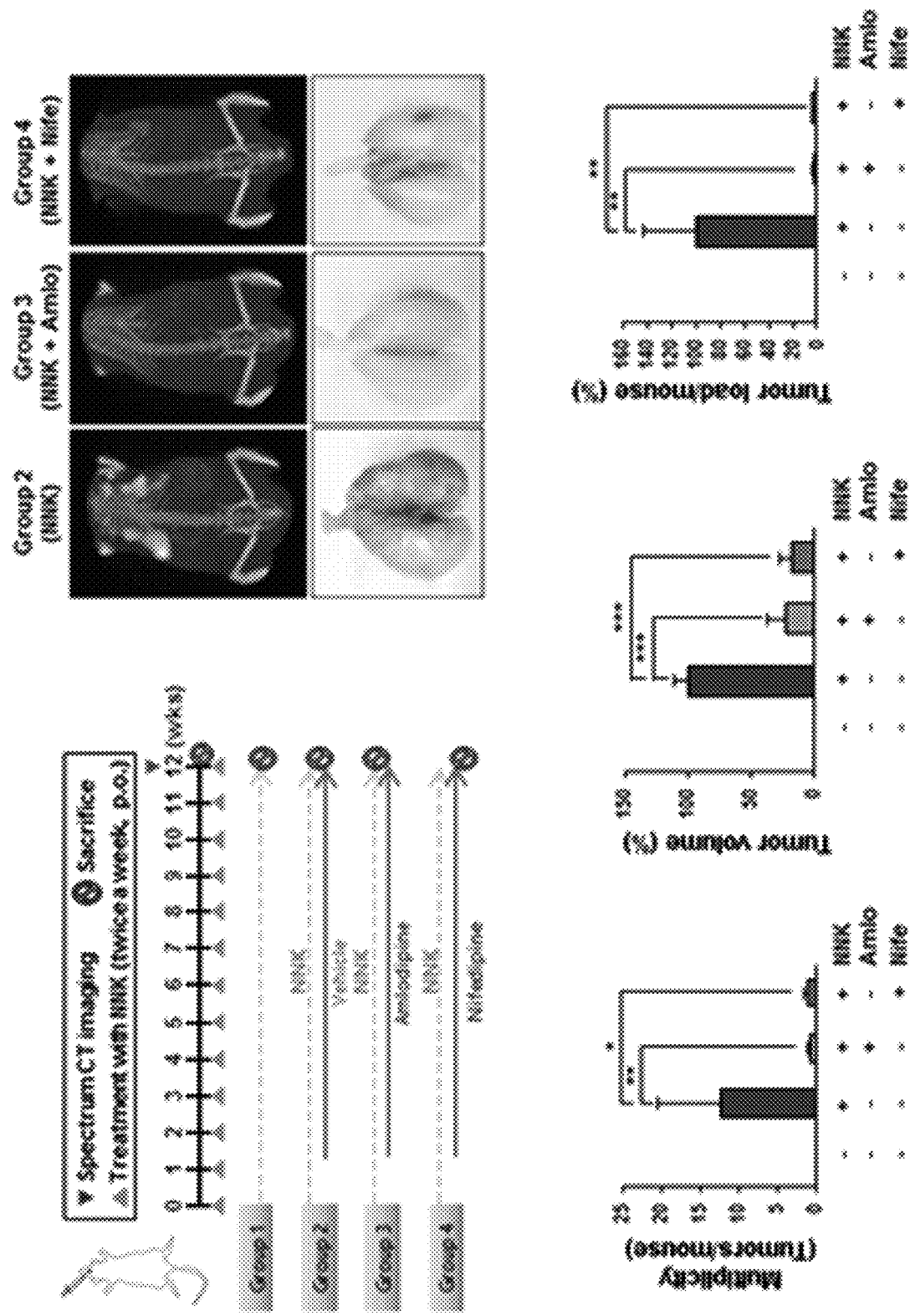
FIG. 17 shows that NNK-induced tumorigenesis is suppressed by a calcium channel blocker, indicating a preventive effect of a calcium channel blocker on lung carcinogenesis resulting from smoking.

Subsequently, a tumorigenesis inhibitory effect of a calcium channel blocker in lung carcinogenesis animal models was investigated according to the method described in Example 1-17. As a result, as shown in FIG. 17, it was confirmed that NNK-induced tumorigenesis was significantly suppressed by treatment with calcium channel blockers.

Figure 18:
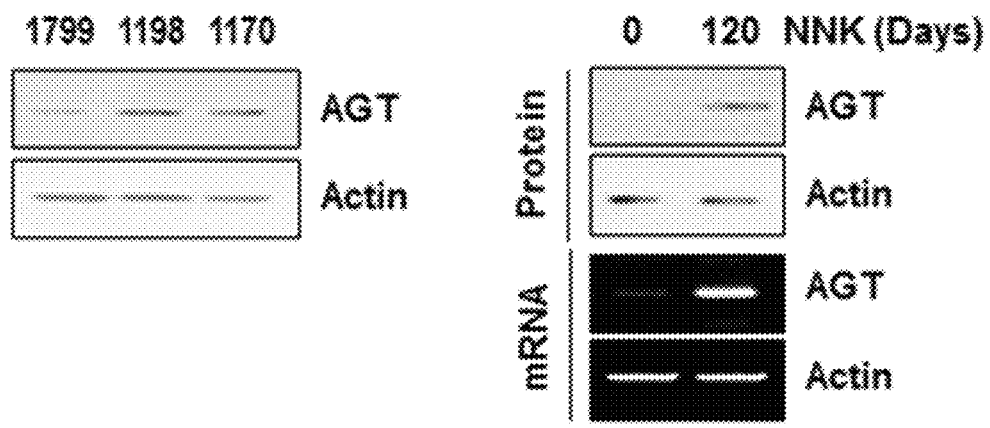
FIG. 18 shows that the expression of angiotensinogen (AGT), which is an angiotensin precursor, is increased in premalignant lung epithelial cells (1198) and malignant lung epithelial cells (1170), derived from a tumor generated after 6 months of treatment of a tobacco carcinogen, and lung epithelial cells treated with NNK for 120 days.

Example 6: Confirmation of Activation of IGF-1R Signaling Mediated by Increased Angiotensinogen (AGT) Expression Due to Tobacco-Derived Carcinogen in Lung Epithelial Cells First, it was investigated whether the expression of a precursor of angiotensin, AGT, was changed in premalignant lung epithelial cells (1198) and malignant lung epithelial cells (1170), derived from a tumor generated by treatment with a tobacco carcinogen for 6 months, and lung epithelial cells treated with NNK for 120 days according to the method described in Example 1-10. As a result, as shown in FIG. 18, it was confirmed that the AGT expression was increased by treatment with the tobacco carcinogen NNK.

Figure 19:
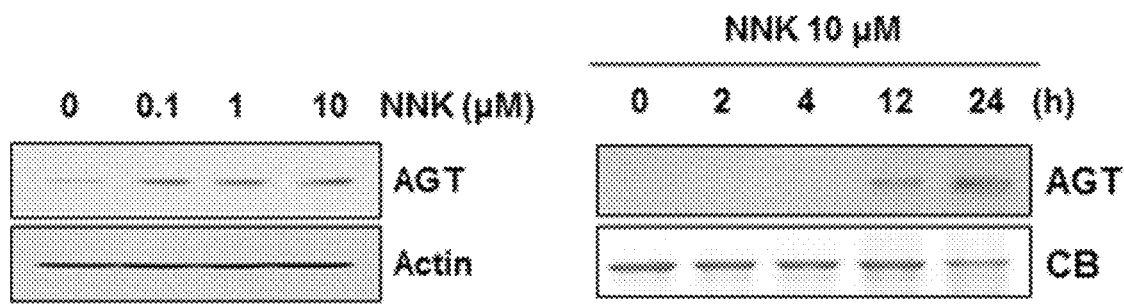
FIG. 19 shows that AGT expression or secretion is dependent on the increases in NNK treatment time and concentration.
Figure 20:
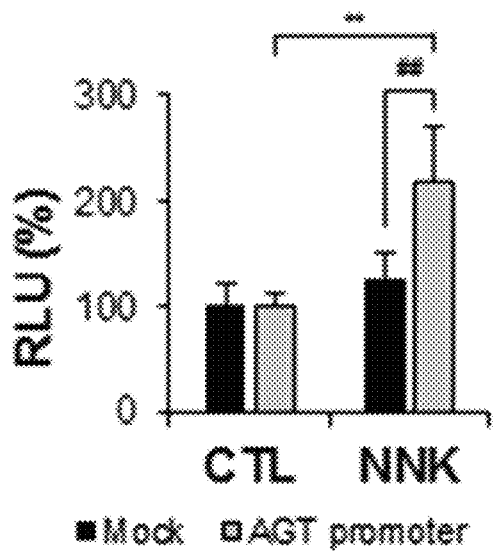
FIG. 20 shows that an AGT promoter is activated by NNK treatment.

Subsequently, NNK treatment time- and concentration-dependent changes in AGT expression or secretion were investigated according to the method described in Example 1-10. As a result, as shown in FIGS. 19 and 20, according to the increase in NNK treatment time and concentration, the AGT expression and secretion were increased, and an AGT promoter was activated.

Figure 21:
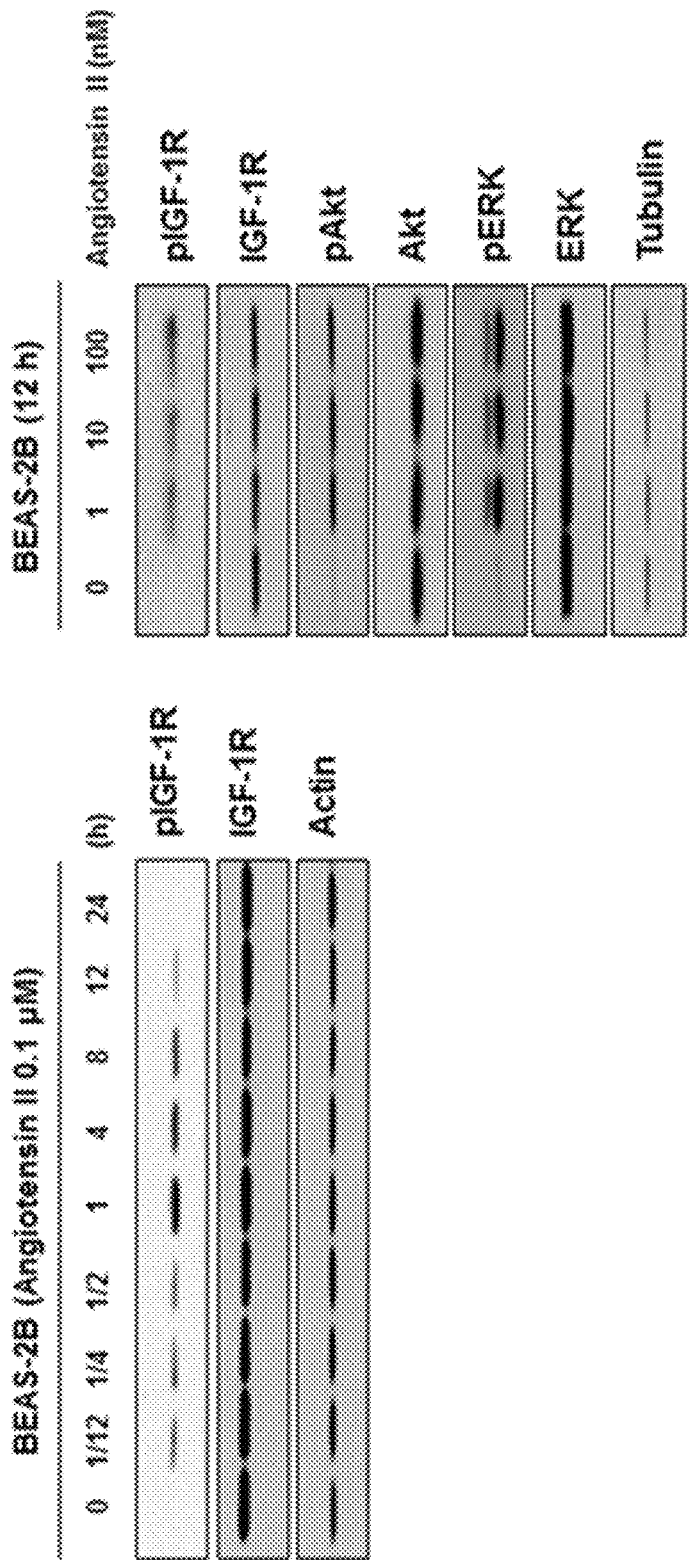
FIG. 21 shows concentration- and time-dependent activation of IGF-1R and their downstream signaling mediators Akt and ERK, induced by angiotensin.

Afterward, lung epithelial cells (BEAS-2B) were treated with angiotensin, and whether the activation of IGF-1R and downstream signaling thereof was changed was investigated according to the method described in Example 1-10. As a result, as shown in FIG. 21, it was confirmed that the IGF-1R

Figure 22:
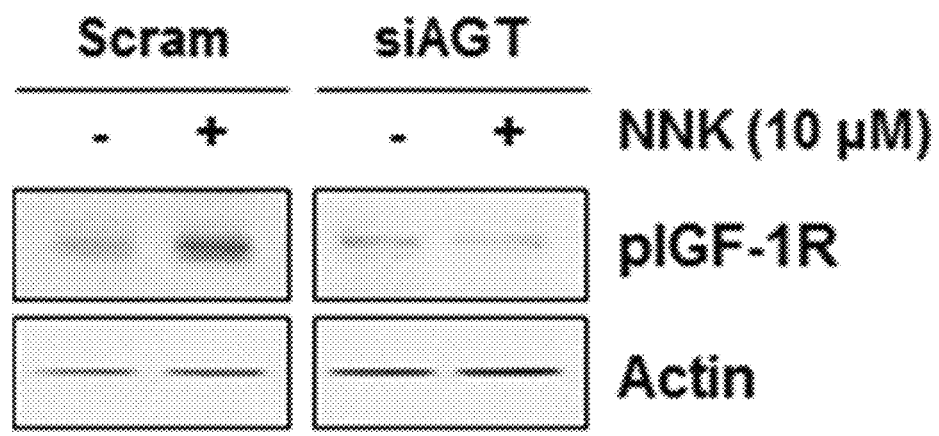
FIG. 22 shows that, when the expression of an angiotensin receptor is ablated by siRNA transfection, NNK-induced IGF-1R activation is suppressed.

Example 7: Confirmation of Inhibitory Effects of an Angiotensin Transferase Inhibitor and an Angiotensin Receptor Antagonist, Used as Antihypertensive Drugs, on NNK-Mediated Activation of IGF-1R Signaling, Cell Transformation, and Lung Carcinogenesis First, to investigate whether IGF-1R activation was changed according to the inhibition of angiotensin receptor expression, angiotensin receptor expression was inhibited using siRNA in NNK-treated cells (BEAS-2B), and the change in IGF-1R activation was investigated according to the method described in Example 1-10. As a result, as shown in FIG. 22, it was confirmed that when the angiotensin receptor expression was inhibited, NNK-mediated IGF-1R activation was inhibited.

Figure 23:
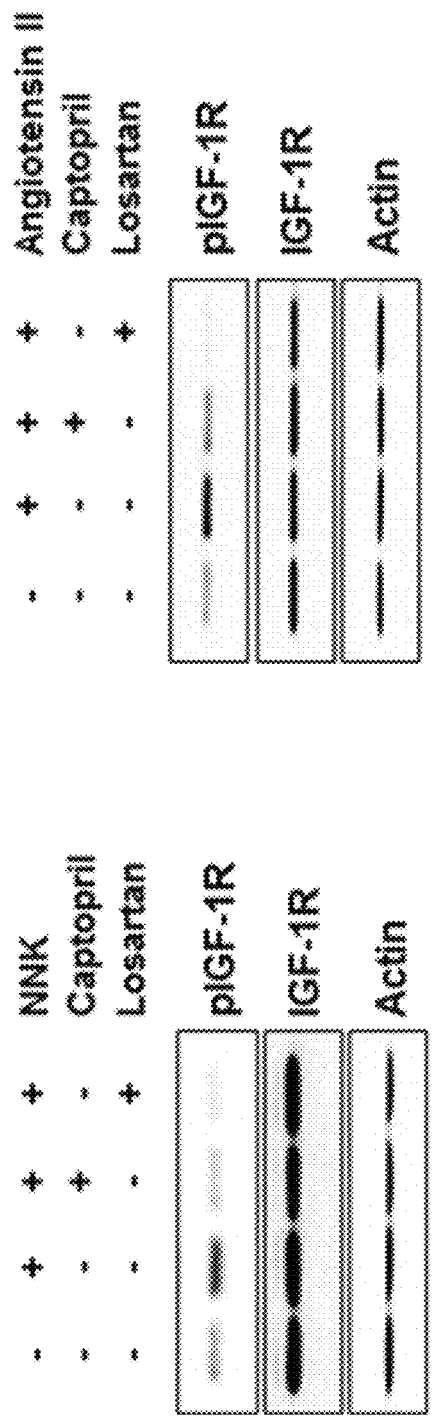
FIG. 23 shows that NNK-induced IGF-1R activation is suppressed by treatment with captopril, which is an angiotensin-converting enzyme inhibitor serving as an antihypertensive drug, and losartan, which is an angiotensin receptor antagonist.

Subsequently, NNK-treated cells (BEAS-2B) were treated with an angiotensin-converting enzyme inhibitor such as captopril and/or an angiotensin receptor antagonist such as losartan, the change in IGF-1R activation was investigated according to the method described in Example 1-10. As a result, as shown in FIG. 23, it was confirmed that the NNK-mediated IGF-1R activation was inhibited by treatment with the angiotensin-converting enzyme inhibitor (captopril) or angiotensin receptor antagonist (losartan).

Figure 24:
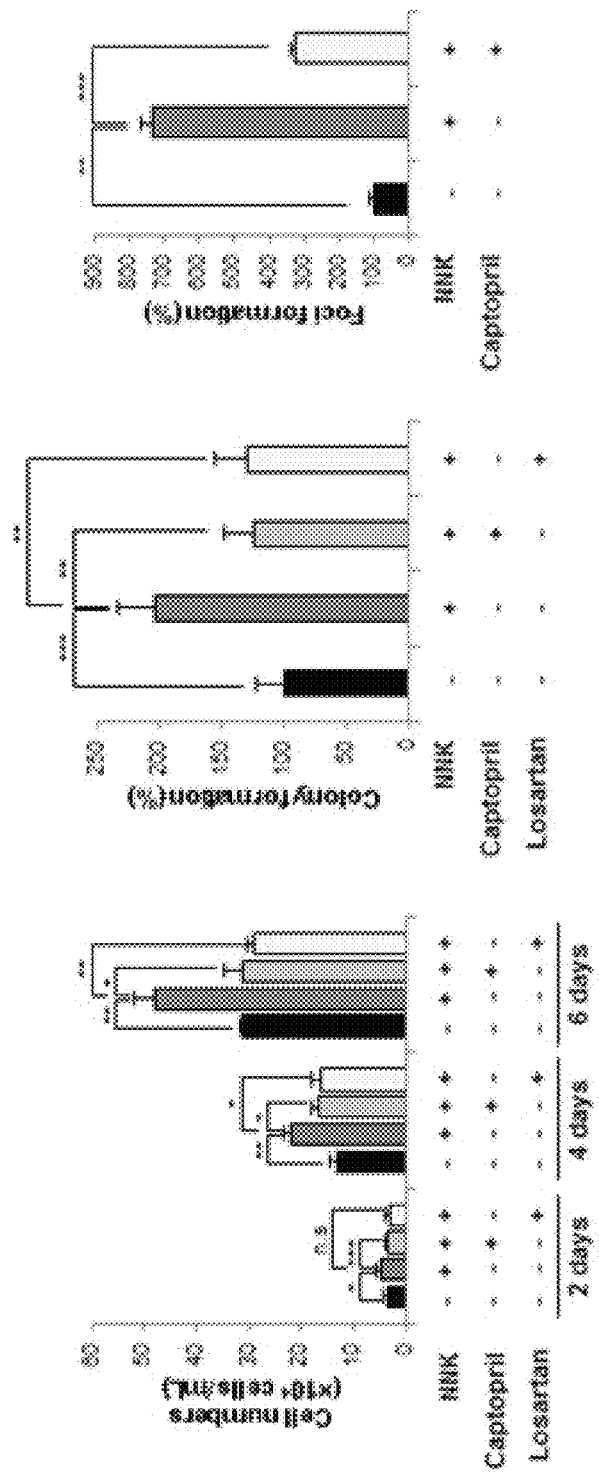
FIG. 24 shows that NNK-induced promotion of cell viability, colony formation, and foci formation is suppressed by an angiotensin-converting enzyme inhibitor and an angiotensin receptor antagonist.
Figure 25:
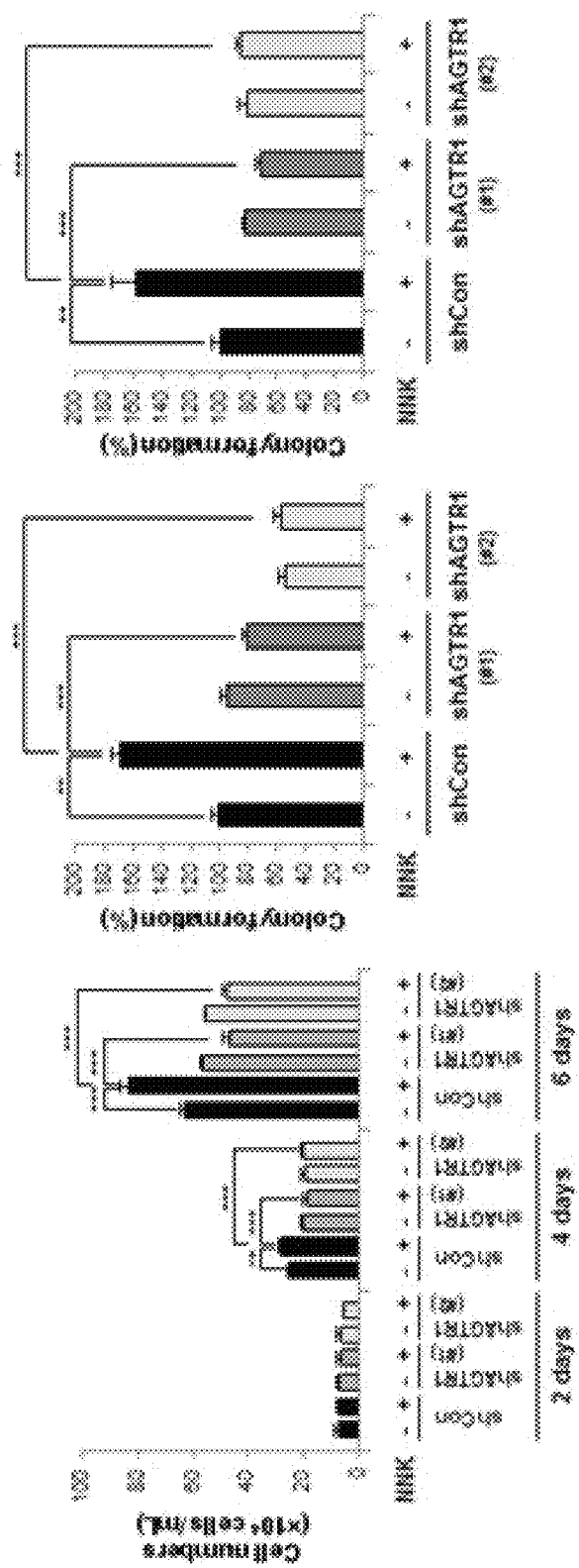
FIG. 25 shows that, when the expression of an angiotensin receptor is suppressed by shRNA transfection, NNK-induced promotion of cell viability, colony formation, and foci formation is suppressed.

Afterward, the angiotensin receptor expression was suppressed by treatment with the angiotensin-converting enzyme inhibitor (captopril) or angiotensin receptor antagonist (losartan) or shRNA transfection, and the changes in NNK-induced promotion of cell viability, colony formation and foci formation were investigated according to the methods described in Examples 1-4, 1-5 and 1-6. As a result, as shown in FIGS. 24 and 25, when the angiotensin-converting enzyme inhibitor (captopril) or angiotensin receptor antagonist (losartan) was treated, or the angiotensin receptor expression was inhibited, it was confirmed that NNK-induced promotion of cell viability, colony formation and foci formation was suppressed.

Figure 26:
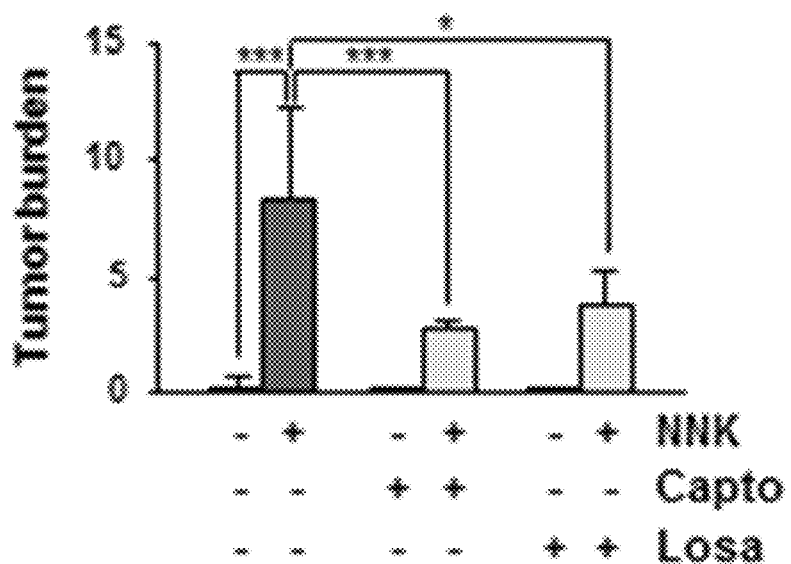
FIG. 26 shows that NNK-induced tumorigenesis is suppressed by an angiotensin-converting enzyme inhibitor or an angiotensin receptor antagonist, indicating a preventive effect of these drugs on lung carcinogenesis caused by smoking.

Moreover, a tumorigenesis inhibitory effect of the angiotensin-converting enzyme inhibitor (captopril) or angiotensin receptor antagonist (losartan) in lung carcinogenesis animal models was investigated according to the method described in Example 1-17. As a result, as shown in FIG. 26, it was confirmed that NNK-induced tumorigenesis was significantly suppressed by treatment with antihypertensive drugs (an angiotensin-converting enzyme inhibitor or an angiotensin receptor antagonist).

Figure 27:
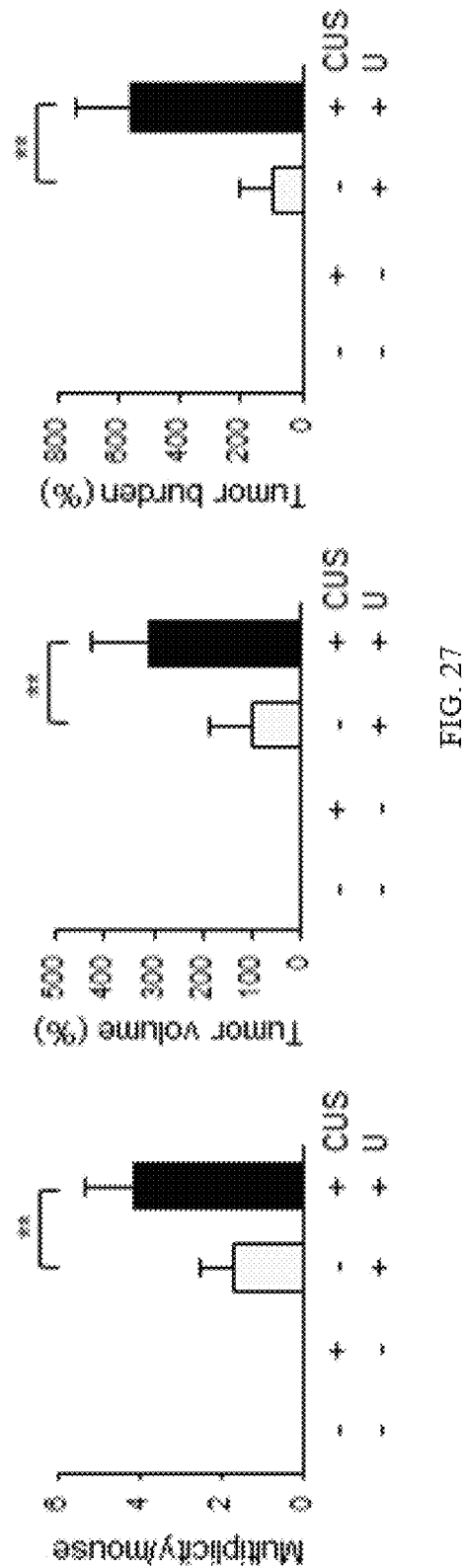
FIG. 27 shows that urethane-initiated lung carcinogenesis is significantly increased by stress exposure in mice.
Figure 28:
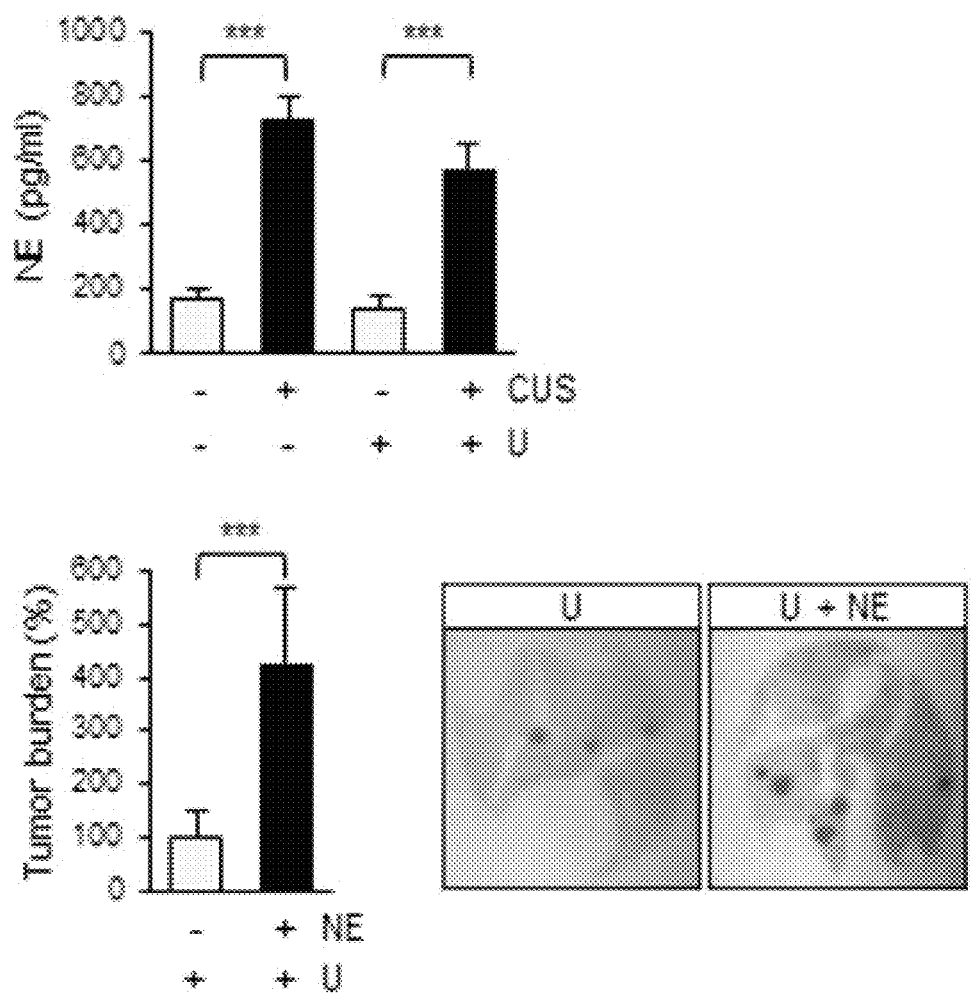
FIG. 28 shows that a blood concentration of NE, which is a stress hormone, is increased by stress exposure, and urethane-initiated lung carcinogenesis is also significantly increased by continuous NE exposure.

Example 8: Confirmation of Promotion of Cell Transformation and Promotion of Carcinogen-Induced Tumorigenesis and IGF-1R Signaling Activation, Caused by Stress and a Stress Hormone First, a direct increase in carcinogenesis caused by exposure to stress and promotion of urethane-induced carcinogenesis by stress in animal models were evaluated according to the method described in Example 1-16. As a result, as shown in FIG. 27, it was confirmed that urethane-initiated lung carcinogenesis was significantly increased. In addition, as the result of detecting the blood concentration of a stress hormone NE, as shown in FIG. 28, it was confirmed that the blood concentration of the stress hormone NE was increased by stress exposure, and in the same manner, the urethane-initiated lung carcinogenesis was also significantly increased by continuous NE exposure.

Figure 29:
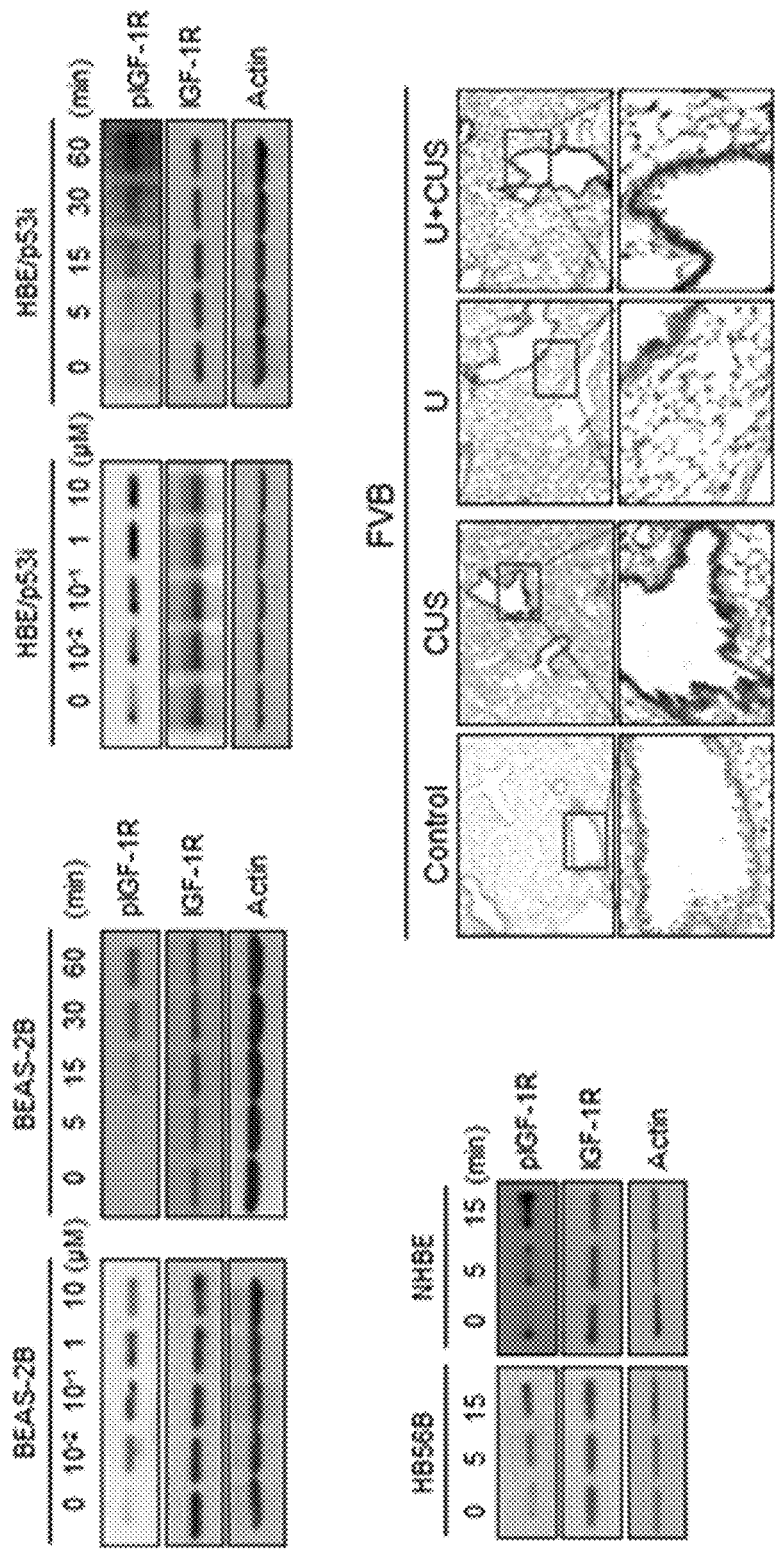
FIG. 29 shows that IGF-1R phosphorylation is increased in various lung epithelial cells and mouse lung tissues exposed to stress, treated with NE time- and concentration-dependently.

Subsequently, lung epithelial cells (BEAS-2B, HBE/p53i, NHBE and HB56B) were time—or concentration dependently treated with NE, and the increase/decrease in IGF-1R phosphorylation was investigated according to the method described in Example 1-10. As a result, as shown in FIG. 29, it was confirmed that IGF-1R phosphorylation was increased by the NE treatment. In addition, it was confirmed that the increase/decrease in IGF-1R phosphorylation in mouse lung tissue exposed to stress according to the method described in Example 1-16 was identified according to the method described in Example 1-18. As a result, as shown in FIG. 29, it was confirmed that the IGF-1R phosphorylation was increased even in the mouse lung tissues exposed to stress.

Figure 30:
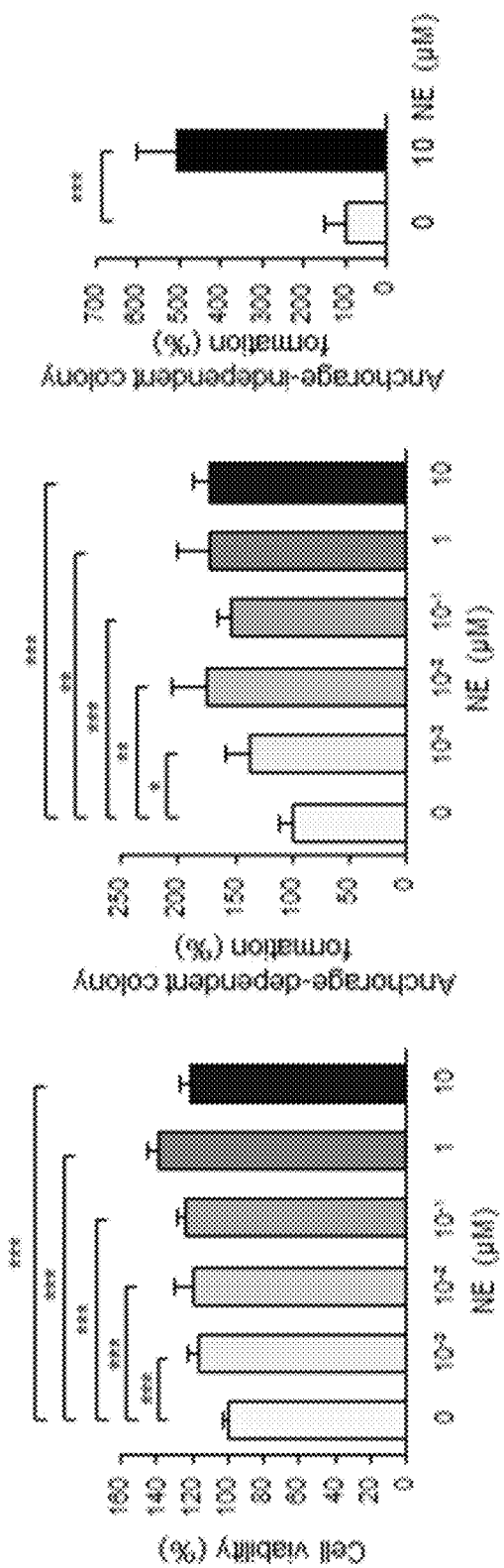
FIG. 30 shows that the increases in transformation, that is, viability, colony formation, and foci formation of lung epithelial cells are significantly boosted by NE.

Afterward, it was investigated whether transformation of lung epithelial cells was changed by the NE treatment according to the methods described in Examples 1-4, 1-5 and 1-6. As a result, as shown in FIG. 30, it was confirmed that the increase in transformation, that is, viability, colony formation, and foci formation of lung epithelial cells was significantly enhanced by NE.

Figure 31:
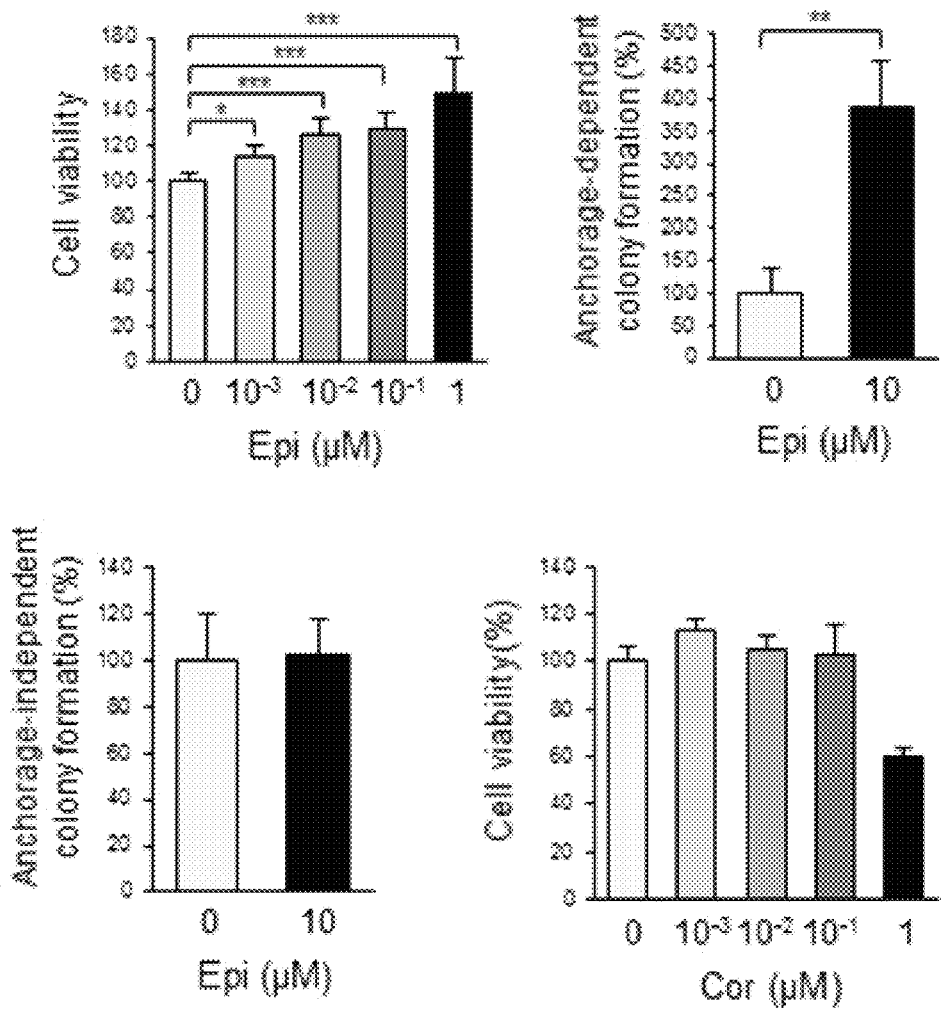
FIG. 31 shows that transformation of lung epithelial cells is induced by epinephrine (Epi), which is an NE-like stress hormone, not by cortisol (Cor).

Moreover, it was investigated whether transformation of lung epithelial cells was also induced by treatment with an NE-like stress hormone such as epinephrine (Epi) or cortisol (Cor). As a result, as shown in FIG. 31, it was confirmed that transformation of lung epithelial cells was induced by epinephrine, not by cortisol.

Figure 32:
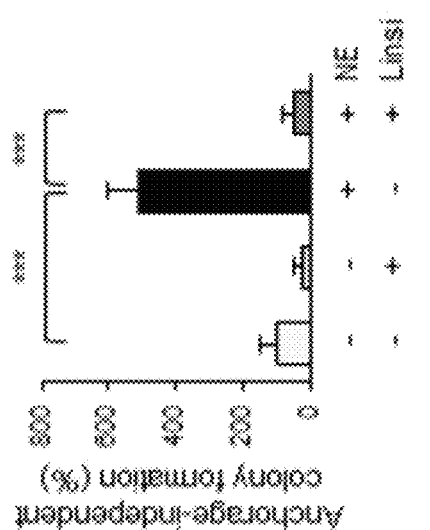
FIG. 32 shows that the NE-induced increases in viability and colony formation of lung epithelial cells are significantly suppressed by linsitinib (Linsi), which is an IGF-1R inhibitor, indicating that induction of the NE-induced transformation of lung epithelial cells is associated with IGF-1R activation.
Figure 32:
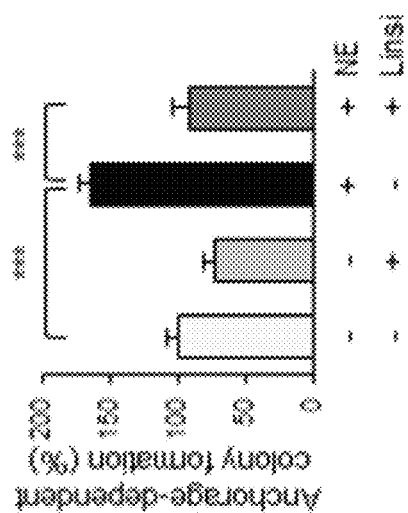
Figure 32:
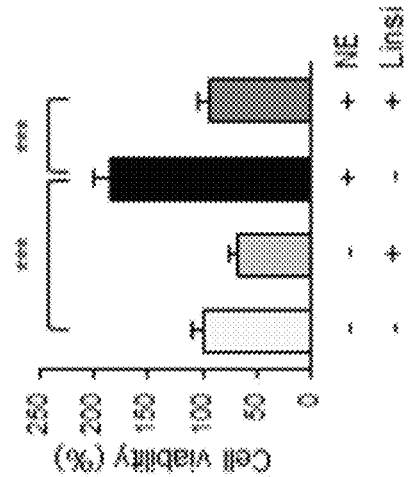

And then, NE-treated lung epithelial cells were treated with an IGF-1R inhibitor such as linsitinib (Linsi), and the change in the transformation of lung epithelial cells was investigated. As a result, as shown in FIG. 32, it was confirmed that the NE-induced increase in viability and colony formation of lung epithelial cells was significantly suppressed by linsitinib. From the result, it was noted that the NE-induced lung epithelial cell transformation was associated with the IGF-1R activation.

Figure 33:
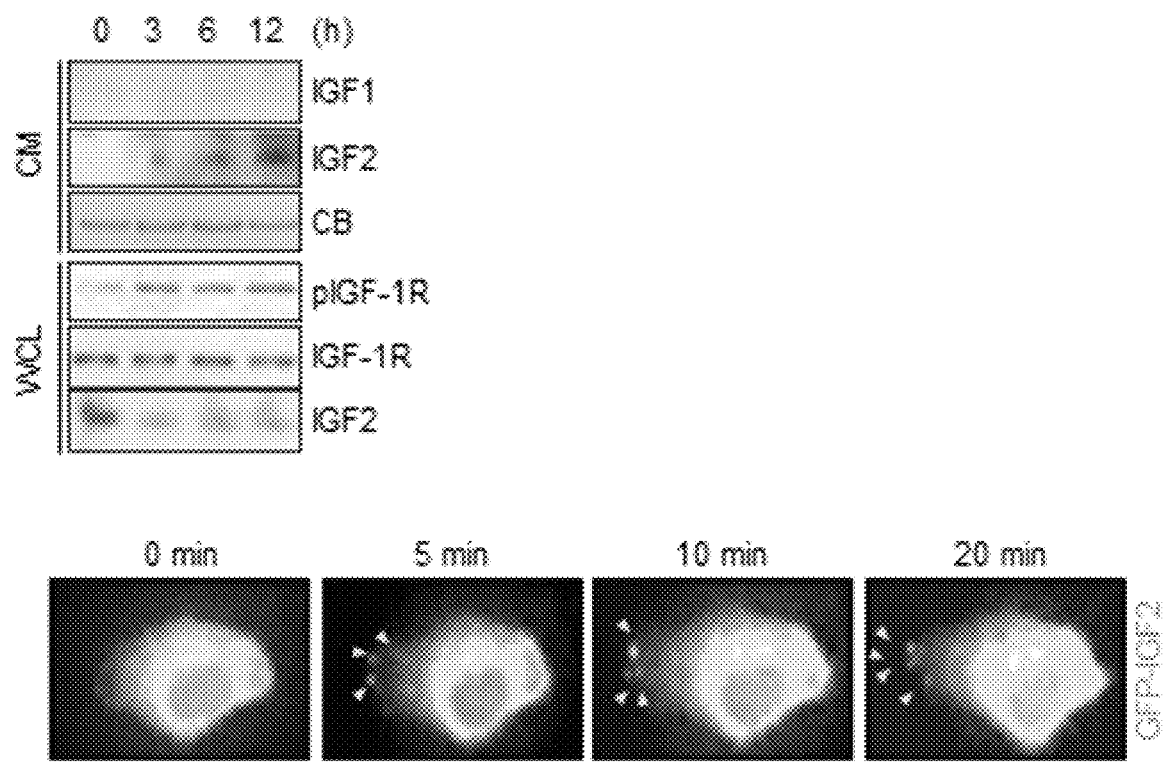
FIG. 33 shows an NE-induced increase in IGF2 secretion.

In addition, lung epithelial cells were treated with NE, and it was investigated whether IGF2 secretion was changed. As a result, as shown in FIG. 33, it was confirmed that the IGF2 secretion was increased by the NE treatment.

Figure 34:
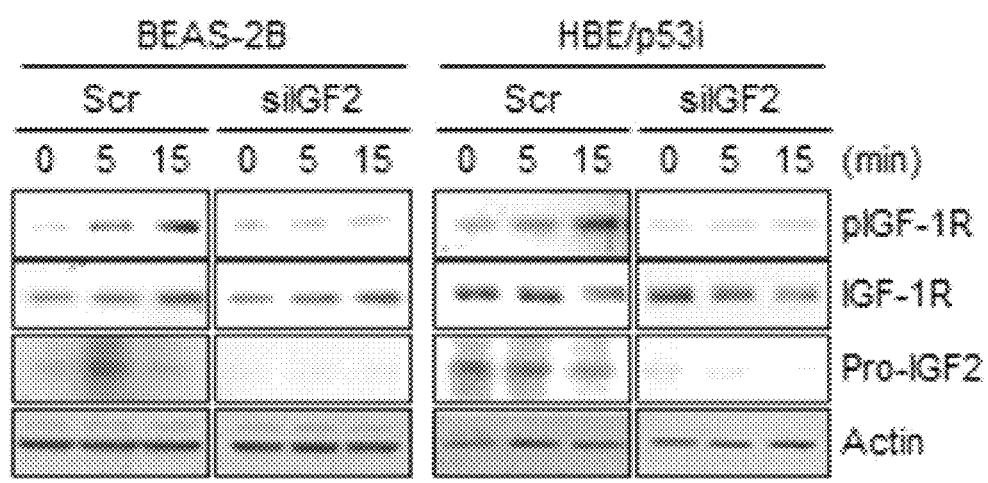
FIG. 34 shows that, when IGF2 expression is suppressed or secreted IGF2 is eliminated by siRNA or a neutralizing antibody (αIGF2), an NE-induced increase in IGF-1R phosphorylation is suppressed, indicating that an NNK-induced increase in IGF-1R phosphorylation results from promotion of IGF2 generation or secretion.
Figure 34:
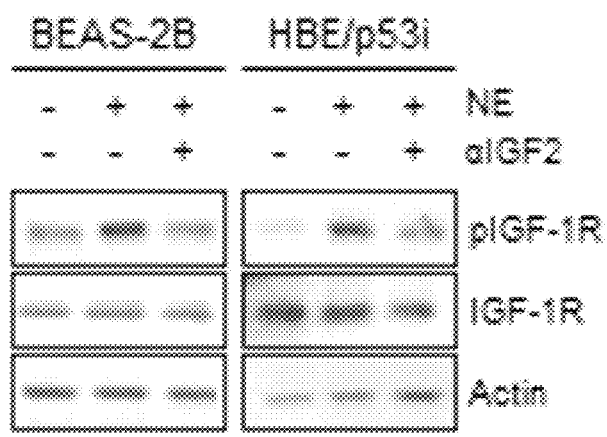

In addition, it was investigated whether IGF-1R phosphorylation was increased when IGF2 expression was inhibited or secreted IGF2 was eliminated using siRNA or a neutralizing antibody, according to the method described in Example 1-7. As a result, as shown in FIG. 34, it was confirmed that, when the IGF2 expression was inhibited or secreted IGF2 was eliminated, the NE-induced increase in IGF-1R phosphorylation was inhibited.

Figure 35:
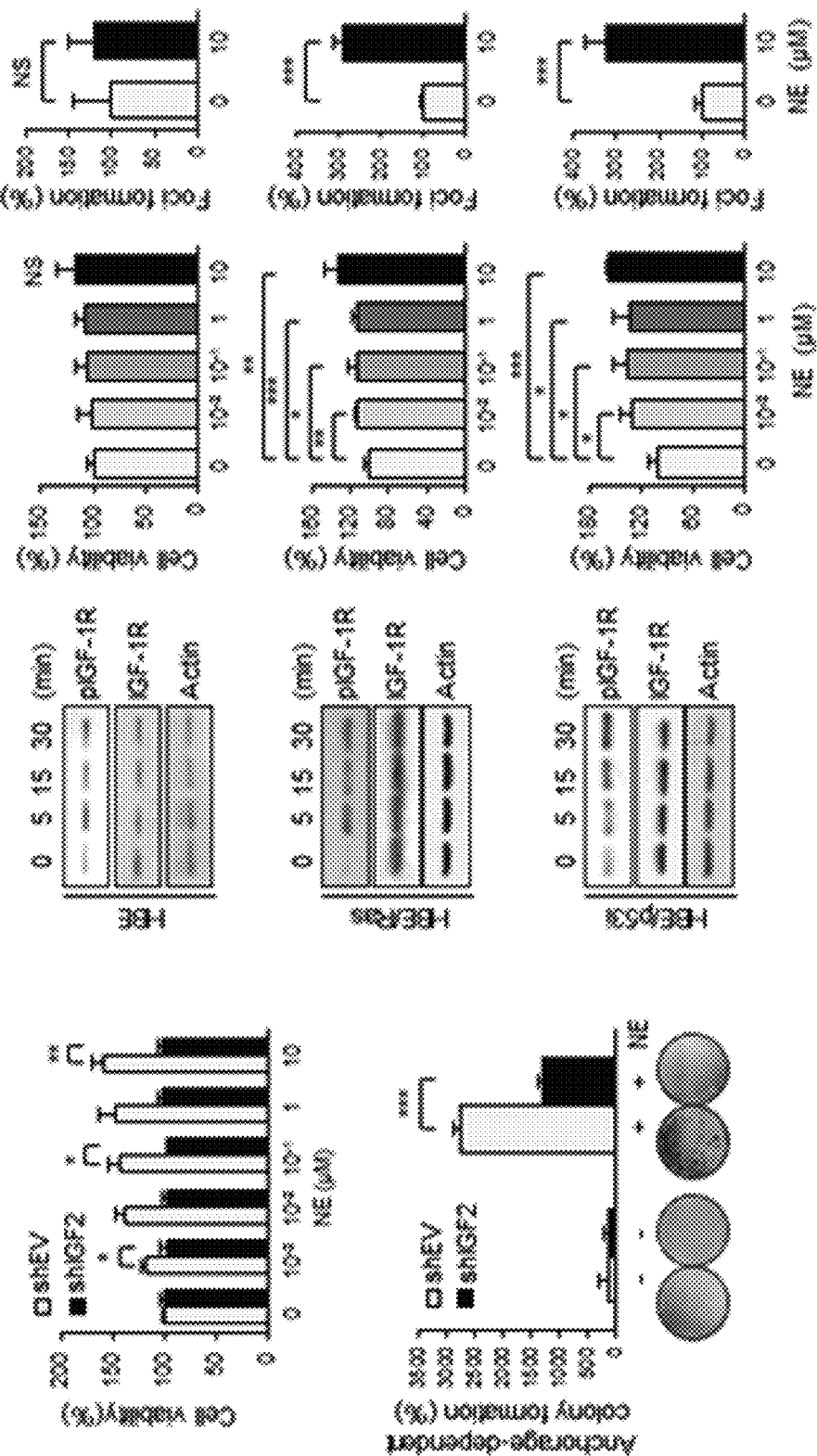
FIG. 35 shows that NE-induced increases in viability and colony formation of lung epithelial cells are suppressed by reduced IGF2 expression, and NE-induced IGF-1R phosphorylation and transformation of lung epithelial cells are noticeably increased in lung epithelial cells showing high levels of basal IGF2 expression, indicating that NE induction of transformation of lung epithelial cells is associated with IGF2 and IGF-1R activation thereby.

In addition, it was investigated whether transformation of lung epithelial cells was changed by NE treatment in IGF2 expression-suppressed cells. As a result, as shown in FIG. 35, it was confirmed that the NE-induced increase in viability and colony formation of lung epithelial cells was inhibited by decreased IGF2 expression. Meanwhile, it was confirmed that NE-induced IGF-1R phosphorylation and transformation of lung epithelial cells were noticeably increased in lung epithelial cells showing high basal expression of IGF2. From the result, it was noted that the NE-induced transformation of lung epithelial cells was associated with IGF2 and IGF-1R activation thereby.

Figure 36:
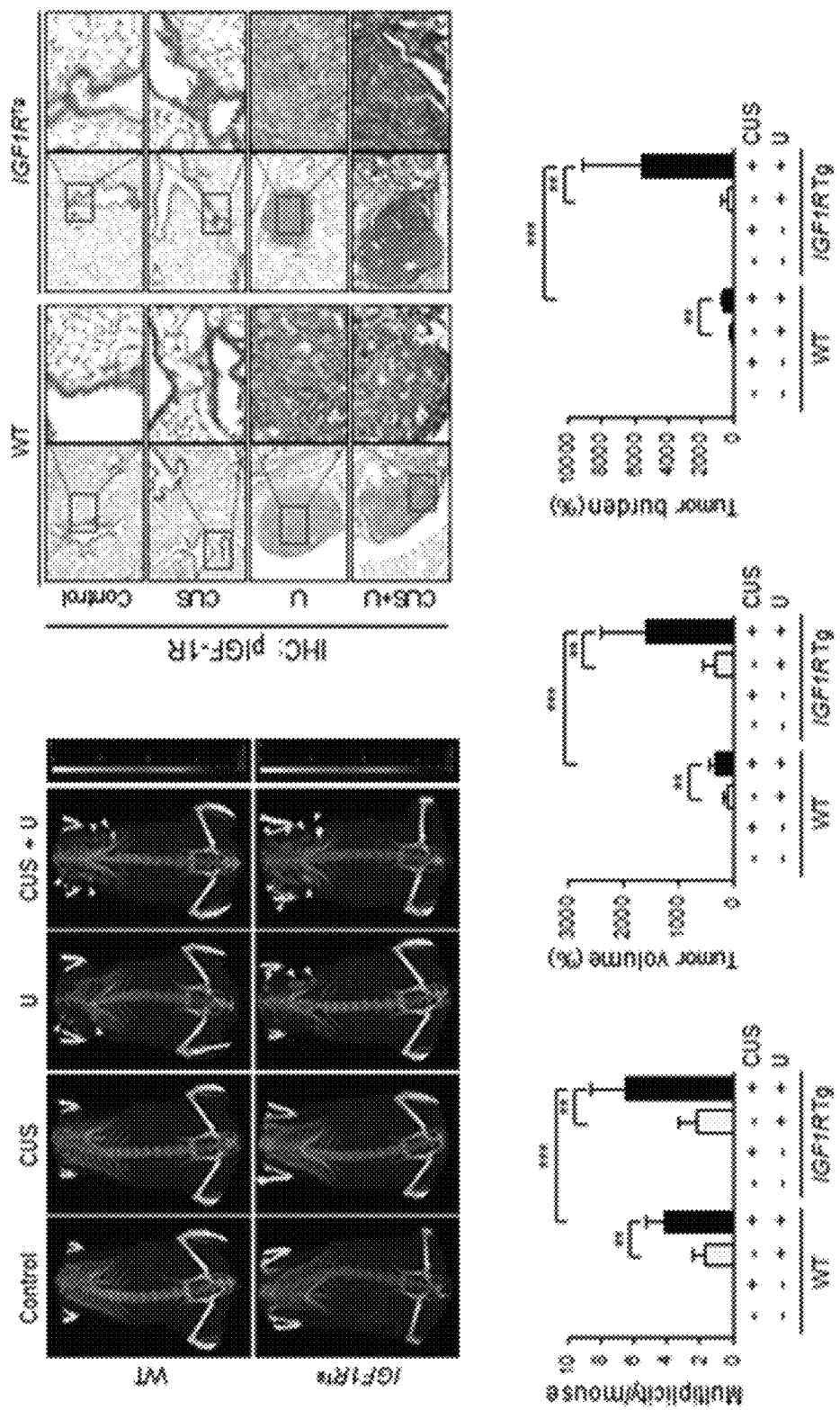
FIG. 36 shows that, compared with wild type mice, in IGF-1R transgenic mice showing lung-specific overexpression of IGF-1R, IGF-1R phosphorylation is increased by stress exposure, and promotion of lung carcinogenesis is significantly enhanced.
Figure 37:
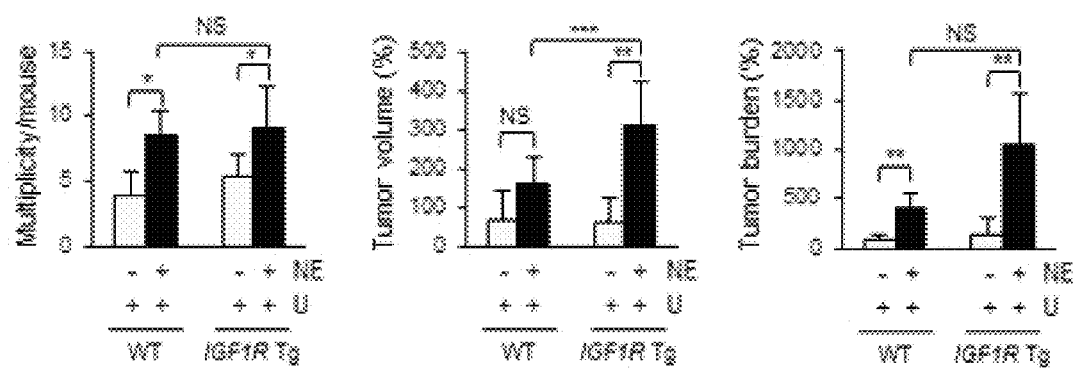
FIG. 37 shows that, compared with wild type mice, in IGF-1R transgenic mice showing lung-specific overexpression of IGF-1R, IGF-1R phosphorylation is increased by continuous NE exposure, and promotion of lung carcinogenesis is significantly enhanced.
Figure 37:
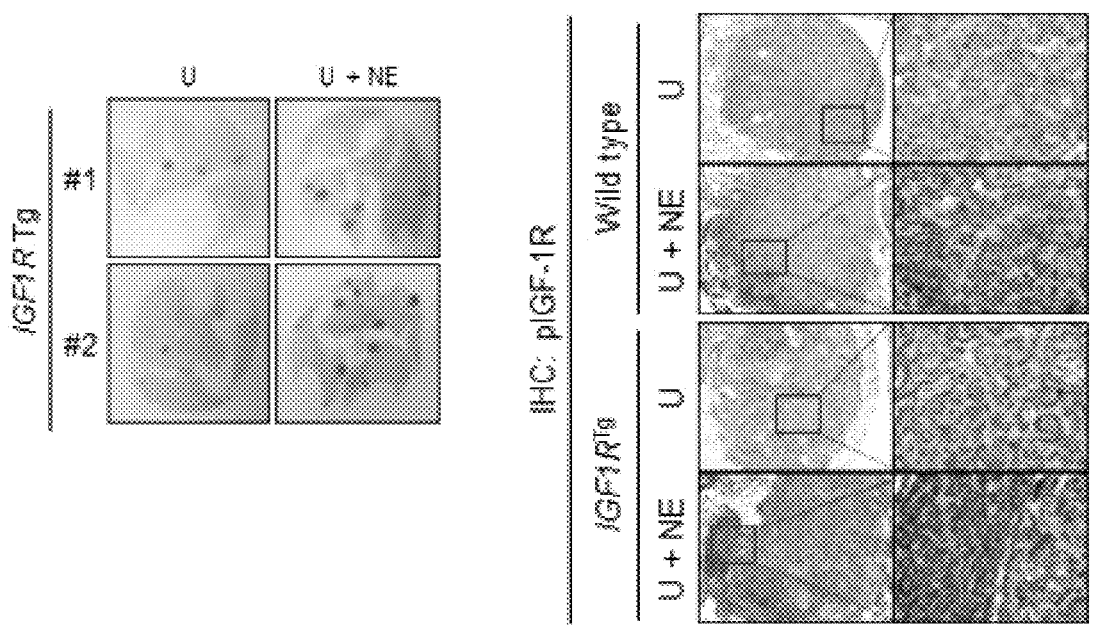

In addition, IGF-1R transgenic mice in which lung-specific IGF-1R was overexpressed were prepared according to the method described in Example 1-24, and IGF1R transgenic mice and wild type mice were each exposed to stress or continuously exposed to NE, followed by investigating the increase/decrease in IGF-1R phosphorylation and lung carcinogenesis. As a result, as shown in FIGS. 36 and 37, compared with wild type mice, it was confirmed that the IGF-1R phosphorylation was increased and promotion of lung carcinogenesis was significantly enhanced by the exposure to stress or NE in IGF1R transgenic mice.

Figure 38:
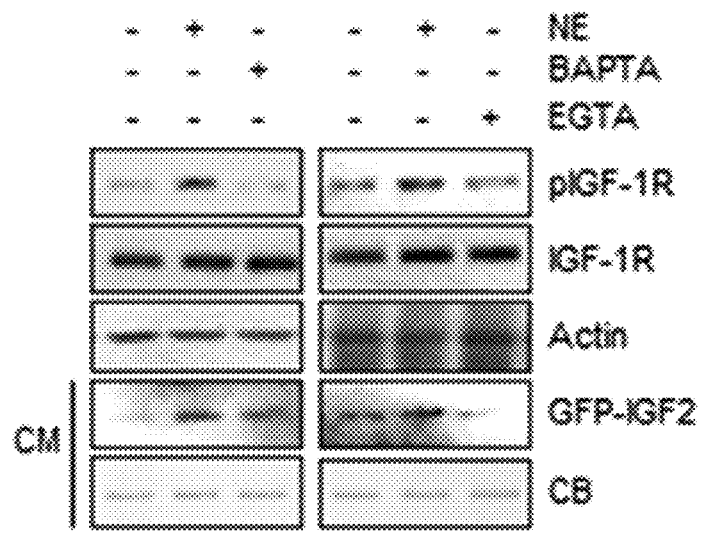
FIG. 38 shows that NE-induced IGF-1R activation and IGF2 secretion are blocked by a $Ca^{2+}$ chelator.
Figure 39:
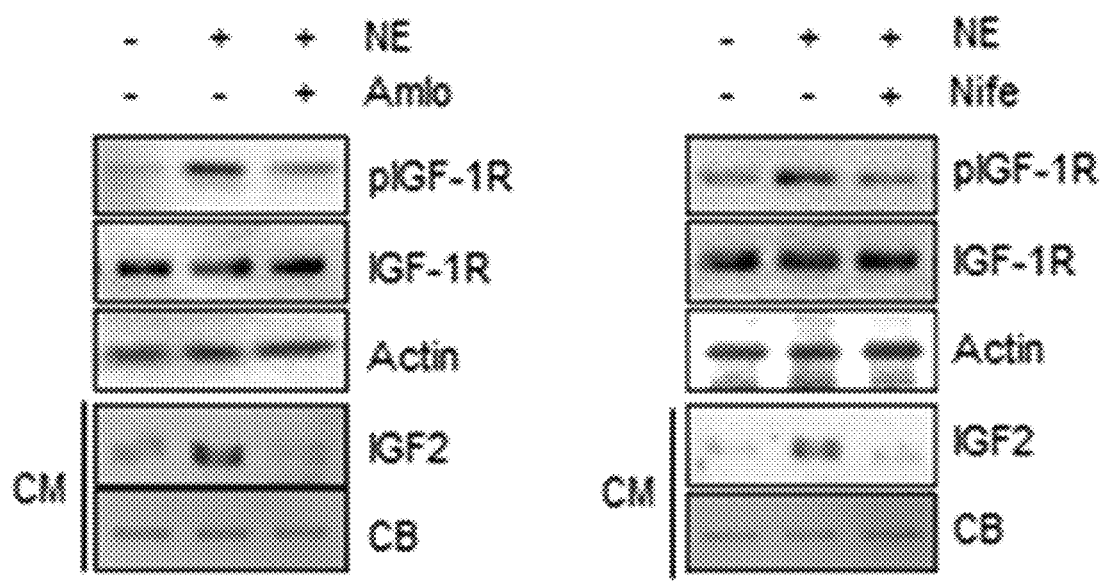
FIG. 39 shows that NE-induced IGF-1R activation and IGF2 secretion are blocked by a calcium channel blocker.
Figure 40:
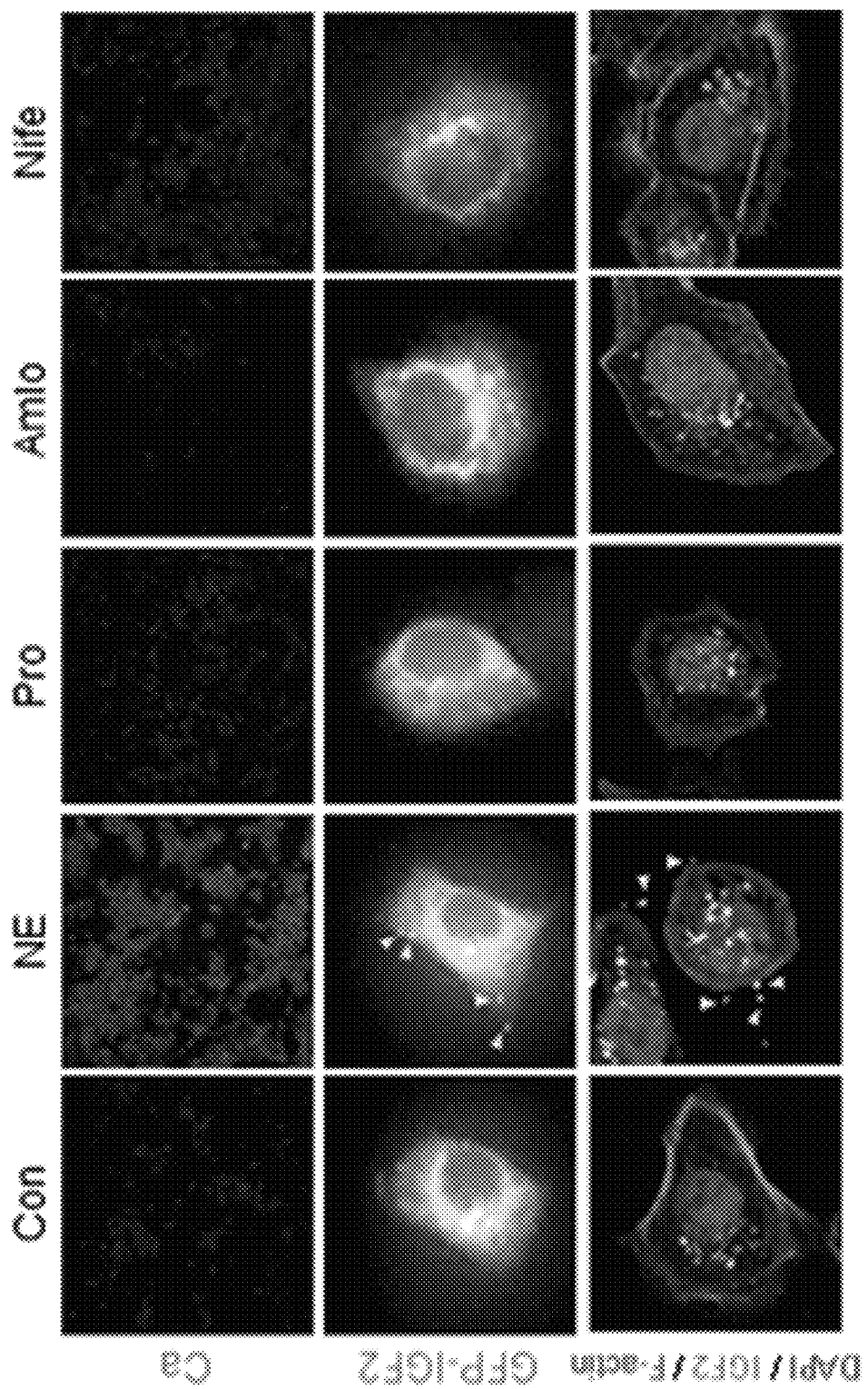
FIG. 40 shows that NE-induced IGF2 secretion is inhibited by a calcium channel blocker.

Example 9: Confirmation of Inhibitory Effect of Calcium Channel Blockers on NE-Mediated IGF-1R Signaling Activation, Cell Transformation, and Lung Carcinogenesis First, NE-treated lung epithelial cells were treated with each of $Ca^{2+}$ chelators (EGTA and BAPTA) and calcium channel blockers (nifedipine and amlodipine), and it was investigated whether IGF-1R activation and IGF2 secretion were changed. As a result, as shown in FIGS. 38 to 40, it was confirmed that the NE-mediated IGF-1R activation and IGF2 secretion were inhibited by the $Ca^{2+}$ chelators and calcium channel blockers.

Figure 41:
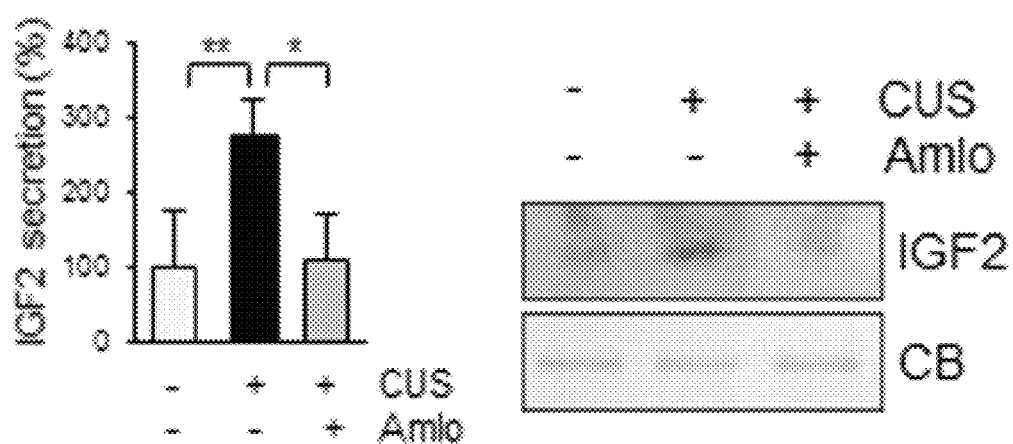
FIG. 41 shows that IGF2 secretion is increased in the lung of a mouse exposed to stress, and IGF2 secretion is inhibited by a calcium channel blocker, determined by bronchoalveolar lavage fluid (BALF) analysis.

Subsequently, it was investigated whether IGF2 secretion was changed by treatment with a calcium channel blocker in mouse lung tissues exposed to stress, according to the method described in Example 1-20. As a result, as shown in FIG. 41, it was confirmed that the IGF2 secretion was increased in the mouse lung exposed to stress, and the IGF2 secretion was inhibited by a calcium channel blocker.

Figure 42:
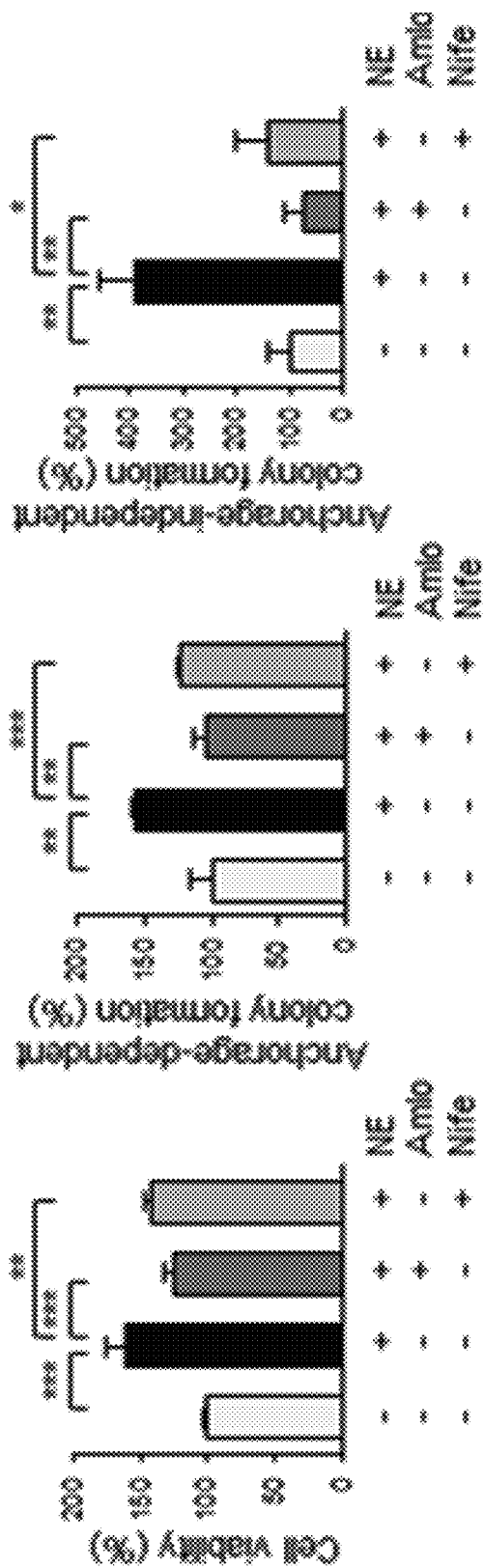
FIG. 42 shows that NE-induced increases in viability and colony formation of lung epithelial cells are inhibited by a calcium channel blocker, indicating that NE-induced transformation of lung epithelial cells is blocked.

Afterward, it was investigated whether NE-mediated transformation of lung epithelial cells was changed according to the treatment with a calcium channel blocker in NE-treated lung epithelial cells. As a result, as shown in FIG. 42, it was confirmed that the NE-induced increase in viability and colony formation of lung epithelial cells was inhibited by treatment with calcium channel blockers.

Figure 43:
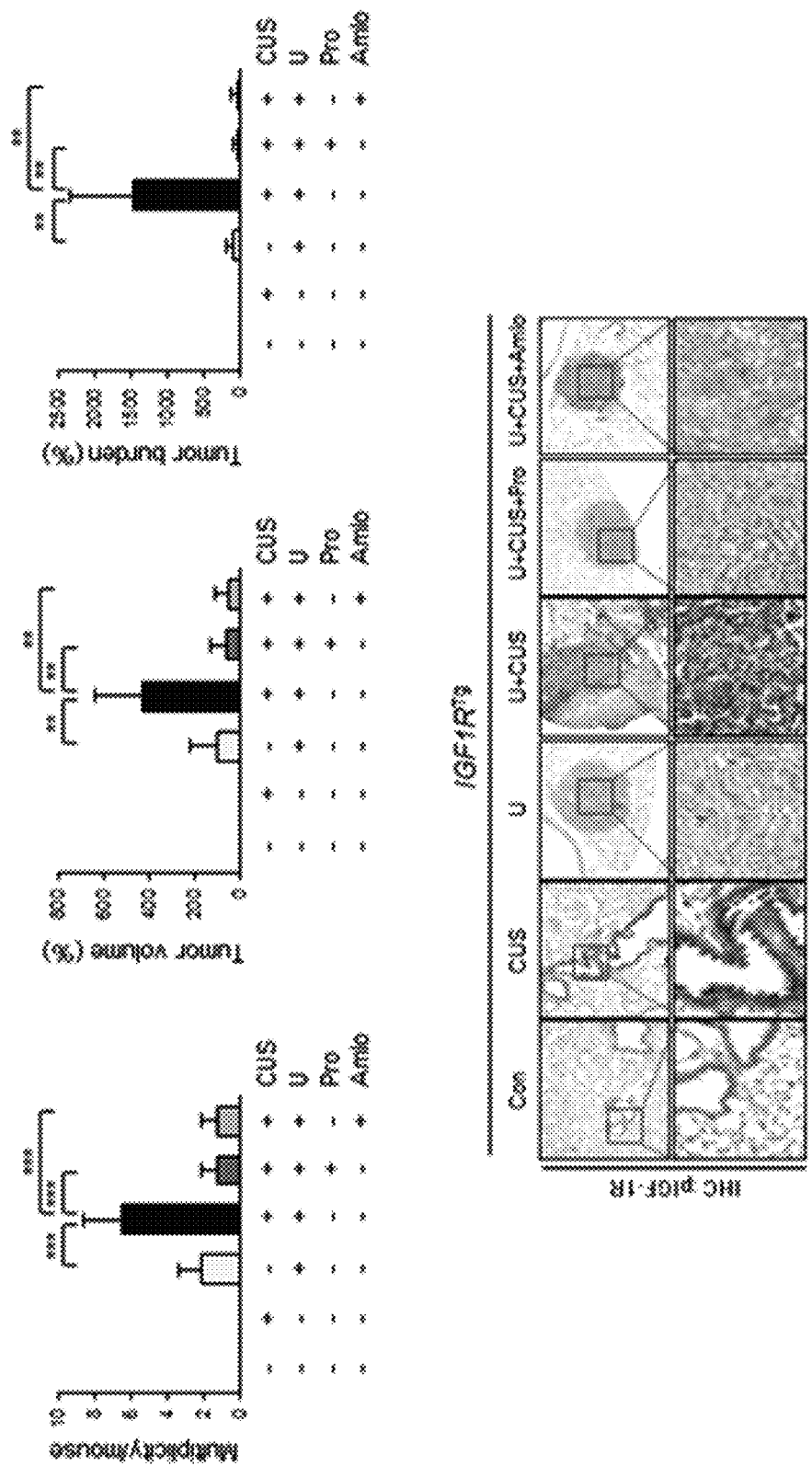
FIG. 43 shows that NE-induced tumorigenesis is inhibited by a calcium channel blocker, indicating a preventive effect of a calcium channel blocker on lung cancer induced by stress.

In addition, a tumorigenesis inhibitory effect caused by treatment with a calcium channel blocker in NE-induced lung carcinogenesis animal models was investigated. As a result, as shown in FIG. 43, it was confirmed that the NE-induced tumorigenesis was significantly suppressed by a calcium channel blocker.

Figure 44:
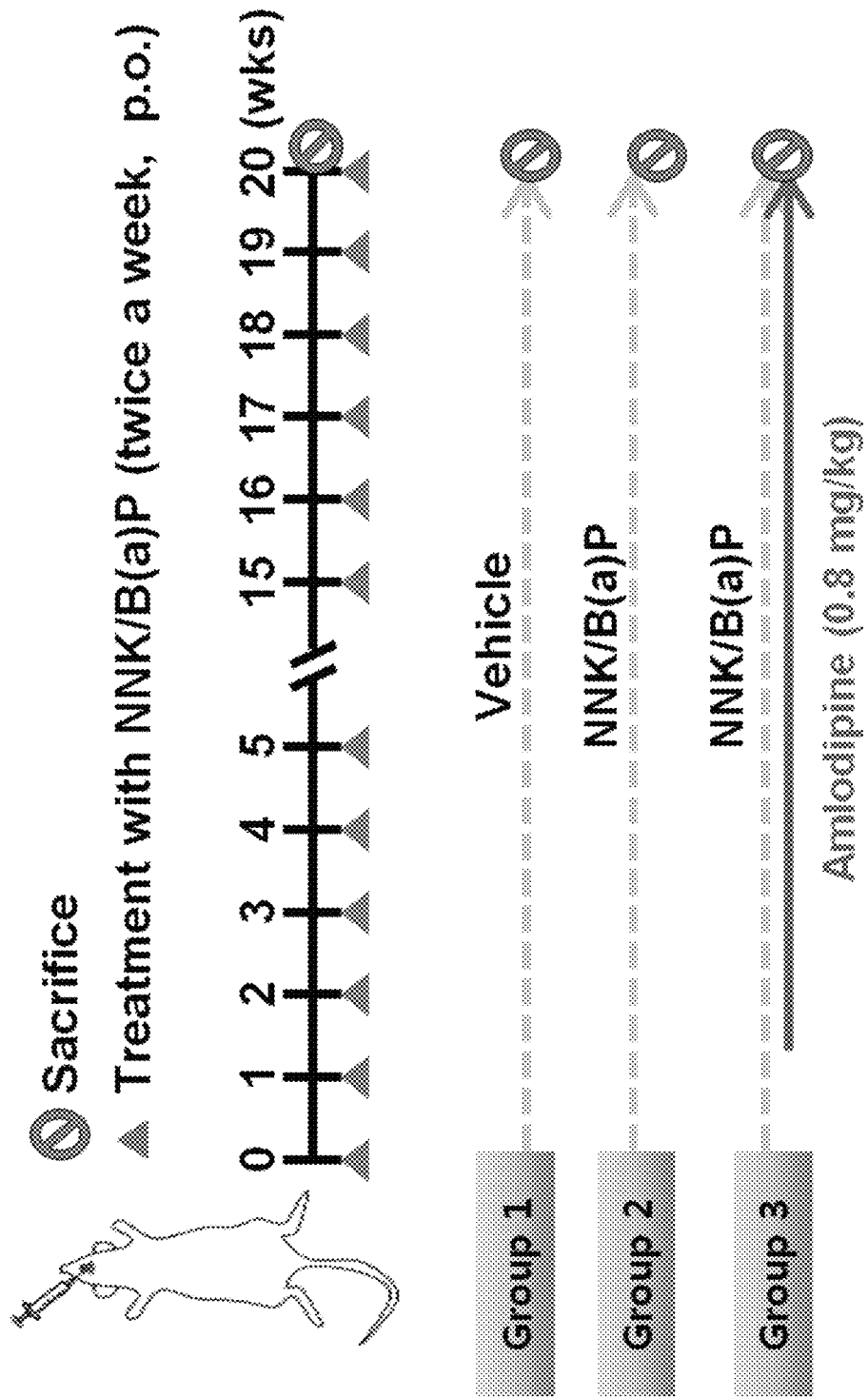
FIG. 44 is a diagram illustrating an experiment for confirming a preventive effect of a calcium channel blocker on emphysema.
Figure 45:
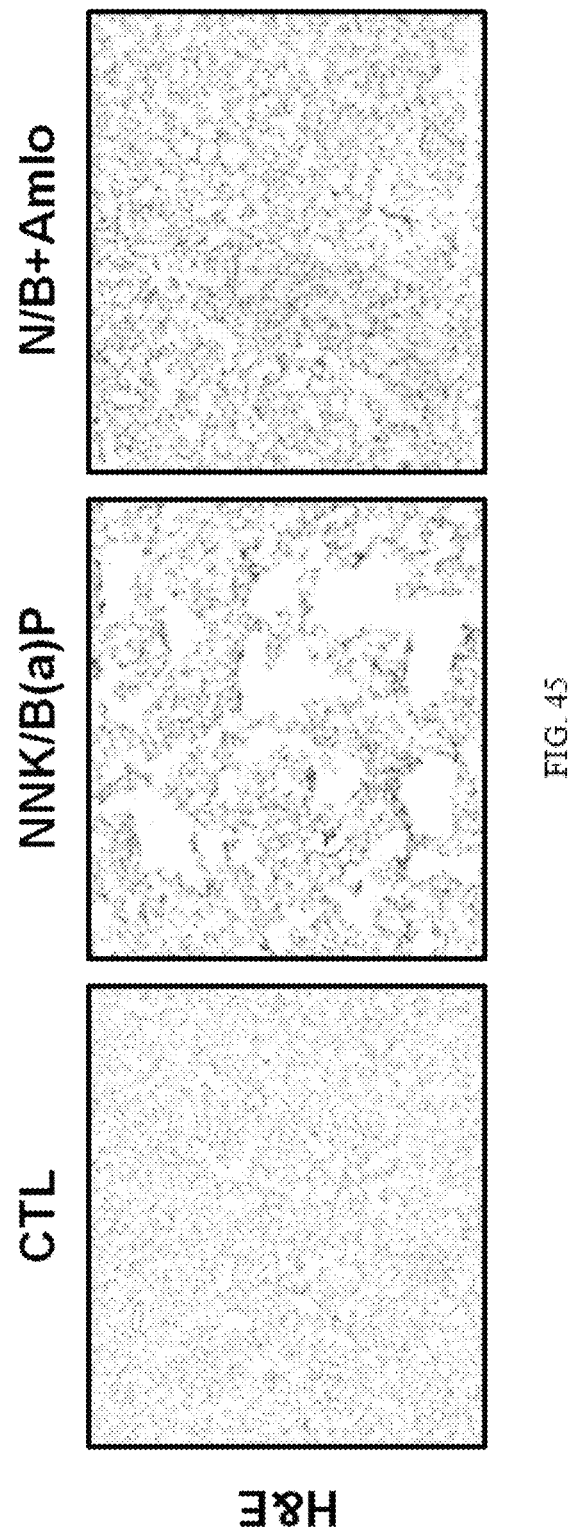
FIG. 45 shows the morphology of lung tissue in a control group (CTL), a tobacco-derived component (NNK/B[a]P)-treated group, and a calcium channel blocker (amlodipine; Amlo)-treated group, indicating that lung tissue collapse shown in the tobacco-derived component-treated group is inhibited by a calcium channel blocker.

Example 10. Confirmation of Emphysema Inhibitory Effect of a Calcium Channel Blocker After an emphysema-induced animal experiment was carried out according to the method described in Example 1-25 and the method illustrated in FIG. 44, mouse lung tissue sections were stained by H&E staining according to the method described in Example 1-18 to investigate the morphological change in lung tissues. As a result, as shown in FIG. 45, while normal lung tissue morphology was shown in control group (CTL), the collapse of typical lung tissue due to the treatment with tobacco-derived component (NNK/B[a]P) was observed, and it was confirmed that such an event was inhibited by treatment with a calcium channel blocker.

Figure 46:
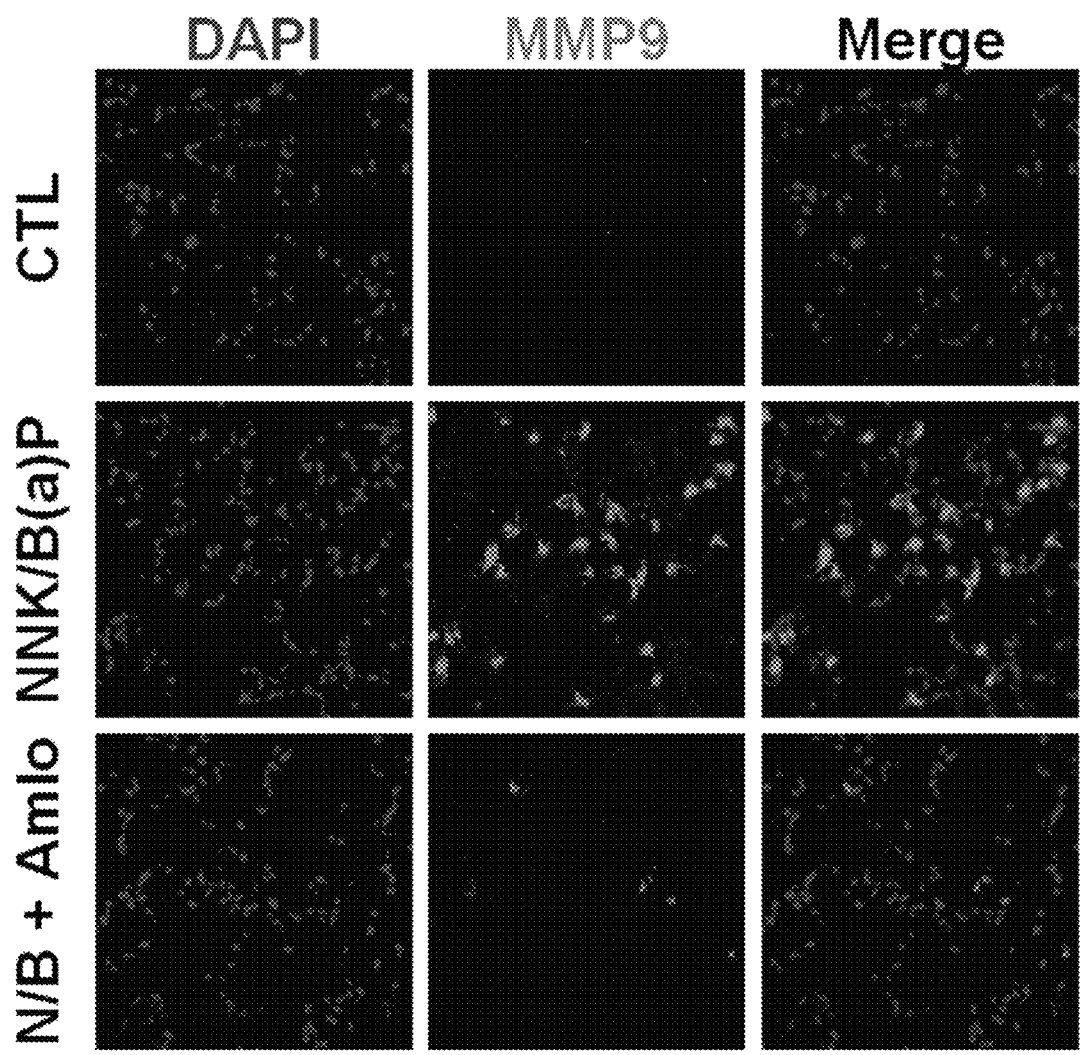
FIG. 46 shows the expression of a protease (MMP9) inducing lung tissue collapse, determined by fluorescent staining, indicating that the increase in MMP9 expression shown in a tobacco-derived component-treated group is inhibited by a calcium channel blocker.
Figure 47:
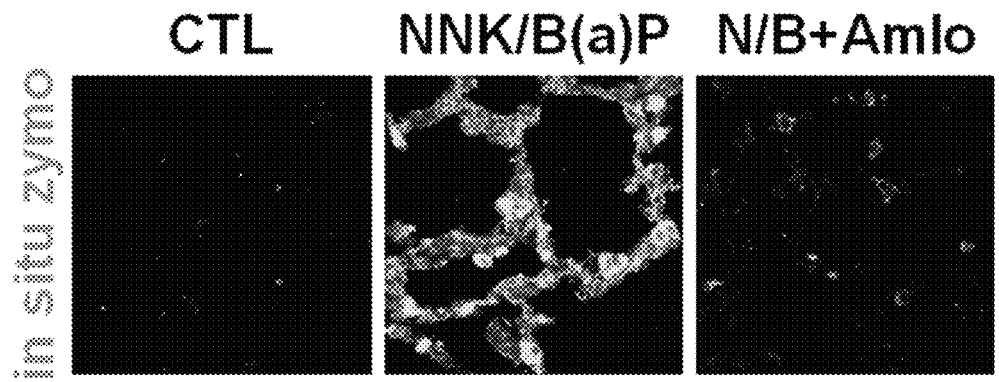
FIG. 47 shows the protease (MMP9) activity inducing lung tissue collapse, determined by in situ zymography using FITC-containing DQ gelatin, indicating that the increase in MMP9 activity shown in a tobacco-derived component-treated group is inhibited by a calcium channel blocker.

Subsequently, an inhibitory effect of a calcium channel blocker on expression and activation of MMP9, which is a key enzyme inducing lung tissue collapse shown in emphysema was investigated according to the methods described in Examples 1-13 and 1-26. As a result, as shown in FIGS. 46 and 47, it was confirmed that MMP9 expression noticeably increased by treatment with the tobacco-derived component was noticeably reduced by treatment with the calcium channel blocker. In addition, it was confirmed that green fluorescence was exhibited in the tobacco-derived component-treated group due to FITC released by MMP9 activity, whereas such an event was noticeably reduced due to inhibition of MMP9 activity in the calcium channel blocker-treated group.

Figure 48:
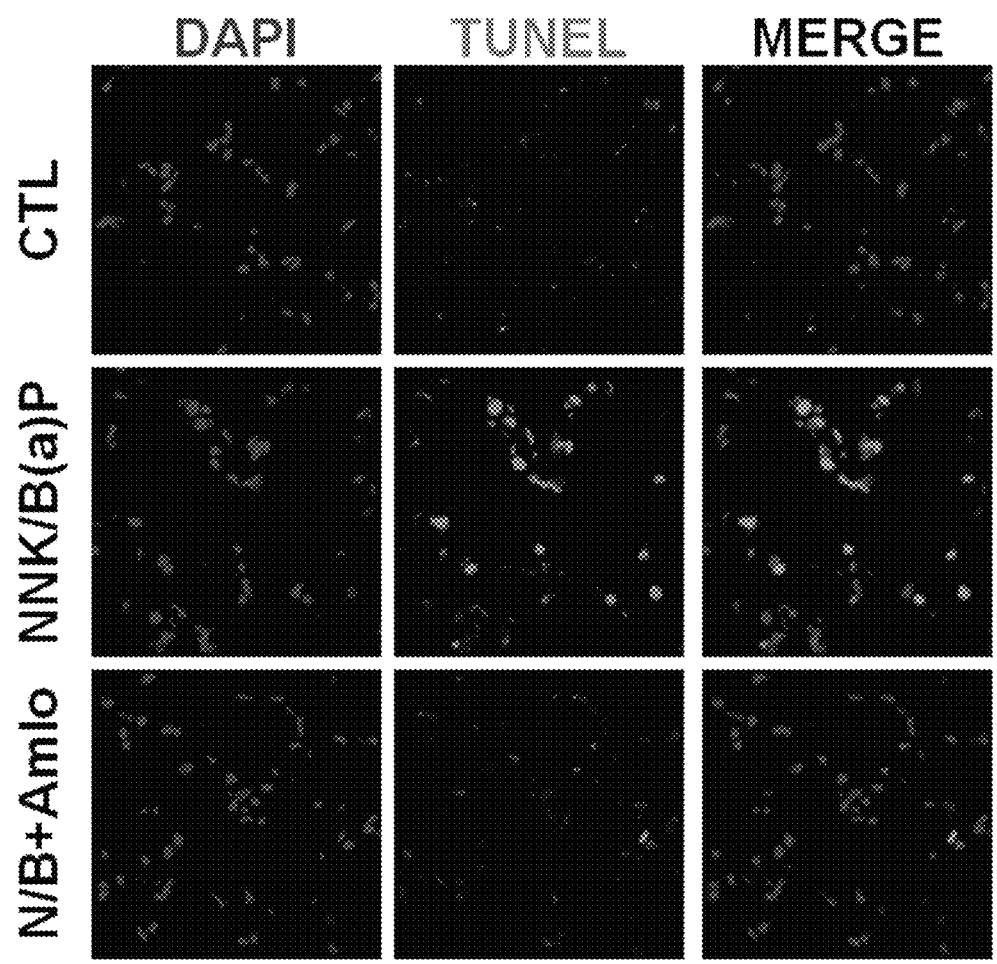
FIG. 48 shows an apoptosis-inducing action of epithelial cells, which is one of the biomarkers of lung tissue collapse, determined by TUNEL staining; indicating that the increase in apoptosis shown in a tobacco-derived component-treated group is inhibited by a calcium channel blocker.

Afterward, an inhibitory effect of the calcium channel blocker on increased apoptosis of lung tissue, which is one of the biomarkers of lung tissue collapse, was investigated according to the method described in Example 1-27. As a result, as shown in FIG. 48, it was confirmed that apoptosis was noticeably induced by the tobacco-derived components, and by treatment with a calcium channel blocker, such an action was effectively reduced.

Figure 49:
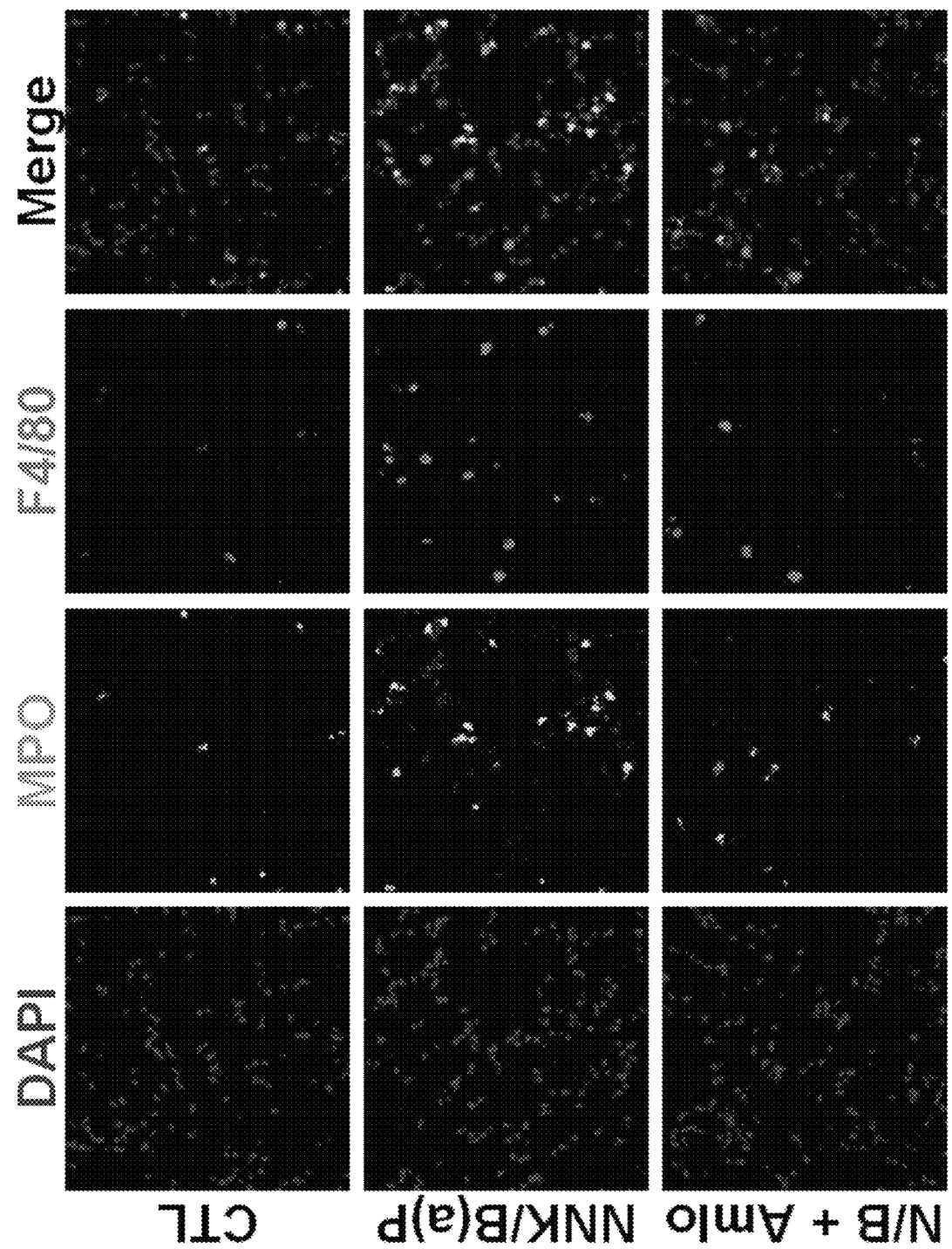
FIG. 49 shows neutrophils and macrophages immunostained with MPO and F4/80, respectively, determined by fluorescent microscopy, indicating that the recruitment of neutrophils and macrophages are increased in a tobacco-derived component-treated group, and such an event is inhibited by a calcium channel blocker.

In addition, the influx of immune cells known to express a protease inducing lung tissue collapse, such as neutrophils and macrophages was investigated by immunostaining each type of the cells with a selective marker (MPO: neutrophil; F4/80: macrophage) using a fluorescence microscope according to the method described in Example 1-13. As a result, as shown in FIG. 49, it was confirmed that, compared to the control group, the influx of neutrophils and macrophages was increased in the tobacco-derived component-treated group, and such an event was inhibited by treatment with a calcium channel blocker.

Figure 50:
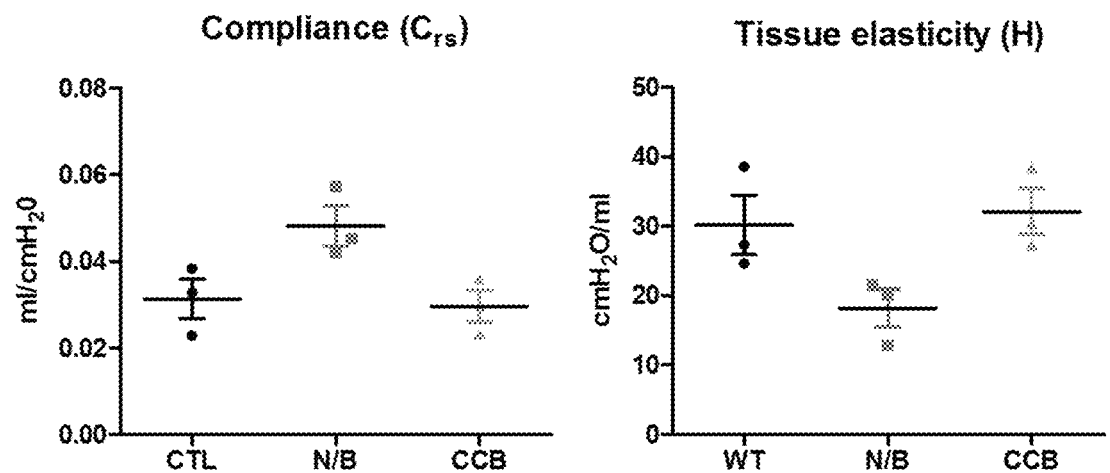
FIG. 50 shows the result obtained by measuring the change in lung function in a control group (CTL), a tobacco-derived component-treated group, and a tobacco-derived component and calcium channel blocker-treated group, determined using the FlexiVent system; in which the characteristics of emphysema lesions, such as increased lung compliance and decreased lung elasticity are shown in the tobacco-derived component-treated group, indicating that the lung function is recovered similar to that of the control group by treatment with a calcium channel blocker.

And finally, an inhibitory effect of a calcium channel blocker on lung dysfunction caused by the tobacco-derived component was investigated according to the method described in Example 1-28. The lung function was represented as lung compliance and elasticity, and as a result, as shown in FIG. 50, it was confirmed that the characteristics of emphysema lesions such as increased lung compliance and decreased elasticity were shown in the tobacco-derived component-treated group due to the tobacco-derived component, and such an event was reversed to the control group levels by treatment with a calcium channel blocker.

It would be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

The invention claimed is:

1. A method of preventing or suppressing lung cancer formation in a subject who has been exposed to smoking or stress and the IGF-1R (Insulin-like Growth Factor-1 Receptor) signaling pathway is activated in pre-neoplastic lung tissues, comprising:

administering to the subject a pharmaceutical composition consisting of an effective amount of an antihypertensive agent selected from the group consisting of a calcium channel blocker, an angiotensin-converting enzyme inhibitor, an angiotensin receptor antagonist and a mixture thereof, and a pharmaceutically acceptable carrier, and thereby inhibiting the activation of the IGF-1R signaling pathway and suppressing transformation of lung epithelial cells, or generation and growth of lung cancer cells.

2. The method of claim 1, wherein the calcium channel blocker is selected from the group consisting of amlodipine, barnidipine, benidipine, cilnidipine, efonidipine, felodipine, isradipine, lacidipine, lercanidipine, manidipine, nicardipine, nifedipine, nilvadipine, nimodipine, nisoldipine, nitrendipine, verapamil, diltiazem, and a mixture thereof.

3. The method of claim 1, wherein the angiotensin-converting enzyme inhibitor is selected from the group consisting of alacepril, benazepril, captopril, cilazapril, delapril, enalapril, fosinopril, imidapril, lisinopril, moexipril, perindopril, quinapril, ramipril, temocapril, zofenopril and a mixture thereof.

4. The method of claim 1, wherein the angiotensin receptor antagonist is selected from the group consisting of candesartan, eprosartan, fimasartan, irbesartan, losartan, olmesartan, valsartan, telmisartan and a mixture thereof.

* * * * *

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: human IGF2 transgene Primer F

<400> SEQUENCE: 1

```
agacaccaat gggaatcc                                                    18

<210> SEQ ID NO 2
<211> LENGTH: 19
<212> TYPE: DNA
<213> ORGANISM: Artificial Sequence
<220> FEATURE:
<223> OTHER INFORMATION: human IGF2 transgene Primer R

<400> SEQUENCE: 2
tgctcacttc cgattgctg                                                   19

<210> SEQ ID NO 3
<211> LENGTH: 21
<212> TYPE: DNA
<213> ORGANISM: Artificial Sequence
<220> FEATURE:
<223> OTHER INFORMATION: human IGF-1R transgene Primer F

<400> SEQUENCE: 3
ctggctggcg tggaaatatt c                                                21

<210> SEQ ID NO 4
<211> LENGTH: 20
<212> TYPE: DNA
<213> ORGANISM: Artificial Sequence
<220> FEATURE:
<223> OTHER INFORMATION: human IGF-1R transgene Primer R

<400> SEQUENCE: 4
ccactcggaa cagcagcaag                                                  20
```